United States Patent
Yasumura et al.

[11] Patent Number: 5,677,322
[45] Date of Patent: Oct. 14, 1997

[54] MAILLARD REACTION INHIBITOR

[75] Inventors: Koichi Yasumura; Keisuke Miyajima; Takao Nagahama; Shintaro Ishikawa, all of Shiga; Yuko Nakagawa, Nara; Kazuhisa Sugiyama, Shiga, all of Japan

[73] Assignee: Otsuka Pharmaceutical Co., Ltd., Tokyo, Japan

[21] Appl. No.: 325,233

[22] PCT Filed: Feb. 21, 1994

[86] PCT No.: PCT/JP94/00260

§ 371 Date: Oct. 21, 1994

§ 102(e) Date: Oct. 21, 1994

[87] PCT Pub. No.: WO94/19335

PCT Pub. Date: Sep. 1, 1994

[30] Foreign Application Priority Data

Feb. 26, 1993 [JP] Japan .................................. 5-037720
Sep. 16, 1993 [JP] Japan .................................. 5-230243

[51] Int. Cl.$^6$ ........................ C07D 277/54; A01K 31/425
[52] U.S. Cl. .......................................... 514/369; 548/184
[58] Field of Search ............................. 548/184; 514/369

[56] References Cited

PUBLICATIONS

Belik, Tzv. Vyssh Uchebn. Zaved Khim Khim Teknol 1992, 35(9) 99–106 Chem Abstract Only.
WO/18501, Apr. 6, 1992; EPA 0 476 455, Sep. 6, 1991; Can. J. Chem., vol. 37 (1959) 1597–1607; J. Heterocyclic Chem., 15 (1978) 401–411; Z. Chem., 8 (9) (1968) 339–340; EPA 0 316 852, Nov. 14, 1988; EPA 0 222 313, Nov. 5, 1986.

*Primary Examiner*—Robert Gerstl
*Attorney, Agent, or Firm*—Sughrue, Mion, Zinn, Macpeak & Seas, PLLC

[57] ABSTRACT

A compound represented by the following formula is disclosed:

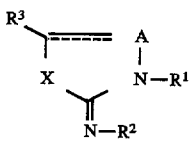

wherein the all symbols are defined in the disclosure.
A process for producing the compound, and a method for treating diseases caused by a Maillard reaction in living body using the compound are also disclosed.

16 Claims, No Drawings

MAILLARD REACTION INHIBITOR

TECHNICAL FIELD

The present invention relates to a novel Maillard reaction inhibitor.

BACKGROUND ART

The Maillard reaction is a reaction which starts in a living body with an attack by a nucleophilic reaction with a free amino group present in a protein on an aldehyde group of a reducing sugar such as glucose to from a Schiff base which is called aldimine. Then, aldimine successively cause a rearrangement to form a more stable Amadori compound (non-enzymatic glycation). The Amadori compound further causes a series of reaction with other proteinous amino groups, thereby to form a brown fluorescent material and to cause a crosslinking between proteins. Historically, Maillard reported in 1912 that a mixed solution of an amino acid and a reducing sugar, when heated, is colored into brown (L. C. Maillard, *Compt. Rend. Soc. Biol.*, 72, 599 (1912)) and, since then, the reaction is called Maillard reaction. At that time, Maillard already suggested that the reaction could occur in a living body.

In 1968, Rabber et al found that hemoglobin $A_{1c}$ which is a very small fraction of hemoglobin is increased in the blood of diabetic patients (S. Rabber et al, *Clin. Chim. Acta.*, 22, 296 (1968)) and further, it was found that the hemoglobin $A_{1c}$ was formed by bonding glucose to the N terminal valine of the hemoglobin β-chain in the form of an Amadori rearrangement (V. J. Stevens, H. Vlassara, A. Abati, & A. Cerami, *J. Biol. Chem.*, 252, 2998 (1977)), etc., and the occurrence of a non-enzymatic glycation in a living body was proved.

Recently, it has been confirmed that various bioproteins may undergo the Maillard reaction. For example, it is reported that the amount of hemoglobin subjected to a glycation is increased thrice in a diabetic (E. C. Abraham et al, *J. Lab. Clin. Med.*, 102, 187 (1983)).

Also, it is reported that the amount of glycation is increased in the serum albumin of diabetic patients (R. Dolhofer and O. H. Wieland, *Diabetes*, 29, 417 (1980)). Also, it is reported that fluorescence is increased in the skin collagen obtained from diabetic patients (Vincent M. Monnier et al, *Proc. Natl. Acad. Sci. U.S.A.*, 81, 583 (1984)).

The non-enzymatic glycation is a phenomenon observed in a healthy person, but the accumulation of the brown fluorescent material is a protein having a delayed metabolic turnover rate and is markedly observed in aging and a diabetic state of increasing a blood sugar value. The reason therefor has been reported by Patrick et al that an accumulated amount of the Maillard reaction product is determined by a blood sugar value, the metabolic turnover rate of the target protein thereof, etc. (J. S. Patrick, S. R. Thorpe and J. W. Baynes, *Journal of Gerontology*, 45, 1, B18–23 (1990)).

The correlation between such a Maillard reaction product and various cause of diseases relating to diabetes and aging has been discussed. For example, it is reported that, when a serum protein which has been subjected to glycation is intravenously administrated to mice for 12 weeks, a typical renal disorder in diabetes is caused (B. A. McVerry et al, *The Lancet*, 5, 738 (1980)). It is also considered that the non-enzymatic glycation of a nervous myelin protein takes part in one of the causes of the diabetic nervous disorder (V. M. Monnier et al, *Clin. Endocrinol. Metab.*, 11, 431 (1982)).

An eyeball lens crystalline is a specific protein causing no metabolic turnover after being biosynthesized, and Cerami et al found that, when the crystalline undergoes the glycation, a colorless crosslinked compound having a disulfide linkage and a colored crosslinked compound having a fluorescence are formed (V. M. Monnier & A. Cerami, *Science*, 211, 491 (1981) and V. M. Monnier & A. Cerami, *Biochim. Biophys. Acta.*, 760, 97 (1983)). When the crystalline undergoes glycation, polymerization, insolubilization, increase in fluorescence, and coloring in brown occur, closely similar to the changes of the eyeball lens with aging (S. H. Chiou et al, *J. Biol. Chem.*, 256, 5176 (1981)).

Collagen and elastin which are proteins constituting connective tissues are proteins showing very slow metabolic turnover and a combined product with glucose has been found in a renal glomerulus base membrane, a skin, a tendon, etc. (V. M. Monnier et al, "Maillard Reaction in Food", *Prog. Food Nutr. Sci., i*, 315, Pergamon Press, London). Brownlee et al showed that, in a diabetic rat, crosslinking of collagen increases in the wall of the blood vessel, thereby to accumulate a fluorescent material, and also that such a crosslinking occurs by a non-enzymatic mechanism (M. Brownlee et al, *Science*, 232, 1629 (1989)). The reaction with hardening of the arterial wall has also been considered (H. Rosenburn et al, *Biochem. Biophys., Res. Commun.*, 91, 498 (1979)).

As described above, it is considered that the Maillard reaction in a living body takes part in various diseases relating to diabetes and aging.

In these points of view, many studies have been made on the treatment of diseases relating to diabetes and aging. For example, EP-A-0 316 852 and EP-A-0 222 313 disclose compositions for inhibiting the advanced glycosylation of a target protein, and JP-A-64-56614 (the term "JP-A" as used herein means "unexamined published Japanese Patent Application") and EP-A-0 531 812 disclose a Maillard reaction inhibitor.

On the other hand, various compounds containing a thiazolidine, thiazoline or thiazole residue have been reported. For example, JP-B-30-3225 (the term "JP-B" as used herein means "examined Japanese Patent Publication"), JP-B-30-8940, JP-B-41-11255 and JP-B-41-1256 disclose compounds containing a thiazolidine, thiazoline or thiazole residue as an antibacterial agent; JP-B-46-15936 discloses a compound containing a thiazolidine residue as an antiviral agent; JP-A-4-66579 and WO 92/18501 disclose compounds containing a thiazolidine residue as an agent having hypolipidemic and/or hypoglycemic activities; EP-A-0 476 455 discloses a compound containing a thiazole residue as a compound useful in the determination of reducing substances such as nicotinamide adenine dinucleotide; and Can. J. Chem. 37, 1597–1607 (1978), J. Heterocyclic Chem., 15, 401 (1978) and Z. Chem., 8(9), 339–40 reports about synthesis of compounds containing a thiazolidine, thiazoline or thiazole residue.

DISCLOSURE OF INVENTION

An object of the present invention is to provide a novel Maillard reaction inhibitor.

According to the present invention, there is provided a Maillard reaction inhibitor comprising, as an active ingredient, at least one compound selected from those represented by the general formula (1):

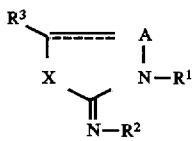

wherein:

$R^1$ represents a hydrogen atom, a lower alkoxycarbonyl-lower alkyl group, a phenyl-lower alkyl group which may have from 1 to 3 substituents selected from a halogen atom, a hydroxyl group, a nitro group, a lower alkyl group, a lower alkoxy group and a lower alkylthio group on the phenyl ring thereof, or a phenyl group which may have 1 to 3 substituents selected from a halogen atom, a hydroxyl group, a nitro group, a lower alkyl group, a lower alkoxy group and a lower alkylthio group;

$R^2$ represents an amino group, a phenylsulfonylamino group which may have a substituent selected from a halogen atom, a hydroxyl group, an amino group and a lower alkanoylamino group on the phenyl ring thereof, or $-N=R^4$ (wherein $R^4$ represents a lower alkylidene group, a lower alkylidene group having 1 or 2 lower cycloalkyl groups, a lower cycloalkylidene group, a diphenyl-lower alkylidene group or a phenyl-lower alkylidene group);

$R^3$ represents:

a hydrogen atom, a lower alkyl group, a lower alkenyl group, a phenyl-lower alkoxy-lower alkyl group, a phenyl group which may have a hydroxyl group, a 5-membered or 6-membered unsaturated heterocyclic-lower alkyl group having 1 or 2 hetero atoms selected from a nitrogen atom and a sulfur atom (the heterocyclic ring may be condensed with a benzene ring and a hydroxyl group may be located as a substituent on either one or both of the heterocyclic ring and the benzene ring being condensed therewith), $-W-(NH)_b-CO-OR^5$ (wherein W represents a lower alkylene group, $R^5$ represents a hydrogen atom, a lower alkyl group, or a phenyl-lower alkyl group, and b is 0 or 1), $-Z-CO-R^a$ {wherein Z represents a lower alkylene group, $R^a$ represents -Tyr(OR$^{a1}$)-OR$^{b1}$, -Leu-OR$^{b2}$, -Trp-OR$^{b3}$, -Asp(OR$^{a2}$)-OR$^{b4}$, -Ph-Gly-OR$^{b5}$ (wherein R$^{a1}$ and R$^{a2}$ each represents a hydrogen atom or a benzyl group, and R$^{b1}$, R$^{b2}$, R$^{b3}$, R$^{b4}$ and R$^{b5}$ each represents a hydrogen atom or a lower alkyl group) or $-N(R^6)-R^7$ (wherein $R^6$ represents a lower alkyl group, a carboxy-lower alkyl group, a lower alkoxycarbonyl-lower alkyl group, a phenyl-lower alkyl group, a lower cycloalkyl group, a phenyl group which may have 1 to 3 substituents selected from a halogen atom, a hydroxyl group, a nitro group, a lower alkyl group, lower alkoxy group, a lower alkylthio group, a carboxyl group, a lower alkoxycarbonyl group, a phenyl-lower alkoxy group, a lower alkylenedioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group and a 6-lower alkanoyloxy-2,5,7,8-tetramethyl-2-chromanylmethyloxy group, a naphthyl group, a 3,4-dihydroxycarbostyryl group, a morpholino group, or a 5-membered or 6-membered unsaturated heterocyclic-lower alkyl group having 1 or 2 hetero atoms selected from a nitrogen atom, an oxygen atom and a sulfur atom, and $R^7$ represents a hydrogen atom or a lower alkyl group)}, or a group:

{wherein B represents a lower alkylene group, $R^8$ represents a hydroxyl group, a nitro group, an amino group, a halogen atom, a lower alkyl group, a lower alkoxy group, a phenoxy group, a phenyl-lower alkyl group, a lower alkylthio group, a phenylthio group which may have a halogen atom, a phenyl-lower alkylthio group, a benzoylamino group which may have 1 to 3 halogen atoms, or $-O-D-R^9$ (wherein D represents a lower alkylene group, $R^9$ represents a phenyl group which may have 1 to 3 substituents selected from a halogen atom, a hydroxyl group, a nitro group, a lower alkyl group, a lower alkoxy group and a lower alkylthio group on the phenyl ring thereof (the phenyl ring may be condensed with a benzene ring or a cyclohexane ring), a 5-membered or 6-membered, saturated or unsaturated heterocyclic group having a hetero atom selected from a nitrogen atom, a sulfur atom and an oxygen atom (the heterocyclic ring may be condensed with a benzene ring and 1 to 5, in total, substituents selected from a hydroxyl group and a lower alkyl group may be located on either one or both of the heterocyclic ring or the benzene ring being condensed with the heterocyclic ring), a lower cycloalkyl group or a naphthoquinone group), and n is 0 or an integer of from 1 to 3};

X represents $-S-$ or $-N(R^{10})-$ (wherein $R^{10}$ represents a hydrogen atom or a lower alkoxycarbonyl-lower alkyl group);

$---$ represents a single bond or a double bond;

A, when $---$ is a single bond, represents a carbonyl group, or A, when $---$ is a double bond, represents $=C(R^{11})-$ {wherein $R^{11}$ represents a lower alkyl group which may have 1 to 3 halogen atoms, a lower alkoxycarbonyl-lower alkyl group, a carboxy-lower alkyl group, a pyridyl group, a thienyl group, a thiazolyl group, a phenylcarbamoyl-lower alkyl group which may have 1 or 2 lower alkoxy groups on the phenyl ring thereof, or a group:

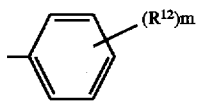

(wherein $R^{12}$ represents a halogen atom, a hydroxyl group, a nitro group, a lower alkyl group, a lower alkoxy group, a lower alkylthio group, a carboxy group, a phenylthio group, or a phenyl-lower alkoxy group which may have 1 to 3 halogen atoms on the phenyl ring thereof, and m is 0 or an integer of from 1 to 3)}; and the above $R^4$ and $R^{10}$ may bind to each other to form a 6- to 8-membered ring (with the proviso that A represents a carbonyl group in this case), and $R^3$ and $R^{11}$ may bind to each other to form a 5- to 8-membered ring, with the proviso that, when $R^3$ represents a hydrogen atom and A represents a carbonyl group, $R^1$ does not represent a hydrogen atom or a lower alkoxycarbonyl-lower alkyl group; or a pharmaceutically acceptable salt thereof.

The compound and the salt thereof according to the present invention are useful for the treatment and/or the prevention of various diabetic complications such as coronary disease, a periphery circulatory disease, a cerebrovascular disorder, diabetic neurosis, a renal disease, an atherosclerosis, an articular sclerosis, a cataract, and retinitis or the diseases caused by aging, such as an atherosclerosis, a senile cataract, etc., by inhibiting the Maillard reaction. Further, the compound and the salt thereof according to the present invention have a hypoglycemic effect and thus are useful as an antidiabetic drug for treating diabetes mellitus. The compound and the salt thereof according to the present invention have various advantages including a long-lasting action, excellent absorption characteristics in vivo, a low toxicity, a high safety, a high stability as a compound and easiness in preparation.

Each group as herein used is described hereinafter in detail.

Examples of the lower alkoxycarbonyl-lower alkyl group include alkoxycarbonylalkyl groups in which the alkoxy moiety has from 1 to 6 carbon atoms and the alkyl moiety has from 1 to 6 carbon atoms, such as methoxycarbonylmethyl, ethoxycarbonylmethyl, 3-methoxycarbonylpropyl, 4-ethoxycarbonylbutyl, 6-propoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

Examples of the halogen atom, regardless of whether it exists independently or exists in other groups, include fluorine, chlorine, bromine and iodine atoms.

Examples of the lower alkyl group, regardless of whether it exists independently or exists in other groups, include straight chain or branched alkyl groups having from 1 to 6 carbon atoms, such as methyl, ethyl, propyl, isopropyl, butyl, tert-butyl, pentyl, hexyl, and the like.

Examples of the lower alkoxy group, regardless of whether it exists independently or exists in other groups, include straight chain or branched alkoxy groups having from 1 to 6 carbon atoms, such as methoxy, ethoxy, propoxy, isopropoxy, butoxy, tert-butoxy, pentyloxy, hexyloxy, and the like.

Examples of the lower alkylthio group include alkylthio groups in which the alkyl moiety is a straight chain or branched alkyl group having from 1 to 6 carbon atoms, such as methylthio, ethylthio, propylthio, butylthio, isopropylthio, tert-butylthio, pentylthio, hexylthio, and the like.

Examples of the phenyl-lower alkyl group which may have from 1 to 3 substituents selected from a halogen atom, a hydroxyl group, a nitro group, a lower alkyl group, a lower alkoxy group and a lower alkylthio group on the phenyl ring thereof include phenyl-lower alkyl groups having a phenyl group which may have from 1 to 3 substituents selected from a halogen atom, a hydroxyl group, a nitro group, a straight chain or branched lower alkyl group having from 1 to 6 carbon atoms, a straight chain or branched lower alkoxy group having from 1 to 6 carbon atoms and a straight chain or branched lower alkylthio group having from 1 to 6 carbon atoms on the phenyl ring thereof and in which the alkyl moiety is a straight chain or branched group having from 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl,2-phenylpropyl, 2-fluorobenzyl, 3-fluorobenzyl, 4-fluorobenzyl, 4-chlorobenzyl, 4-bromobenzyl, 4-iodobenzyl, 2-(2-fluorophenyl)ethyl, 3-(3-chlorophenyl)propyl, 4-(4-bromophenyl)butyl, 5-(4-iodophenyl)pentyl, 6-(3-fluorophenyl)hexyl, 1,1-dimethyl-2-(2-chlorophenyl)ethyl, 2-methyl-3-(4-chlorophenyl) propyl, 2-(4-fluorophenyl)propyl, 2,5-difluorobenzyl, 2,3-dichlorobenzyl, 2-(2,4-dibromophenyl)ethyl, 2-(2,6-difluorophenyl)ethyl, 3-(3,4-dichlorophenyl)propyl, 4-(3,5-dibromophenyl)butyl, 5-(3,4-difluorophenyl)pentyl, 6-(3,5-dichlorophenyl)hexyl, 2,4,5-trifluorobenzyl, 2-(2,4,6-trichlorophenyl)ethyl, 3-(3,4,5-trifluorophenyl)propoxy, hydroxybenzyl, 3-hydroxybenzyl, 4-hydroxybenzyl, 2-(2-hydroxyphenyl)ethyl, 3-(3-hydroxyphenyl)propyl, 4-(4-hydroxyphenyl)butyl, 5-(4-hydroxyphenyl)pentyl, 6-(3-hydroxyphenyl)hexyl, 1,1-dimethyl-2-(2-hydroxyphenyl) ethyl, 2-methyl-3-(4-hydroxyphenyl)propyl, 2-(4-hydroxyphenyl)propyl, 2,5-dihydroxybenzyl, 2,3-dihydroxybenzyl, 2-(2,4-dihydroxyphenyl)ethyl, 2-(2,6-dihydroxyphenyl)ethyl, 3-(3,4-dihydroxyphenyl)propyl, 4-(3,5-dihydroxyphenyl)butyl, 5-(3,4-dihydroxyphenyl) pentyl, 6-(3,5-dihydroxyphenyl)hexyl, 2,4,5-trihydroxybenzyl, 2-(2,4,6-trihydroxyphenyl)ethyl, 3-(3,4,5-trihydroxyphenyl)propoxy, 2-nitrobenzyl, 3-nitrobenzyl, 4-nitrobenzyl, 2-(2-nitrophenyl)ethyl, 3-(3-nitrophenyl) propyl, 4-(4-nitrophenyl)butyl, 5-(4-nitrophenyl)pentyl, 6-(3-nitrophenyl)hexyl, 1,1-dimethyl-2-(2-nitrophenyl) ethyl, 2-methyl-3-(4-nitrophenyl)propyl, 2-(4-nitrophenyl) propyl, 2,5-dinitrobenzyl, 2,3-dinitrobenzyl, 2-(2,4-dinitrophenyl)ethyl, 2-(2,6-dinitrophenyl)ethyl, 3-(3,4-dinitrophenyl)propyl, 4-(3,5-dinitrophenyl)butyl, 5-(3,4-dinitrophenyl)pentyl, 6-(3,5-dinitrophenyl)hexyl, 2,4,5-trinitrobenzyl, 2-(2,4,6-trinitrophenyl)ethyl, 3-(3,4,5-trinitrophenyl)propoxy, 2-methylbenzyl, 3-ethylbenzyl, 4-propylbenzyl, 4-butoxybenzyl, 4-pentylbenzyl, 4-hexylbenzyl, 4-isopropylbenzyl, 4-tert-butylbenzyl, 2-(2-methylphenyl)ethyl, 1-(3-ethylphenyl)ethyl, 3-(4-ethylphenyl)propyl, 4-(4-propylphenyl)butyl, 5-(4-butylphenyl)pentyl, 6-(4-pentylphenyl)hexyl, 1,1-dimethyl-2-(2-methylphenyl)ethyl, 2-(3-ethylphenyl)propyl, 2,3-dimethylbenzyl, 2-(2,4-dimethylphenyl)ethyl, 3-(2,5-diethylphenyl)propyl, 4-(2,6-diethylphenyl)butyl, 5-(3,4-dimethylphenyl)pentyl, 6-(3,5-diethylphenyl)hexyl, 3,4,5-trimethylbenzyl, 2-(2,4,5-trimethylphenyl)ethyl, 3-(2,4,6-trimethylphenyl)propyl, 2-methoxybenzyl, 3-methoxybenzyl, 4-methoxybenzyl, 4-ethoxybenzyl, 4-propoxybenzyl, 4-isopropoxybenzyl, 4-butoxybenzyl, 4-tert-butoxybenzyl, 4-pentyloxybenzyl, 4-hexyloxybenzyl, 2,3-dimethoxybenzyl, 2,4-dimethoxybenzyl, 2,5-diethoxybenzyl, 2,6-diethoxybenzyl, 3,4-dimethoxybenzyl, 3,5-diethoxybenzyl, 2,3,4-trimethoxybenzyl, 2,3,5-trimethoxybenzyl, 2,3,6-triethoxybenzyl, 3,4,5-triethoxybenzyl, 2-(2-methoxyphenyl)ethyl, 1-(3-ethoxyphenyl)ethyl, 2-(4-methoxyphenyl)ethyl, 3-(4-ethoxyphenyl)propyl, 3-(4-propoxyphenyl)ethyl, 4-(4-butoxyphenyl)butyl, 1,1-dimethyl-2-(4-methoxyphenyl) ethyl, 5-(4-pentyloxyphenyl)pentyl, 6-(4-hexyloxyphenyl) hexyl, 2-(4-methoxyphenyl)propyl, 2-(2,4-dimethoxyphenyl)ethyl, 3-(3,4-diethoxyphenyl)propyl, 2-(2,4,5-trimethoxyphenyl)ethyl, 3-(3,4,5-triethoxyphenyl) propyl, 2-methylthiobenzyl, 3-(2-ethylthio)benzyl, 4-(3-propylthio)benzyl, 2-(2-methylthiophenyl)ethyl, 3-(3-methylthiophenyl)propyl, 4-(4-methylthiophenyl)butyl, 5-(4-methylthiophenyl)pentyl, 6-(3-methylthiophenyl) hexyl, 1,1-dimethyl-2-(2-methylthiophenyl)ethyl, 2-methyl-3-(4-methylthiophenyl)propyl, 2-(4-methylthiophenyl) propyl, 2,5-di(4-butylthio)benzyl, 2,3-dimethylthiobenzyl, 2-(2,4-dimethylthiophenyl)ethyl, 2-(2,6-dimethylthiophenyl)ethyl, 4-(3,5-dimethylthiophenyl)butyl, 5-(3,4-dimethylthiophenyl)pentyl, 6-(3,5-dimethylthiophenyl)hexyl, 2,4,5-tri(6-hexylthio)benzyl, 2-(2,4,6-trimethylthiophenyl)ethyl, 3-(3,4,5-trimethylthiophenyl)propoxy, and the like.

Examples of the phenyl group which may have from 1 to 3 substituents selected from a halogen atom, a hydroxyl group, a nitro group, a lower alkyl group, a lower alkoxy group and a lower alkylthio group include phenyl groups which may have from 1 to 3 substituents selected from a halogen atom, a hydroxyl group, a nitro group, a straight chain or branched alkyl group having from 1 to 6 carbon atoms, a straight chain or branched alkoxy group having from 1 to 6 carbon atoms and a straight chain or branched alkylthio group having from 1 to 6 carbon atoms, such as phenyl, 2-fluorophenyl, 3-fluorophenyl, 4-fluorophenyl, 2-chlorophenyl, 3-chlorophenyl, 4-chlorophenyl, 4-bromophenyl, 4-iodophenyl, 2,3-dichlorophenyl, 2,4-difluorophenyl, 2,5-dibromophenyl, 2,6-dichlorophenyl, 3,4-difluorophenyl, 3,5-dichlorophenyl, 2,3,5-trifluorophenyl, 3,4,5-trichlorophenyl, 2-hydroxyphenyl, 3-hydroxyphenyl, 4-hydroxyphenyl, 2,5-dihydroxyphenyl, 2,3-dihydroxyphenyl, 2,4,5-trihydroxyphenyl, 2-nitrophenyl, 3-nitrophenyl, 4-nitrophenyl, 2,3-dinitrophenyl, 2,4,5-trinitrophenyl, 2-methylphenyl, 3-methylphenyl, 4-methylphenyl, 3-ethylphenyl, 4-ethylphenyl, 4-propylphenyl, 4-pentylphenyl, 4-hexylphenyl, 4-butylphenyl, 4-isopropylphenyl, 4-tert-butylphenyl, 2,3-dimethylphenyl, 2,4-diethylphenyl, 2,5-dimethylphenyl, 2,6-dimethylphenyl, 3,4-dimethylphenyl, 3,5-diethylphenyl, 2,3,5-trimethylphenyl, 3,4,5-trimethylphenyl, 2-methoxyphenyl, 3-methoxyphenyl, 4-methoxyphenyl, 3-ethoxyphenyl, 4-ethoxyphenyl, 4-propoxyphenyl, 4-isopropoxyphenyl, 4-butoxyphenyl, 4-tert-butoxyphenyl, 4-pentyloxyphenyl, 4-hexyloxyphenyl, 2,3-dimethoxyphenyl, 2,4-diethoxyphenyl, 2,5-dimethylphenyl, 2,6-dimethoxyphenyl, 3,4-dimethoxyphenyl, 3,5-diethoxyphenyl, 2,3,5-trimethoxyphenyl, 3,4,5-trimethoxyphenyl, 2-methylthiophenyl, 3-ethylthiophenyl, 4-propylthiophenyl, 4-butylthiophenyl, 4-pentylthiophenyl, 4-hexylthiophenyl, 2,3-dimethylthiophenyl, 2,4-dimethylthiophenyl, 3,4-dimethylthiophenyl, 3,4,5-trimethylthiophenyl, and the like.

Examples of the lower alkanoylamino group, regardless of whether it exists independently or exists in other groups, include amino groups having a straight chain or branched alkanoyl group having from 1 to 6 carbon atoms, such as formylamino, acetylamino, propionylamino, butyrylamino, isobutyrylamino, pentanoylamino, tert-butylcarbonylamino, hexanoylamino, and the like.

Examples of the phenylsulfonylamino group which may have a substituent selected from a halogen atom, a hydroxyl group, an amino group and a lower alkanoylamino group on the phenyl ring thereof include phenylsulfonylamino, 2-fluorophenylsulfonylamino, 3-fluorophenylsulfonylamino, 4-fluorophenylsulfonylamino, 2-chlorophenylsulfonylamino, 3-chlorophenylsulfonylamino, 4-chlorophenylsulfonylamino, 4-bromophenylsulfonylamino, 4-iodophenylsulfonylamino, 2-hydroxyphenylsulfonylamino, 3-hydroxyphenylsulfonylamino, 4-hydroxyphenylsulfonylamino, 2-aminophenylsulfonylamino, 3-aminophenylsulfonylamino, 4-aminophenylsulfonylamino, 2-acetylaminophenylsulfonylamino, 3-acetylaminophenylsulfonylamino, 4-acetylaminophenylsulfonylamino, 2-butyrylaminophenylsulfonylamino, 3-butyrylaminophenylsulfonylamino, 4-butyrylaminophenylsulfonylamino, and the like.

Examples of the lower alkylidene group include straight chain or branched alkylidene groups having from 1 to 6 carbon atoms such as methylene, ethylidene, propylidene, isopropylidene, butylidene, tert-butylidene, pentylidene, hexylidene, and the like.

Examples of the lower alkylidene group having 1 or 2 lower cycloalkyl groups include straight chain or branched alkylidene groups having 1 to 6 carbon atoms and having 1 or 2 cycloalkyl groups having 3 to 8 carbon atoms, such as 2-cyclopropylethylidene, 1-cyclobutylethylidene, 3-cyclopentylpropylidene, 4-cyclohexylbutylidene, 1,1-dimethyl-2-cycloheptylethylidene, 5-cyclooctylpentylidene, 6-cyclohexylhexylidene, 2-methyl-3-cyclohexylpropylidene, dicyclopropylmethylene, 2-dicyclopropylethylidene, and the like.

Examples of the lower cycloalkylidene group include cycloalkylidene groups having from 3 to 8 carbon atoms such as cyclopropylidene, cyclobutylidene, cyclopentylidene, cyclohexylidene, cycloheptylidene, cyclooctylidene, and the like.

Examples of the diphenyl-lower alkylidene group include diphenyl alkylidene groups in which the alkylidene moiety is a straight chain or branched group having from 1 to 6 carbon atoms, such as 2,2-diphenylethylidene, 1,1-diphenylethylidene, 3,3-diphenylpropylidene, 4,4-diphenylbutylidene, 5,5-diphenylpentylidene, 6,6-diphenylhexylidene, and the like.

Examples of the phenyl-lower alkylidene group include phenylalkylidene groups in which the alkylidene moiety is a straight chain or branched group having from 1 to 6 carbon atoms, such as benzylidene, 2-phenylethylidene, 1-phenylethylidene, 3-phenylpropylidene, 4-phenylbutylidene, 1,1-dimethyl-2-phenylethylidene, 5-phenylpentylidene, 6-phenylhexylidene, 2-methyl-3-phenylpropylidene, 2-phenylpropylidene, and the like.

Examples of the lower alkenyl group include straight chain or branched alkenyl groups having from 2 to 6 carbon atoms, such as vinyl, allyl, 2-butenyl, 3-butenyl, 1-methylallyl, 2-pentenyl, 2-hexenyl, and the like.

Examples of the phenyl-lower alkoxy-lower alkyl group include phenylalkoxyalkyl groups in which the alkoxy moiety is a straight chain or branched group having from 1 to 6 carbon atoms and the alkyl moiety is a straight chain or branched group having from 1 to 6 carbon atoms, such as benzyloxymethyl, 2-phenylethoxymethyl, 1-phenylethoxymethyl, 3-phenylpropoxymethyl, 4-phenylbutoxymethyl, 1,1-dimethyl-2-phenylethoxymethyl, 5-phenylpentyloxymethyl, 6-phenylhexyloxymethyl, 2-benzyloxyethyl, 3-benzyloxypropyl, 4-benzyloxybutyl, 1,1-dimethyl-2-benzyloxyethyl, 5-benzyloxypentyl, 6-benzyloxyhexyl, 2-methyl-3-benzyloxypropyl, and the like.

Examples of the phenyl group which may have a hydroxyl group include 2-hydroxyphenyl, 3-hydroxyphenyl, 4-hydroxyphenyl, and the like.

Examples of the 5-membered or 6-membered unsaturated heterocyclic-lower alkyl group having 1 or 2 hetero atoms selected from a nitrogen atom and a sulfur atom (the heterocyclic ring may be condensed with a benzene ring and hydroxyl groups may be located as a substituent on either one or both of the heterocyclic ring and the benzene ring being condensed therewith) include straight chain or branched alkyl groups having from 1 to 6 carbon atoms which have a 5-membered or 6-membered unsaturated heterocyclic ring having 1 or 2 hetero atoms selected from a nitrogen atom and a sulfur atom, such as 2-pyridinylmethyl, 3-pyridinylmethyl, 4-pyridinylmethyl, 2-(3-pyridinyl)ethyl, 3-(3-pyridinyl)propyl, 4-(3-pyridinyl)butyl, 5-(3-pyridinyl)pentyl, 6-(3-piperidinyl)hexyl, 1-methyl-2-(3-pyridinyl)

propyl, 2-hydroxy-3-pyridinylmethyl, 4-hydroxy-3-pyridinylmethyl, 6-hydroxy-3-pyridinylmethyl, 2-thienylmethyl, 3-thienylmethyl, 2-(2-thienyl)ethyl, 3-(2-thienyl)propyl, 4-(2-thienyl)butyl, 5-(2-thienyl)pentyl, 6-(2-thienyl)hexyl, 1-methyl-2-(2-thienyl)propyl, 3-hydroxy-2-thienylmethyl, 5-hydroxy-2-thienylmethyl, 1-imidazolylmethyl, 2-imidazolylmethyl, 4-imidazolylmethyl, 5-imidazolylmethyl, 2-(4-imidazolyl)ethyl, 3-(4-imidazolyl)propyl, 4-(4-imidazolyl)butyl, 5-(4-imidazolyl)pentyl, 6-(4-imidazolyl)hexyl, 1-methyl-2-(4-imidazolyl)propyl, 2-hydroxy-4-imidazolylmethyl, 1-indolylmethyl, 3-indolylmethyl, 2-(3-indolyl)ethyl, 3-(3-indolyl)propyl, 4-(3-indolyl)butyl, 5-(3-indolyl)pentyl, 6-(3-indolyl)hexyl, 4-hydroxy-3-indolylmethyl, 2-hydroxy-3-indolylmethyl, 6-hydroxy-3-indolylmethyl, 2-pyrrolylmethyl, 5-pyrazolylmethyl, 2-pyrimidinylmethyl, 2-pyrazinylmethyl, 2-thiazolylmethyl, 2-quinolylmethyl, 2-benzoimidazolylmethyl, 3-benzothienylmethyl, and the like.

Examples of the lower alkylene group include straight chain or branched alkylene groups having from 1 to 6 carbon atoms, such as methylene, ethylene, triethylene, 2-methyltriethylene, 2,2-dimethyltrimethylene, 1-methyltrimethylene, methylmethylene, ethylmethylene, tetramethylene, pentamethylene, hexamethylene, and the like.

Examples of the phenyl-lower alkyl group include phenylalkyl groups in which the alkyl moiety is a straight chain or branched group having from 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-phenylpropyl, and the like.

Examples of the carboxy-lower alkyl group include carboxyalkyl groups in which the alkyl moiety is a straight chain or branched group having from 1 to 6 carbon atoms, such as carboxymethyl, 2-carboxyethyl, 1-carboxyethyl, 3-carboxypropyl, 4-carboxybutyl, 1,1-dimethyl-2-carboxyethyl, 5-carboxypentyl, 6-carboxyhexyl, 2-methyl-3-carboxypropyl, and the like.

Examples of the lower cycloalkyl group include cycloalkyl groups having from 3 to 8 carbon atoms such as cyclopropyl, cyclobutyl, cyclopentyl, cyclohexyl, cycloheptyl, cyclooctyl, and the like.

Examples of the lower alkoxycarbonyl group include alkoxycarbonyl groups in which the alkoxy moiety is straight chain or branched group having from 1 to 6 carbon atoms, such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

Examples of the phenyl-lower alkoxy group include phenylalkoxy groups in which the alkoxy moiety is a straight chain or branched group having from 1 to 6 carbon atoms, such as benzyloxy, 2-phenylethoxy, 3-phenylpropoxy, 1-phenylisopropoxy, 4-phenylbutoxy, 5-phenylpentyloxy, 6-phenylhexyloxy, 2-methyl-3-phenylpropoxy, and the like.

Examples of the halogenated lower alkyl group include straight chain or branched halogenated alkyl groups having from 1 to 3 halogen atoms and in which the alkyl moiety is a straight chain or branched group having from 1 to 6 carbon atoms, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 3-fluoropropyl, 4-chlorobutyl, 5-chloropentyl, 6-bromohexyl, 3-fluoro-2-methylpropyl, and the like.

Examples of the lower alkylenedioxy group include alkylenedioxy groups having from 1 to 3 carbon atoms, such as methylenedioxy, ethylenedioxy, trimethylenedioxy, and the like.

Examples of the phenyl group which may have from 1 to 3 substituents selected from a halogen atom, a hydroxyl group, a nitro group, a lower alkyl group, a lower alkoxy group, a lower alkylthio group, a carboxyl group, a lower alkoxycarbonyl group, a phenyl-lower alkoxy group, a lower alkylenedioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group and a 6-lower alkanoyloxy-2,5,7,8-tetramethyl-2-chromanylmethyloxy group include phenyl groups which may have from 1 to 3 substituents selected from a halogen atom, a hydroxyl group, a nitro group, a straight chain or branched alkyl group having from 1 to 6 carbon atoms, a straight chain or branched alkoxy group having from 1 to 6 carbon atoms, a straight chain or branched alkylthio group having from 1 to 6 carbon atoms, a carboxy group, an alkoxycarbonyl group in which the alkoxy moiety is a straight chain or branched alkoxy group having from 1 to 6 carbon atoms, a phenylalkoxy group in which the alkoxy moiety is a straight chain or branched group having from 1 to 6 carbon atoms, an alkylenedioxy group, a morpholino group, a halogenated alkyl group having from 1 to 3 halogen atoms in which the alkyl moiety is a straight chain or branched group having from 1 to 6 carbon atoms, a carboxyalkyl group in which the alkyl moiety is a straight chain or branched group having from 1 to 6 carbon atoms, an alkoxycarbonylalkyl group in which the alkoxy moiety has from 1 to 6 carbon atoms and the alkyl moiety has from 1 to 6 carbon atoms, a 6-hydroxy-2,5,7,8-tetramethyl-2-chromanylmethyloxy group and a 6-alkanoyloxy-2,5,7,8-tetramethyl-2-chromanylmethyloxy group in which the alkanoyloxy moiety is an alkanoyloxy group having from 1 to 6 carbon atoms, such as phenyl, 2-fluorophenyl, 3-fluorophenyl, 4-fluorophenyl, 2-chlorophenyl, 3-chlorophenyl, 4-chlorophenyl, 4-bromophenyl, 4-iodophenyl, 2,3-dichlorophenyl, 2,4-dichlorophenyl, 2,4-difluorophenyl, 2,5-dibromophenyl, 2,6-dichlorophenyl, 3,4-difluorophenyl, 3,5-dichlorophenyl, 2,3,5-trifluorophenyl, 3,4,5-trichlorophenyl, 2-hydroxyphenyl, 3-hydroxyphenyl, 4-hydroxyphenyl, 2-(2-hydroxy)phenyl, 3-(3-hydroxy)phenyl, 4-(4-hydroxy)phenyl, 5-(4-hydroxy)phenyl, 6-(3-hydroxy)phenyl, 1,1,-dimethyl-2-(2-hydroxy)phenyl, 2-methyl-3-(4-hydroxy)phenyl, 2-(4-hydroxy)phenyl, 2,5-dihydroxyphenyl, 2,3-dihydroxyphenyl, 2-(2,4-dihydroxy)phenyl, 2-(2,6-dihydroxy)phenyl, 3-(3,4-dihydroxy)phenyl, 4-(3,5-dihydroxy)phenyl, 5-(3,4-dihydroxy)phenyl, 6-(3,5-dihydroxy)phenyl, 2,4,5-trihydroxyphenyl, 2-(2,4,6-trihydroxy)phenyl, 3-(3,4,5-trihydroxy)phenyl, 2-nitrophenyl, 3-nitrophenyl, 4-nitrophenyl, 2-(2-nitro)phenyl, 3-(3-nitro)phenyl, 4-(4-nitro)phenyl, 5-(4-nitro)phenyl, 6-(3-nitro)phenyl, 1,1-dimethyl-2-(2-nitro)phenyl, 2-methyl-3-(4-nitro)phenyl, 2-(4-nitro)phenyl, 2,5-dinitrophenyl, 2,3-dinitrophenyl, 2-(2,4-dinitro)phenyl, 2-(2,6-dinitro)phenyl, 3-(3,4-dinitro)phenyl, 4-(3,5-dinitro)phenyl, 5-(3,4-dinitro)phenyl, 6-(3,5-dinitro)phenyl, 2,4,5-trinitrophenyl, 2-(2,4,6-trinitro)phenyl, 3-(3,4,5-trinitro)phenyl, 2-methylphenyl, 3-methylphenyl, 4-methylphenyl, 3-ethylphenyl, 4-ethylphenyl, 4-propylphenyl, 4-pentylphenyl, 4-hexylphenyl, 4-butylphenyl, 4-isopropylphenyl, 4-tert-butylphenyl, 2,3-dimethylphenyl, 2,4-diethylphenyl, 2,5-dimethylphenyl, 2,6-dimethylphenyl, 3,4-dimethylphenyl, 3,5-diethylphenyl, 2,3,5- trimethylphenyl, 3,4,5-trimethylphenyl, 2-methoxyphenyl, 3-methoxyphenyl, 4-methoxyphenyl, 3-ethoxyphenyl, 4-ethoxyphenyl, 4-propoxyphenyl, 4-isopropoxyphenyl, 4-butoxyphenyl, 4-tert-butoxyphenyl, 4-pentylphenyl, 4-hexylphenyl, 2,3-dimethoxyphenyl, 2,4-diethoxyphenyl, 2,5-dimethylphenyl, 2,6-dimethoxyphenyl, 3,4-dimethoxyphenyl, 3,5-diethoxyphenyl, 2,3,5-trimethoxyphenyl, 3,4,5-trimethoxyphenyl, 2-methylthiophenyl, 3-ethylthiophenyl, 4-propylthiophenyl, 4-butylthiophenyl, 4-pentylthiophenyl, 4-hexylthiophenyl, 2,3-dimethylthiophenyl, 2,4-dimethylthiophenyl, 2,6-dimethylthiophenyl, 2,4,6-trimethylthiophenyl, 2-carboxyphenyl, 3-carboxyphenyl, 4-carboxyphenyl, 2,3-dicarboxyphenyl, 3,4-dicarboxyphenyl, 2,4-dicarboxyphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 4-isopropoxycarbonylphenyl, 4-pentyloxycarbonylphenyl, 4-propoxycarbonylphenyl, 4-tert-butoxycarbonylphenyl, 4-hexyloxycarbonylphenyl, 3,4-dimethoxycarbonylphenyl, 2,4-dimethoxycarbonylphenyl, 2,3-dimethoxycarbonylphenyl, 3-methoxycarbonyl-4-ethoxycarbonylphenyl, 3,4-diethoxycarbonylphenyl, 2,4-diethoxycarbonylphenyl, 2,3-diethoxycarbonylphenyl, 2-benzyloxyphenyl, 3-benzyloxyphenyl, 4-benzyloxyphenyl, 2,4-dibenzylphenyl, 4,6-dibenzylphenyl, 4-(2-phenylethoxy)phenyl, 4-(3-phenylpropoxy)phenyl, 4-(4-phenylbutoxy)phenyl, 4-(5-phenylpentyloxy)phenyl, 4-(6-phenylhexyloxy)phenyl, 2,3-methylenedioxyphenyl, 3,4-methylenedioxyphenyl, 2,3-ethylenedioxyphenyl, 3,4-ethylenedioxyphenyl, 2,3-propylenedioxyphenyl, 3,4-propylenedioxyphenyl, 2-morpholinophenyl, 3-morpholinophenyl, 4-morpholinophenyl, 2-chloromethylphenyl, 3-bromomethylphenyl, 4-iodomethylphenyl, 2-fluoromethylphenyl, 2-dichloromethylphenyl, 4-dibromomethylphenyl, 3-difluoromethylphenyl, 3-trichloromethylphenyl, 3-trifluoromethylphenyl, 4-trifluoromethylphenyl, 4-(1,2-dichloroethyl)phenyl, 2-(3-fluoropropyl)phenyl, 3-(4-chlorobutyl)phenyl, 4-(5-chloropentyl)phenyl, 4-(6-bromohexyl)phenyl, 2-(2-chloroethyl)-4-dibromomethylphenyl, 2,3,4-tri(chloromethyl)phenyl, 2-carboxymethylphenyl, 3-carboxymethylphenyl, 4-carboxymethylphenyl, 3,5-di(carboxymethyl)phenyl, 4-(2-carboxyethyl)phenyl, 3-(4-carboxybutyl)phenyl, 4-(6-carboxyhexyl)phenyl, 2-methoxycarbonylmethylphenyl, 3-methoxycarbonylmethylphenyl, 4-methoxycarbonylmethylphenyl, 2,6-di(methoxycarbonylmethyl)phenyl, 4-ethoxycarbonylmethylphenyl, 3-butoxycarbonylmethylphenyl, 4-(4-ethoxycarbonylbutyl)phenyl, 3-(6-hexyloxycarbonylhexyl)phenyl, 3-(6-hydroxy-2,5,7,8-tetramethylchroman-2-yl)methoxyphenyl, 4-(6-hydroxy-2,5,7,8-tetramethylchroman-2-yl)methoxyphenyl, 3-(6-propionyloxy-2,5,7,8-tetramethylchroman-2-yl)methoxyphenyl, 4-(6-hexanoyloxy-2,5,7,8-tetramethylchroman-2-yl)methoxyphenyl, 4-(6-acetoxy-2,5,7,8-tetramethylchroman-2-yl)methoxyphenyl, 2-carboxy-4-methylphenyl, 3-carboxy-6-methylphenyl, 4-carboxy-6-methylphenyl, 2-carboxy-4-ethylphenyl, 2-carboxy-4-chlorophenyl, 3-carboxy-6-bromophenyl, 4-carboxy-6-chlorophenyl, 2-carboxy-4-bromophenyl, 2-methoxycarbonyl-5-methylphenyl, 3-methoxycarbonyl-6-methylphenyl, 2-methoxycarbonyl-4-ethylphenyl, 4-ethoxycarbonyl-6-methylphenyl, 2-methoxycarbonyl-6-chlorophenyl, 3-methyl-5-fluorophenyl, 2-carboxy-3-fluoro-4-methylphenyl, 2-carboxy-4-methyl-6-methoxyphenyl, and the like.

Examples of the 5-membered or 6-membered unsaturated heterocyclic-lower alkyl group having 1 or 2 hetero atoms selected from a nitrogen atom, oxygen atom and a sulfur atom include unsaturated heterocyclic-lower alkyl groups in which the alkyl moiety has from 1 to 6 carbon atoms, such as 2-pyridinylmethyl, 3-pyridinylmethyl, 4-pyridinylmethyl, 2-(3-pyridinyl)ethyl, 3-(3-pyridinyl)propyl, 4-(3-pyridinyl)butyl, 5-(3-pyridinyl)pentyl, 6-(3-pyridinyl)hexyl, 1-methyl-2-(3-pyridinyl)propyl, 2-thienylmethyl, 3-thienylmethyl, 4-thienylmethyl, 2-(2-thienyl)ethyl, 3-(2-thienyl)propyl, 4-(2-thienyl)butyl, 5-(2-thienyl)pentyl, 6-(2-thienyl)hexyl, 1-methyl-2-(2-thienyl)propyl, 1-imidazolylmethyl, 2-imidazolylmethyl, 4-imidazolylmethyl, 5-imidazolylmethyl, 2-(1-imidazolyl)ethyl, 3-(4-imidazolyl)propyl, 4-(4-imidazolyl)butyl, 5-(4-imidazolyl)pentyl, 6-(4-imidazolyl)hexyl, 1-methyl-2-(1-imidazolyl)propyl, 2-pyrrolylmethyl, 2-pyrimidinylmethyl, 2-pyrazinylmethyl, 2-thiazolyl methyl, 2-furylmethyl, 3-furylmethyl, 2-(2-furyl)ethyl, 3-(3-furyl)propyl, 4-(2-furyl)butyl, 5-(3-furyl)pentyl, 6-(2-furyl)hexyl, and the like.

Examples of the phenylthio group which may have a halogen atom include 2-chlorophenylthio, 3-chlorophenylthio, 4-chlorophenylthio, 2-bromophenylthio, 4-bromophenylthio, 3-fluorophenylthio, 4-fluorophenylthio, 4-iodophenylthio, and the like.

Examples of the phenyl-lower alkylthio group include phenylalkylthio groups in which the alkyl moiety is a straight chain or branched group having from 1 to 6 carbon atoms, such as benzylthio, 2-phenylethylthio, 1-phenylethylthio, 3-phenylpropylthio, 4-phenylbutylthio, 1,1-dimethyl-2-phenylethylthio, 5-phenylpentylthio, 6-phenylhexylthio, 2-methyl-3-phenylpropylthio, 2-phenylpropylthio, and the like.

Examples of the benzoylamino group which may have from 1 to 3 halogen atoms include benzoylamino groups which may have from 1 to 3 halogen atoms, such as benzoylamino, 2-fluorobenzoylamino, 3-fluorobenzoylamino, 4-flurobenzoylamino, 2-chlorobenzoylamino, 3-chlorobenzoylamino, 4-chlorobenzoylamino, 4-bromobenzoylamino, 4-iodobenzoylamino, 2,3-dichlorobenzoylamino, 3,4-dichlorobenzoylamino, 2,4-dichlorobenzoylamino, 3,4,5-trichlorobenzoylamino, and the like.

Examples of the phenyl group which may have from 1 to 3 substituents selected from a halogen atom, a hydroxyl group, a nitro group, a lower alkyl group, a lower alkoxy group and a lower alkylthio group on the phenyl ring thereof (the phenyl ring may be condensed with a benzene ring or a cyclohexane ring) include phenyl, 2-fluorophenyl, 3-fluorophenyl, 4-fluorophenyl, 2-chlorophenyl, 3-chlorophenyl, 4-chlorophenyl, 4-bromophenyl, 4-iodophenyl, 2,3-dichlorophenyl, 2,4-difluorophenyl, 2,5-dibromophenyl, 2,6-dichlorophenyl, 3,4-difluorophenyl, 3,5-dichlorophenyl, 2,3,5-trifluorophenyl, 3,4,5-trichlorophenyl, 2-hydroxyphenyl, 3-hydroxyphenyl, 4-hydroxyphenyl, 2-(2-hydroxy)phenyl, 3-(3-hydroxy)phenyl, 4-(4-hydroxy)phenyl, 5-(4-hydroxy)phenyl, 6-(3-hydroxy)phenyl, 1,1-dimethyl-2-(2-hydroxy)phenyl, 2-methyl-3-(4-hydroxy)phenyl, 2-(4-hydroxy)phenyl, 2,5-dihydroxyphenyl, 2,3-dihydroxyphenyl, 2-(2,4-dihydroxy)phenyl, 2-(2,6-dihydroxy)phenyl, 3-(3,4-dihydroxy)phenyl, 4-(3,5-dihydroxy)phenyl, 5-(3,4-dihydroxy)phenyl, 6-(3,5-dihydroxy)phenyl, 2,4,5-trihydroxyphenyl, 2-(2,4,6-trihydroxy)phenyl, 3-(3,4,5-trihydroxy)phenyl, 2-nitrophenyl, 3-nitrophenyl, 4-nitrophenyl, 2-(2-nitro) phenyl, 3-(3-nitro)phenyl, 4-(4-nitro)phenyl, 5-(4-nitro) phenyl, 6-(3-nitro)phenyl, 1,1-dimethyl-2-(2-nitro)phenyl, 2-methyl-3-(4-nitro)phenyl, 2-(4-nitro)phenyl, 2,5-dinitrophenyl, 2,3-dinitrophenyl, 2-(2,4-dinitro)phenyl, 2-(2,6-dinitro)phenyl, 3-(3,4-dinitro)phenyl, 4-(3,5-dinitro) phenyl, 5-(3,4-dinitro)phenyl, 6-(3,5-dinitro)phenyl, 2,4,5-trinitrophenyl, 2-(2,4,6-trinitro)phenyl, 3-(3,4,5-trinitro) phenyl, 2-methylphenyl, 3-methylphenyl, 4-methylphenyl, 3-ethylphenyl, 4-ethylphenyl, 4-propylphenyl, 4-pentylphenyl, 4-hexylphenyl, 4-butylphenyl, 4-isopropylphenyl, 4-tert-butylphenyl, 2,3-dimethylphenyl, 2,4-diethylphenyl, 2,5-dimethylphenyl, 2,6-dimethylphenyl, 3,4-dimethylphenyl, 3,5-diethylphenyl, 2,3,5-trimethylphenyl, 3,4,5-trimethylphenyl, 2-methoxyphenyl, 3-methoxyphenyl, 4-methoxyphenyl, 3-ethoxyphenyl, 4-ethoxyphenyl, 4-propoxyphenyl, 4-isopropoxyphenyl, 4-butoxyphenyl, 4-tert-butoxyphenyl, 4-pentylphenyl, 4-hexylphenyl, 2,3-dimethoxyphenyl, 2,4-diethoxyphenyl, 2,5-dimethylphenyl, 2,6-dimethoxyphenyl, 3,4-dimethoxyphenyl, 3,5-diethoxyphenyl, 2,3,5-trimethoxyphenyl, 3,4,5-trimethoxyphenyl, 2-methylthiophenyl, 3-ethylthiophenyl, 4-propylthiophenyl, 4-butylthiophenyl, 4-pentylthiophenyl, 4-hexylthiophenyl, 2,3-dimethylthiophenyl, 2,4-dimethylthiophenyl, 2,6-dimethylthiophenyl, 2,4,6-trimethylthiophenyl, 1-naphthyl, 2-naphthyl, 5,6,7,8-tetrahydro-1-naphthyl, 5,6,7,8-tetrahydro-2-naphthyl, and the like.

Examples of the 5-membered or 6-membered, saturated or unsaturated heterocyclic ring group having a hetero atom selected from a nitrogen atom, a sulfur atom and an oxygen atom (the heterocyclic ring may be condensed with a benzene ring and 1 to 5 substituents selected from a hydroxyl group and a lower alkyl group may be located on the heterocyclic ring or the benzene ring being condensed with the heterocyclic ring) include 2-pyrrolyl, 3-pyrrolyl, 2-thienyl, 2-furanyl, 3-furanyl, 2-pyridinyl, 3-pyridinyl, 4-pyridinyl, 2-pyrrolidinyl, 3-pyrrolidinyl, 2-tetrahydrothionyl, 2-tetrahydrofuranyl, 3-piperidinyl, 2-tetrahydrothiopyranyl, 2-tetrahydropyranyl, 3-indolyl, 2-dihydrobenzopyranyl, 3-dihydrobenzopyranyl, 5-methyl-2-pyrrolyl, 5-methyl-2-thienyl, 5-methyl-2-pyridinyl, 3,5-dimethyl-2-pyridinyl, 4,6-dihydroxy-2-pyridinyl, 6,8-dihydroxy-2-dihydrobenzopyranyl, 6-hydroxy-2,5,7-trimethyl-2-dihydrobenzopyranyl, and the like.

Examples of the phenylcarbamoyl-lower alkyl group which may have 1 or 2 lower alkoxy groups on the phenyl ring thereof include phenylcarbamoylalkyl groups which may have 1 or 2 alkoxy groups on the phenyl ring thereof in which the alkoxy moiety has from 1 to 6 carbon atoms and the alkyl moiety has from 1 to 6 carbon atoms, such as phenylcarbamoylmethyl, phenylcarbamoylethyl, phenylcarbamoylpropyl, phenylcarbamoylbutyl, phenylcarbamoylpentyl, phenylcarbamoylhexyl, 2-metoxyphenylcarbamoylmethyl, 3-methoxyphenylcarbamoylmethyl, 4-methoxyphenylcarbamoylmethyl, 4-ethoxyphenylcarbamoylmethyl, 4-butoxyphenylcarbamoylmethyl, 4-propoxyphenylcarbamoylmethyl, 2-ethoxy-4-butoxyphenylcarbamoylmethyl, 4-pentyloxyphenylcarbamoylmethyl, 4-hexyloxyphenylcarmaboylmethyl, 2,6-dimethoxyphenylcarbamoylmethyl, 2-(2,4-dimethoxyphenylcarbamoyl)ethyl.

Abbreviations of amino acids, etc. as used herein are expressed in accordance with the specification of IUPAC and IUB or those commonly employed in the art, for example, Tyr means tyrosine, Leu means leucine, Trp means tryptophan, Asp means aspattic acid and Ph-Gly means phenylglycine.

When $R^1$ is a hydrogen atom and A is a carbonyl group in the compound of the general formula (1), the compound may have the following isomer structures (1A) to (1E).

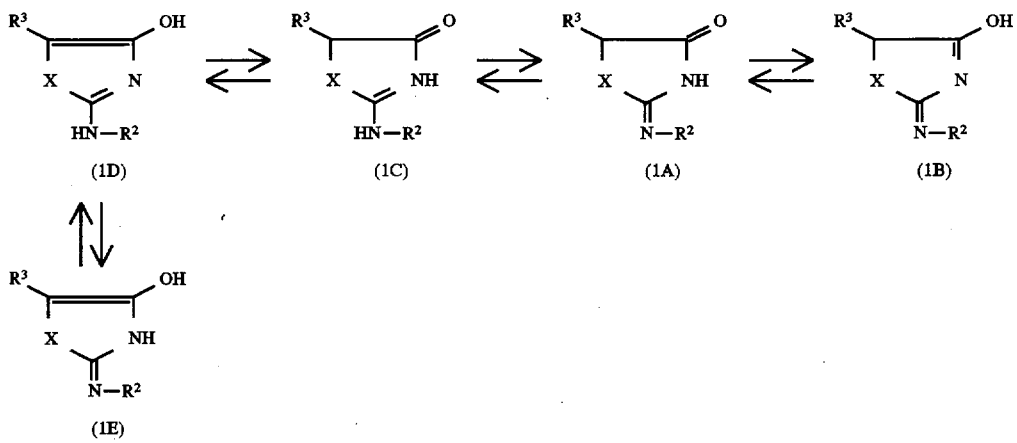

The compound of the general formula (1) includes within its scope all of these isomers as well as other stereoisomers, optical isomers, and geometrical isomers.

The compounds represented by the general formula (1) partially include known compounds, but most of these compounds are novel ones.

The compounds of the general formula (1) can be produced by various methods such as, for example, by the methods shown in the following reaction steps.

Reaction Step 1:

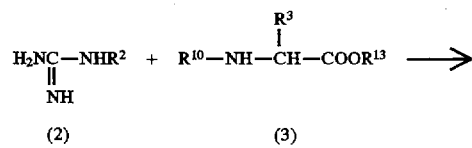

Reaction Step 1:

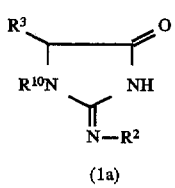

(1a)

In the above formulae, $R^1$, $R^2$, $R^3$ and $R^{10}$ have the same meaning as described above, and $R^{13}$ represents a usual ester residue.

Examples of the ester residue represented by $R^{13}$ include a lower alkyl group having from 1 to 6 carbon atoms and a phenyl-lower alkyl group.

The reaction between the compound of the general formula (2) or the acid addition salt thereof and the compound of the general formula (3) or the acid addition salt thereof is carried out in a suitable solvent in the presence or absence of a deoxidizing agent at a temperature of from about room temperature to 200° C., preferably from about 60° to 100° C. Examples of the acid addition salt include hydrochloride and sulfate. Examples of the deoxidizing agent include alkali metal alcholates such as sodium methoxide and sodium ethoxide, and basic compounds such as potassium carbonate, sodium carbonate, sodium hydroxide, sodium hydrogencarbonate, triethylamine, tripropylamine, pyridine, quinoline, 4-dimethylaminopyridine and sodium acetate. Solvents suitable for the above reaction are lower alcohols such as methanol, ethanol and isopropanol, ethers such as dioxane, tetrahydrofuran, ethylene glycol dimethyl ether and diethyl ether, aromatic hydrocarbons such as benzene, toluene and xylene, tertiary amines such as triethylamine and tripropylamine and polar solvents such as dimethylformamide and dimethylsulfoxide. The amount of the compound represented by the general formula (3) or the acid addition salt thereof is suitably at least an equimolar amount to the compound represented by the general formula (2) or the acid addition salt thereof, and is preferably from about 1 to 3 molar times as much as the latter compound. The above-mentioned reaction smoothly proceeds at a temperature of from about 15° to 200° C., and preferably from about 60° to 100° C., and is generally completed within about 1 to 24 hours.

Reaction Step 2:

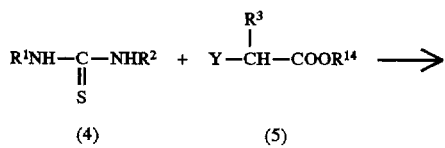

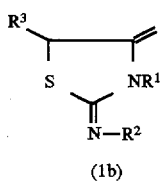

(1b)

In the above formulae, $R^1$, $R^2$ and $R^3$ have the same meaning as described above, $R^{14}$ represents a usual ester residue, and Y represents a halogen atom or a lower alkanesulfonyloxy group.

Examples of the ester residue represented by $R^{14}$ include a lower alkyl group having from 1 to 6 carbon atoms and a phenyl-lower alkyl group.

Examples of the lower alkanesulfonyloxy group include, for example, alkanesulfonyl groups such as methanesulfonyloxy and ethanesulfonyloxy.

The reaction between the compound of the general formula (4) and the compound of the general formula (5) is carried out by using a common solvent in the presence of a deoxidizing agent. As the deoxidizing agent, any of those cited as the deoxidizing agent to be used in the reaction between the compound (2) and the compound (3) in the above reaction step 1 may be used. As the solvent, commonly employed ones are usable over a wide range, and any of the solvents usable in the reaction between the compound (2) and the compound (3) in the above reaction step 1 may be used therefor. The reaction temperature may be from room temperature to about 150° C., and preferably from about 50° to 100° C. The amount of the compound represented by the general formula (5) is suitably at least an equimolar amount to the compound represented by the general formula (4), and is preferably from about 1 to 3 molar times as much as the latter compound. The amount of the deoxidizing agent is suitably at least 1 to 10 molar times as much as the compound shown by the general formula (4), and preferably from about 1 to 3 molar times as much as the latter compound. The reaction time usually ranges from about 1 to 36 hours.

Reaction Step 3:

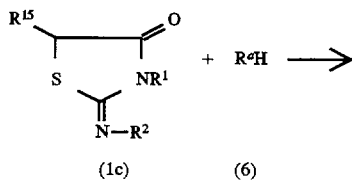

(1c)    (6)

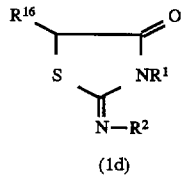

(1d)

In the above formulae, $R^1$, $R^2$ and $R^a$ have the same meaning as described above, $R^{15}$ represents —Z—COOH, and $R^{16}$ represents —Z—CO—$R^a$ wherein Z has the same meaning as described above.

By the reaction shown by the reaction step 3, the amine compound represented by the general formula (6) is reacted with the carboxylic acid represented by the general formula (1c) by a conventional amido bond-forming reaction. Known conditions for the amido bond-forming reactions can easily be applied to this amido bond-forming reaction. Examples of these methods include:

(a) a mixed acid anhydride method which comprises reacting the carboxylic acid (1c) with an alkylhalocarboxylic acid to give thereby a mixed acid anhydride and then reacting this product with the amine (6);

(b) an active ester method which comprises converting the carboxylic acid (1c) into an active ester, such as p-nitrophenyl ester, N-hydroxysuccinimide ester, or 1-hydroxybenzotriazole ester and then reacting with the amine (6);

(c) a carbodiimide method which comprises condensing the carboxylic acid (1c) with the amine (6) in the presence of an activating agent such as dicyclohexylcarbodiimide, water-soluble carbodiimide or carbonyl diimidazole; and (d) other methods, for example, the one which comprises converting the carboxylic acid (1c) into a carboxylic anhydride with a dehydrating agent such as acetic anhydride and then reacting with the amine (6), the one which comprises reacting an ester of the carboxylic acid (1c) with a lower alcohol or a phenyl-lower alcohol with the amine (6) at a high temperature under a high pressure, or another one which comprises reacting a halogenated carboxylic acid (1c), i.e., a carboxylic acid halide with the amine (6).

The mixed acid anhydride to be used in the above mixed acid anhydride method (a) can be obtained by a usual Schotten-Baumann reaction. It may be usually reacted with the amine (6) without isolation and thus the compound of the general formula (1d) can be produced. This Schotten-Baumann reaction is carried out in the presence of a basic compound. Examples of the basic compound to be used here include those conventionally employed in the Schotten-Baumann reaction, such as organic bases (e.g., triethylamine, trimethylamine, pyridine, dimethylaniline, N-methylmorpholine, 1,5-diazobicyclo[4.3.0]nonene-5 (DBN), 1,8-diazabicyclo[5.4.0]-undecene-7(DBU), and 1,4-diazabicyclo[2.2.2]octane(DABCO)), and inorganic bases (e.g., potassium carbonate, sodium carbonate, potassium hydrogencarbonate, and sodium hydrogencarbonate). This reaction is usually carried out at a temperature of from about $-20°$ to $100°$ C., and preferably at from about 0 to $50°$ C. The reaction time ranges from 5 minutes to 10 hours, and preferably from 5 minutes to 2 hours. The reaction between the mixed acid anhydride thus obtained and the amine (6) is usually carried out at a temperature of from about $-20°$ to $150°$ C., and preferably from about $10°$ to $50°$ C. The reaction time ranges from 5 minutes to 10 hours, and preferably from 5 minutes to 5 hours. The mixed acid anhydride method is usually carried out in a solvent. As the solvent, any solvent conventionally used for mixed acid anhydrides may be used. Specific examples of the solvent include halogenated hydrocarbons such as chloroform, dichloromethane and dichloroethane, aromatic hydrocarbons such as benzene, toluene and xylene, ethers such as diethyl ether, diisopropyl ether, tetrahydrofuran and dimethoxyethane, esters such as methyl acetate and ethyl acetate, aprotic polar solvents such as N,N-dimethylformamide, dimethylsulfoxide, acetonitrile and hexamethylphosphoric triamide, and mixtures of these solvents. Examples of the alkyl halocarboxylic acid to be used in the mixed acid anhydride method include methyl chloroformate, methyl bromoformate, ethyl chloroformate, ethyl bromoformate, and isobutyl chloroformate. In this method, the carboxylic acid (1c) is usually used in an equimolar amount to the alkyl halocarboxylic acid and the amine (6), though the alkyl halocarboxylic acid and the carboxylic acid (1c) may be used each in an amount of from 1 to 1.5 molar times as much as the amine (6).

Among the above-mentioned other methods (d), the reaction between the carboxylic acid halide with the amine (6) may be carried out in a suitable solvent in the presence of a basic compound. As the basic compound, publicly known compounds may be used over a wide range. Examples of the basic compound include basic compounds to be used in the above-mentioned Shotten-Baumann reaction as well as sodium hydroxide, potassium hydroxide, sodium hydride and potassium hydride. Examples of the solvent include the solvents to be used in the above mixed acid anhydride method as well as alcohols such as methanol, ethanol, propanol, butanol, 3-methoxy-1-butanol, ethylcellosolve and methylcellosolve, pyridine, acetone and water. The ratio of the amine (6) to the carboxylic acid halide is not particularly restricted but selected over a wide range. Usually, the former compound is used at least in an equimolar amount to the latter compound, and preferably from 1 to 5 molar times as much as the latter. This reaction is carried out at a temperature of from about $-20°$ to $180°$ C., and preferably from about $0°$ to $150°$ C. It is completed within 5 minutes to 30 hours in general.

Also, the amido bond-forming reaction shown by the above reaction step 3 may be carried out by reacting the carboxylic acid (1c) with the amine (6) in the presence of a condensing agent of a phosphorus compound such as triphenylphosphine, diphenylphosphinyl chloride, phenyl-N-phenylphosphoramide chloridate, diethyl chlorophosphate, diethyl cyanophosphate, diphenyl phosphoric azide, and bis(2-oxo-3-oxazolidinyl)phosphonic chloride.

This reaction is carried out in a solvent in the presence of a basic compound, each being the same as the one used in the above reaction between the carboxylic acid halide with the amine (6), usually at a temperature of from about $-20°$ to $150°$ C., and preferably from about $0°$ to $100°$ C. This reaction is completed usually within 5 minutes to 30 hours. It is preferable that the condensing agent and the carboxylic acid (1c) are each used in an amount at least equimolar to the amine (6), and preferably 1 to 2 molar times as much as the amine. It is preferable that the carboxyl groups in the above carboxylic acid (1c) and the amine (6), other than those which undergo the reaction, are protected.

Reaction step 4:

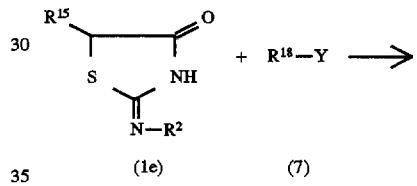 + $R^{18}$—Y $\longrightarrow$ (1e)    (7)

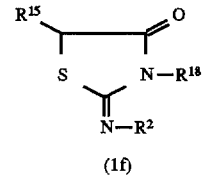

(1f)

In the above formulae, $R^2$ and $R^{15}$ have the same meaning as described above, and $R^{18}$ represents a lower alkoxycarbonyl-lower alkyl group or a phenyl-lower alkyl group which may have from 1 to 3 substituents selected from a halogen atom, a hydroxyl group, a nitro group, a lower alkyl group, a lower alkoxy group and a lower alkylthio group on the phenyl ring thereof.

The reaction between the compound of the general formula (1e) and the compound of the general formula (7) is carried out in a suitable solvent in the presence of a deoxidizing agent. As the deoxidizing agent, any of the deoxidizing agents to be used in the reaction between the compound (2) and the compound (3) in the above reaction step 1 may be used. As the solvent, conventional ones may be used over a wide range. For example, any solvent to be used in the reaction between the compound (2) and the compound (3) in the above reaction step 1 may be used. The ratio of the compound of the general formula (1e) to the compound of the general formula (7) is not particularly restricted but appropriately selected over a wide range. In usual, it is preferable to use the latter compound at least in an equimolar amount to the former, and preferably from 1 to 3 molar times as much as the former. This reaction smoothly proceeds at a temperature of from about $15°$ to $200°$ C., and preferably from about 30° to 80° C. It is usually completed within about 1 to 24 hours.

The compound of the present invention containing a carboxyl group can be obtained by hydrolyzing the ester corresponding thereto in a conventional manner. The following reaction is given by way of example.

Reaction Step 5:

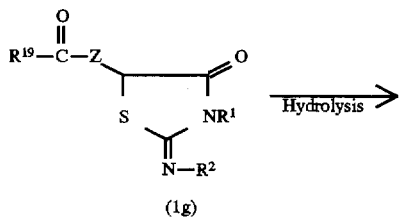

In the above formulae, $R^1$, $R^2$ and Z have the same meaning as described above, $R^{19}$ represents a group having an ester residue among the ones defined by $R^a$, and $R^{20}$ represents a group having a carboxyl residue among the ones defined by $R^a$.

The compound of the general formula (1b) is produced by hydrolyzing the compound of the general formula (1g) in a suitable solvent in the presence of an alkali. Examples of the alkali include sodium hydroxide and potassium hydroxide. As the solvent, conventional ones may be used over a wide rage. Examples thereof include methanol, ethanol, dioxane, tetrahydrofuran and water. The alkali is suitably used in an amount of 1 to 3 molar times as much as the compound of the general formula (1g). This hydrolysis smoothly proceeds usually at a temperature of from about 15° to 200° C., and preferably from about 30° to 60° C. It is generally completed within 1 to 24 hours.

Reaction Step 6:

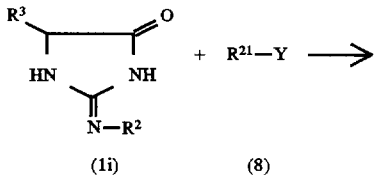

In the above formulae, $R^2$ and $R^3$ have the same meaning as described above, and $R^{21}$ represents a lower alkoxycarbonyl-lower alkyl group or a phenyl-lower alkyl group which may have from 1 to 3 substituents selected from a halogen atom, a lower alkyl group and a lower alkoxy group on the phenyl ring thereof.

The reaction between the compound of the general formula (1i) and the compound of the general formula (8) is carried out in a suitable solvent in the presence of a deoxidizing agent. As the deoxidizing agent, any of the deoxidizing agents to be used in the reaction between the compound (2) and the compound (3) in the above reaction step 1 may be used. The solvent may be selected from common ones over a wide range. For example, any of the solvents to be used in the reaction between the compound (2) and the compound (3) in the above reaction step 1 may be used. The ratio of the compound of the general formula (1i) to the compound of the general formula (8) is not particularly restricted but appropriately selected over a wide range. In usual, the latter compound is preferably used at least in an equimolar amount to, and preferably from 1 to 3 molar times as much as the former compound. This reaction smoothly proceeds at a temperature of from about 15° to 200° C., and preferably from about 60° to 100° C. It is generally completed within about 1 to 24 hours.

Reaction Step 7:

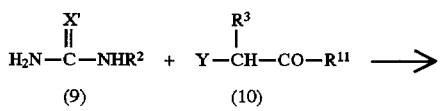

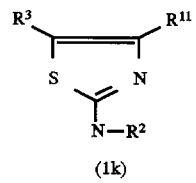

In the above formulae, $R^2$, $R^3$, $R^{11}$ and Y have the same meaning as described above, and =X' represents =S or =NH.

The reaction between the compound of the general formula (9) and the compound of the general formula (10) is carried out in a suitable solvent in the presence of a deoxidizing agent. As the deoxidizing agent, any of the deoxidizing agents to be used in the reaction between the compound (2) and the compound (3) in the above reaction step 1 may be used. The solvent may be selected from common ones over a wide range. For example, any of the solvents to be used in the reaction between the compound (2) and the compound (3) in the above reaction step 1 may be used. The ratio of the compound of the general formula (9) to the compound of the general formula (10) is not particularly restricted but appropriately selected over a wide range. In usual, the latter compound is preferably used at least in an equimolar amount to, and preferably from 1 to 3 molar times as much as the former compound- This reaction smoothly proceeds at a temperature of from about 15° to 200° C., and preferably from about 60° to 100° C. It is generally completed within about 1 to 24 hours.

Reaction Step 8:

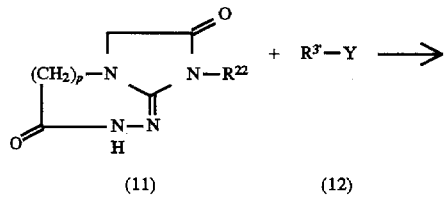

Reaction Step 8:

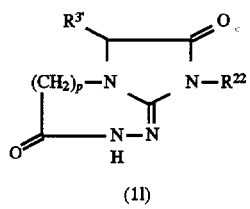

In the above formulae, $R^1$ and Y have the same meaning as described above, $R^{3'}$ has the same meaning as $R^3$ except for a hydrogen atom, $R^{22}$ represents a lower alkoxycarbonyl-lower alkyl group, a phenyl-lower alkyl group which may have from 1 to 3 substituents selected from a halogen atom, a lower alkyl group and a lower alkoxy group on the phenyl ring thereof or a phenyl group which may have from 1 to 3 substituents selected from a halogen atom, a lower alkyl group and a lower alkoxy group, and p is an integer of from 1 to 3.

The reaction between the compound of the general formula (11) and the compound of the general formula (12) is carried out in a suitable solvent in the presence of a strongly basic compound. Examples of the strongly basic compound include alkyl lithium compounds such as butyl lithium and t-butyl lithium. The solvent may be selected from conventional ones over a wide range. Examples thereof include ethers such as tetrahydrofuran, dioxane and diethyl ether, hydrocarbons such as hexane and hexamethylphosphoric triamide. Regarding the ratio of the compound of the general formula (11) to the compound of the general formula (12), the latter compound is preferably used at least in an equimolar amount to, and preferably from 1 to 3 molar times as much as the former compound. This reaction smoothly proceeds at a temperature of from about −70° to 15° C., and preferably from about −70° to −30° C. It is generally completed within about 1 to 24 hours.

Reaction Step 9:

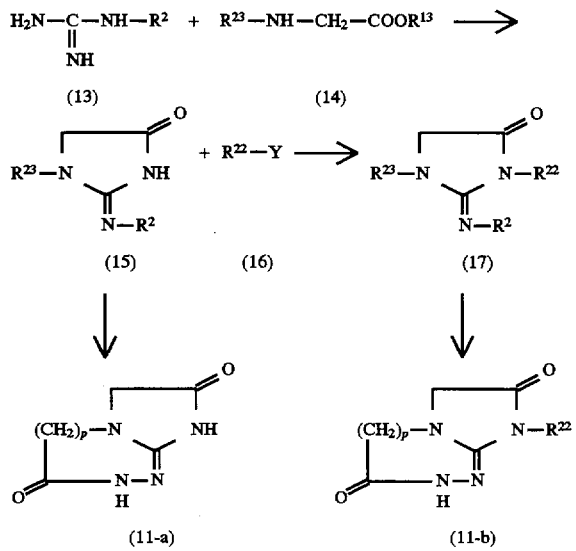

In the above formulae, $R^2$, $R^{13}$, $R^{22}$, Y and p have the same meaning as described above, and $R^{23}$ represents a lower alkoxycarbonyl-lower alkyl group.

The reaction between the compound of the general formula (13) and the compound of the general formula (14) is carried out under the same reaction conditions as those employed in the reaction between the compound (2) and the compound (3) in the above reaction step 1.

The reaction between the compound of the general formula (15) and the compound of the general formula (16) is carried out under the same reaction conditions as those employed in the reaction between the compound (1i) and the compound (8) in the above reaction step 6.

The reaction whereby the compound of the general formula (11) is obtained from the compound of the general formula (17) is carried out in the presence of an organic or inorganic, acidic compound. As the organic or inorganic, acidic compound, hydrochloric acid, sulfuric acid, trifluoroacetic acid, acetic acid or formic acid may be used. Among these compounds, diluted strong acids such as hydrochloric acid and sulfuric acid are particularly preferable. As the solvent, conventional solvents which are stable to acids may be used. Examples thereof include methanol, ethanol, dioxane, tetrahydrofuran and water. The acidic compound is generally used in an amount of from 1 to 20 molar times as much as the compound of the general formula (17). This reaction is carried out usually at a temperature of from about 30° to 120° C. for about 5 to 60 minutes.

The compound of the general formula (5), which is used as the starting material in the above reaction step 2, wherein $R^3$ is $R^6$NHCOZ— and Y is a lower alkanesulfonyloxy group may be produced by, for example, the following method.

Reaction Step 10:

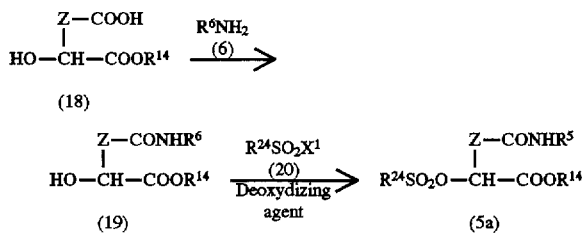

In the above formulae, $R^6$, $R^{14}$ and Z have the same meaning as described above, $R^{24}$ represents a lower alkyl group, and $X^1$ represents a halogen atom.

The reaction between the compound of the general formula (18) and the compound of the general formula (6) is carried out in a suitable solvent. Examples of the solvent include water, ethers such as tetrahydrofuran and dioxane, dimethylformamide and mixtures of these solvents. This reaction is carried out usually at a temperature of from about −10° to 40° C., and preferably at around room temperature. This reaction is usually completed within about 5 minutes to 1 hour.

The reaction between the compound of the general formula (19) and the compound of the general formula (20) is carried out in a suitable solvent in the presence of a deoxidizing agent. Examples of the solvent include halogenated hydrocarbons such as dichloromethane, chloroform and carbon tetrachloride, aromatic hydrocarbons such as benzene and toluene, ethers such as dioxane, tetrahydrofuran and diethyl ether, and mixtures of these solvents. As the deoxidizing agent, any of the deoxidizing agents to be used in the reaction between the compound (2) and the compound (3) in the above reaction step 1 may be used. This reaction is carried out usually at a temperature of from about −20° to 30° C., and preferably from −5° to 10° C. This reaction is usually completed within about 10 to 30 minutes. When the starting material (18) in this reaction is an optically active compound, the corresponding product (5a) can be obtained as an optically active compound, too.

The compounds of the general formula (1) include pharmaceutically acceptable addition salts thereof formed with acids or basic compounds. These salts can be easily formed by reacting an acid or a base with the compound of the present invention. The acids used for forming the salt include, for example, inorganic acids such as hydrochloric acid, sulfuric acid, phosphoric acid, hydrobromic acid, etc., and, organic acids such as oxalic acid, maleic acid, fumaric acid, malic acid, tartaric acid, citric acid, benzoic acid, etc. Also, the basic compounds used for forming the salts include, for example, sodium hydroxide, potassium hydroxide, calcium hydroxide, sodium carbonate, potassium hydrogencarbonate, etc.

When $R^{11}$ is a phenylcarbamoyl-lower alkyl group which may have 1 or 2 lower alkoxy groups on the phenyl ring thereof, it can be obtained by reacting a compound in which the corresponding $R^{11}$ has a carboxy-lower alkyl group with phenylamine which may have 1 or 2 lower alkoxy groups on the phenyl ring thereof in the same manner as the amido bond-forming reaction in the reaction step 3.

The compound of the general formula (1) produced by each method described above and the salt thereof can be easily isolated from the reaction system and purified by a conventional separation means such as a distillation method, a recrystallization method, column chromatography, a preparative thin-layer chromatography, a solvent extraction method, etc.

The Maillard reaction inhibitor of the present invention is usually used in the form of a general pharmaceutical preparation. The preparation is prepared by using a diluent or an excipient commonly employed in the art such as a filler, an extender, a binder, a humidifying agent, a disintegrating agent, a surface active agent, a lubricant, etc. As the pharmaceutical preparation, various forms can be selected according to the purpose of the treatment. Typical examples thereof are tablets, pills, powders, liquids, suspensions, emulsions, granules, capsules, suppositories, injections (liquids, suspensions, etc.), ointments, etc. For forming tablets, excipients such as lactose, sucrose, sodium chloride, glucose, urea, starch, calcium carbonate, kaolin, crystalline cellulose, silicic acid etc.; binders such as water, ethanol, propanol, simple syrup, a glucose solution, a starch solution, a gelatin solution, carboxymethyl cellulose, shellac, methyl cellulose, potassium phosphate, polyvinyl pyrrolidone, etc.; disintegrating agents such as dry starch, sodium alginate, an agar powder, a laminaran powder, sodium hydrogencarbonate, calcium carbonate, polyoxyethylene sorbitan fatty acid esters, sodium lauryl sulfate, stearic acid monoglyceride, starch, lactose, etc.; disintegration inhibitors such as sucrose, stearin, cacao butter, a hydrogenated oil etc.; absorption accelerators such as quaternary ammonium bases, sodium lauryl sulfate, etc.; moisture keeping agents such as glycerol, starch, etc.; absorbents such as starch, lactose, kaolin, bentonite, colloidal silicic acid, etc.; lubricants such as purified talc, stearates, a boric acid powder, polyethylene glycol, etc.; can be used as carriers. Furthermore, if necessary, the tablets may be applied with ordinary coating to form, for example, sugar-coated tablets, gelatin-coated tablets, enteric coated tablets, film-coated tablets, double coated tablets, and multilayer tablets. For forming pills, excipients such as glucose, lactose, starch, cacao butter, hardened vegetable oils, kaolin, talc, etc.; binders such as a gum arabic powder, a tragacanth rubber powder, gelatin, ethanol, etc.; disintegrating agents such as laminaran, agar, etc.; can be used as carriers. For forming suppositories, polyethylene glycol, cacao butter, higher alcohols, higher alcohol esters, gelatin, semi-synthetic glyceride, etc.; can be used as carriers. The preparation of capsules is carried out by mixing the compound of the present invention with various carriers described above and filling the mixture in hard gelatin capsules, hard capsules, etc., in accordance with a conventional manner. In the case of preparing injections, liquids, emulsions, or suspensions are sterilized and preferably made as isotonic to blood. For preparing the injections, water, an aqueous lactic acid solution, ethanol, propylene glycol, ethoxylated isostearyl alcohol, polyoxyethylene sorbitan fatty acid esters, etc., can be used as a diluent. In this case, for preparing an isotonic solution, a sufficient amount of sodium chloride, glucose, or glycerol may be incorporated in the pharmaceutical preparation or an ordinary dissolution aid, a buffer, a pain alleviating agent, etc., may be added thereto. Furthermore, if necessary, a coloring agent, a preservative, a perfume, a flavoring agent, a sweetening agent, etc. and other pharmaceutical agents may be incorporated in the pharmaceutical preparation. For forming pastes, creams and gels, white vaseline, paraffin, glycerol, a cellulose derivative, polyethylene glycol, silicone, bentonite, etc., can be used as a diluent.

The amount of the compound of the present invention to be contained in the pharmaceutical preparation of the present invention can be properly selected in a wide range without being limited but is usually from 1 to 70% by weight in the pharmaceutical preparation.

Although there is no particular restriction on the administration method of the pharmaceutical preparation of the present invention, and the various methods can be selected according to the age, sex, and other conditions of patients, the state of the disease, and the form of the preparation, the pharmaceutical preparation is usually administered systemically or topically by oral or parenteral administration. For example, the compound of the preparation is orally administrated in the form of tablets, pills, liquids, suspensions, emulsions, granules or capsules or is administrated in the form of injections or as a mixture with other ordinary auxiliary liquid by intravenous injection, percutaneous injection, subcutaneous injection, or intraperitoneal injection. Further, the preparation can be administrated in the rectum as a suppository or can be applied as an ointment.

The dose of the pharmaceutical preparation of the present invention is properly selected according to the age, weight, conditions of disease, treatment effect, administration method, treating time, etc. of patients, but is usually administrated at a dose in the range of from about 0.1 to 100 mg per kg of body weight per day. The preparation may be administrated once to several times per day. As the matter of course, the dosage level changes by various conditions as discussed above. Thus, as the case may be, the dosage may be less than the above-described range or over the range.

Now, the productions of the starting compounds are shown below as Referential Examples, the productions of the compounds for use in the present invention are shown below as Examples, and the pharmacological test results of these compounds and Preparation Examples are also shown below.

REFERENTIAL EXAMPLE 1

Production of 2-benzylidenehydrazono-1-methoxycarbonylmethylimidazolidin-4-one:

To a methanol solution of sodium methoxide prepared by dissolving 2.30 g of metal sodium in 150 ml of methanol was added 5.70 g of benzylideneaminoguanidine, and, after stirring the mixture for one hour at room temperature, 11.35 g of iminodiacetic acid diethyl ester was added thereto, followed by refluxing under heating for 17 hours. After cooling the reaction mixture, water and chloroform were added thereto to distribute the mixture between aqueous and organic layers and, then, the aqueous layer was extracted three times with chloroform. The organic layer was combined with the extract. After drying over anhydrous magnesium sulfate, the mixture was concentrated under reduced pressure, and the residue was charged on silica gel column chromatography, followed by elution with a mixed solvent of chloroform and methanol (100:1 (v/v)). Thus 2.61 g of 2-benzylidenehydrazono-1-methoxycarbonylmethylimidazolidin-4-one was obtained.

m.p. 149°–153° C. NMR (CDCl$_3$) δ ppm: 3.77 (s, 3H), 4.01 (s, 2H), 4.23 (s, 2H), 7.32–7.68 (m, 5H), 8.26 (s, 1H).

REFERENTIAL EXAMPLE 2

Production of 2-benzylidenehydrazono-3-ethoxycarbonylmethyl-1-methoxycarbonylmethylimidazotidin-4-one:

96 Milligrams of 60% sodium hydride was suspended in 20 ml of dimethylformamide under ice-cooling and 254 mg of the 2-benzylidenehydrazono-1-methoxycarbonylmethylimidazolidin-4-one obtained in the above Referential Example 1 was slowly dropped thereto, followed by stirring at 80° C. for one hour. After cooling the reaction mixture, water and chloroform were added thereto to distribute the mixture between aqueous and organic layers and, then, the aqueous layer was extracted three times with chloroform. The organic layer was combined with the extract. After drying over anhydrous magnesium sulfate, the mixture was concentrated under reduced pressure, and the residue was recrystallized from chloroform/n-hexane. Thus 320 mg of 2-benzylidenehydrazono-3-ethoxycarbonylmethyl-1-methoxycarbonylmethylimidazolidin-4-one was obtained.

NMR (CDCl$_3$) δ ppm: 1.29 (t, J=7.0 Hz, 3H), 3.71 (s, 3H), 4.17 (q, J=5.9 Hz, 2H), 4.14 (s, 2H), 4.41 (s, 2H), 4.71 (s, 2H), 7.25–7.60 (m, 5H), 8.13 (s, 1H).

REFERENTIAL EXAMPLE 3

Production of 7-ethoxycarbonylmethyl-1,4,5,7-tetraazabicyclo[4,3,0]nonan-5-en-3,8-dione:

To 230 mg of the 2-benzylidenehydrazono-3-ethoxycarbonylmethyl-1-methoxycarbonylmethylimidazolidin-4-one obtained in the above Referential Example 2 was added 10 ml of 0.5N hydrochloric acid and the mixture was steam-distilled for 40 minutes. After cooling, the reaction mixture was concentrated under reduced pressure and the residue was charged on silica gel column chromatography, followed by elution with a mixed solvent of chloroform and ethyl acetate (1:2 (v/v)). Thus 60 mg of 7-ethoxycarbonylmethyl-1,4,5,7-tetraazabicyclo[4.3.0]nonan-5-en-3,8-dione was obtained.

m.p. 188°–193° C. NMR (DMSO-d$_6$) δ ppm: 1.20 (t, J=6.81 Hz, 3H), 3.98 (s, 2H), 4.04 (q, J=6.91 Hz, 2H), 4.20 (s, 2H), 10.24 (s, 1H).

EXAMPLE 1

Production of 5-(4-benzyloxybenzyl)-2-isopropylidenehydrazonoimidazolidin-4-one:

To a methanol solution of sodium methoxide prepared by dissolving 1.69 g of sodium metal in 60 ml of methanol was added 3.00 g of isopropylideneaminoguanidine sulfate, and, after stirring the mixture for one hour at room temperature, 11.83 g of O-benzyl-L-tyrosine methyl ester hydrochloride was added thereto, followed by refluxing under heating for 6 hours. After cooling the reaction mixture to room temperature, the insoluble matters were filtered off and the filtrate was concentrated under reduced pressure. The residue was purified by silica gel column chromatography (eluent:chloroform) and further recrystallized from ethanol. Thus 2.15 g of the above-mentioned target compound was obtained as white crystals.

m.p. 172°–173° C. NMR (DMSO-d$_6$) δ ppm: 1.82, 1.92 (s, s, 6H), 2.8–3.0 (m, 2H), 4.15–4.30 (m, 1H), 5.04 (s, 2H), 6.90 (d, 2H), 7.10 (dr 2H), 7.25–7.50 (m, 5H).

EXAMPLE 2

Production of 2-isopropylidenehydrazono-5-methylimidazolidin-4-one:

By following the similar procedure to the above Example 1 but substituting the O-benzyl-L-tyrosine methyl ester hydrochloride with L-alanine ethyl ester hydrochloride, the above-mentioned target compound was obtained.

m.p. 126°–128° C. NMR (DMSO-d$_6$) δ ppm: 1.22 (d, 3H, J=6.8 Hz), 1.89 1.94 (s, s, 6H), 3.96 (q, 1H, J=6.8 Hz), 7.51 (s, 1H), 10.42 (brs, 1H).

EXAMPLE 3

Production of 5-benzyl-2-isopropylidenehydrazonoimidazolidin-4-one:

By following the similar procedure to the above Example 1 but substituting the O-benzyl-L-tyrosine methyl ester hydrochloride with L-phenylalanine ethyl ester hydrochloride, the above-mentioned target compound was obtained.

m.p. 148°–149° C. NMR (DMSO-d$_6$) δ ppm: 1.84, 1.93 (s, s, 6H), 2.8–3.1 (m, 2H), 4.13–4.38 (m, 1H), 7.26 (s, 5H).

EXAMPLE 4

Production of 5-(4-hydroxybenzyl)-2-isopropylidenehydrazonoimidazolidin-4-one:

By following the similar procedure to the above Example 1 but substituting the O-benzyl-L-tyrosine methyl ester hydrochloride with L-tyrosine ethyl ester hydrochloride, the above-mentioned target compound was obtained.

m.p. 218°–219° C. NMR (DMSO-d$_6$) δ ppm: 1.85, 1.93 (s, s, 6H), 2.7–3.0 (m, 2H), 4.08–4.38 (m, 1H), 6.68 (d, 2H), 7.01 (d, 2H), 7.31 (s, 1H), 9.38 (brs, 1H).

EXAMPLE 5

Production of 5-[4-(2,6-dichlorobenzyloxy)benzyl]-2-isopropylidenehydrazonoimidazolidin-4-one:

By following the similar procedure to the above Example 1 but substituting the O-benzyl-L-tyrosine methyl ester hydrochloride with O-2,6-dichlorobenzyl-L-tyrosine ester hydrochloride, the above-mentioned target compound was obtained.

NMR (CDCl$_3$) δ ppm: 1.99 (s, 3H), 2.05 (s, 3H), 2.75 (dd, 1H, J=9.57, 14.19 Hz), 3.27 (dd, 1H, J=3.30, 13.85 Hz), 4.17 (dd, 1H, J=3.63, 9.56 Hz), 5.26 (d, 2H), 6.98–7.38 (m, 7H).

EXAMPLE 6

Production of 5-[4-(4-chlorobenzyloxy)benzyl]-2-isopropylidenehydrazonoimidazolidin-4-one:

By following the similar procedure to the above Example 1 but substituting the O-benzyl-L-tyrosine methyl ester hydrochloride with O-4-chlorobenzyl-L-tyrosine ethyl ester hydrochloride, the above-mentioned target compound was obtained.

NNR (DMSO-$d_6$) δ ppm: 1.82, 1.92 (2s, 6H), 2.85 (dd, 1H, Jgem=13.86 Hz, J=4.62 Hz), 2.95 (dd, 1H, J=4.95 Hz), 4.20 (dd, 1H), 5.04 (s, 2H), 6.86–7.13 (m, 4H), 7.39–7.49 (m, 5H), 10.50 (brs, 1H).

EXAMPLE 7

Production of 5-(4-hydroxyphenyl)-2-isopropylidenehydrazonoimidazolidin-4-one:

By following the similar procedure to the above Example 1 but substituting the O-benzyl-L-tyrosine methyl ester hydrochloride with D-phenylglycine ethyl ester hydrochloride, the above-mentioned target compound was obtained.

NMR (DMSO-$d_6$) δ ppm: 1.92, 1.94 (2s, 6H), 4.85 (s, 1H), 6.69–7.17 (m, 4H), 7.98 (s, 1H), 9.57 (bs, 1H).

EXAMPLE 8

Production of 2-isopropylidenehydrazono-5-(4-phenylthiobenzyl)imidazolidin-4-one:

By following the similar procedure to the above Example 1 but substituting the O-benzyl-L-tyrosine methyl ester hydrochloride with 4-phenylthiophenylalanine ethyl ester hydrochloride, the above-mentioned target compound was obtained.

NMR (DMSO-$d_6$) δ ppm: 1.99, 2.12 (2s, 6H), 3.09 (m, 2H), 4.66 (m, 1H), 7.20–7.37 (m, 9H).

EXAMPLE 9

Production of 5-[N-(4-ethoxycarbonylphenyl)carbamoylmethyl]-2-isopropylidenehydrazonothiazolidin-4-one:

To a solution of 0.37 g of 5-carboxymethyl-2-isopropylidenehydrazonothiazolidin-4-one synthesized in accordance with the method described in JP-B-46-15936 and 0.26 g of ethyl 4-aminobenzoate in 10 ml of N,N-dimethylformamide was added 0.27 g of 1-hydroxybenztriazole hydrochloride. Subsequently, 0.34 g of 1-ethyl-3-(3'-dimethylaminopropyl)carbodiimide hydrochloride was added thereto and the mixture was stirred at room temperature for 16 hours. Then the reaction mixture was poured into a mixture of 100 ml of 2N hydrochloric acid with 100 ml of ethyl acetate. The organic phase thus separated was collected, washed with a saturated aqueous solution of sodium hydrogencarbonate and dried over anhydrous sodium sulfate. After distilling off the solvent under reduced pressure, the residue was purified by silica gel column chromatography (eluent:methylene chloride:methanol=9:1). Thus 0.37 g of the above-mentioned target compound was obtained.

NMR (DMSO-$d_6$) δ ppm: 1.31 (t, 3H, J=7.26 Hz), 1.93 (s, 3H), 1.95 (s, 3H), 2.93 (dd, 1H, J=9.23, 16.82 Hz), 3.20 (dd, 1H, J=3.96, 16.5 Hz), 4.24–4.36 (m, 3H), 7.69 (d, 2H, J=8.90 Hz), 7.92 (dr 2H, J=8.91 Hz), 10.46 (s, 1H), 11.71 (brs, 1H).

EXAMPLE 10

Production of 2-isopropylidenehydrazono-5-(N-propylcarbamoylmethyl)thiazolidin-4-one:

By following the similar procedure to the above Example 9 but substituting the ethyl 4-aminobenzoate with propylamine, the above-mentioned target compound was obtained.

NMR (DMSO-$d_6$) δ ppm: 0.83 (t, 3H, J=7.26 Hz), 1.36–1.44 (m, 2H), 1.94 (brs, 6H), 2.56 (dd, 1H, J=10.23, 16.17 Hz), 2.86–3.05 (m, 3H), 4.21 (dd, 1H, J=3.63, 9.9 Hz), 7.99 (t, 1H, J=5.61 Hz), 11.59 (brs, 1H).

EXAMPLE 11

Production of 2-isopropylidenehydrazono-5-[N-(2-oxo-1,2,3,4-tetrahydroquinolin-3-yl)carbamoylmethyl]thiazolidin-4-one:

By following the similar procedure to the above Example 9 but substituting the ethyl 4-aminobenzoate with 3-amino-3,4-dihydroquinolin-2(1H)-one, the above-mentioned target compound was obtained.

NMR (DMSO-$d_6$) δ ppm: 1.95 (s, 3H), 1.94 (s, 3H), 2.51–3.32 (m, 4H), 4.23–4.27 (m, 1H), 4.41–4.51 (m, 1H), 6.86–7.22 (m, 4H), 8.43 (m, 1H), 10.34 (d, 1H, J=2.31 Hz), 11.66 (brs, 1H).

EXAMPLE 12

Production of 5-(N-cyclohexylcarbamoylmethyl)-2-isopropylidenehydrazonothiazolidin-4-one:

By following the similar procedure to the above Example 9 but substituting the ethyl 4-aminobenzoate with cyclohexylamine, the above-mentioned target compound was obtained.

NMR (DMSO-$d_6$) δ ppm: 1.10–1.74 (m, 10H), 1.94 (s, 6H), 2.53 (dd, 1H), 2.87 (dds 1H, Jgem=16.17 Hz, J=3.96 Hz), 3.49 (m, 1H), 4.20 (dd, 1H, J=10.06 Hz), 7.90 (d, 1H, J=7.92 Hz), 11.62 (brs, 1H).

EXAMPLE 13

Production of 5-(N-ethoxycarbonylmethylcarbamoylmethyl)-2-isopropylidenehydrazonothiazolidin-4-one:

By following the similar procedure to the above Example 9 but substituting the ethyl 4-aminobenzoate with glycine ethyl ester, the above-mentioned target compound was obtained.

NMR (DMSO-$d_6$) δ ppm: 1.20 (t, 3H), 1.94 (s, 6H), 2.68 (dd, 1H, Jgem=16.49 Hz, J=6.26 Hz), 2.97 (dd, 1H, J=3.63 Hz), 3.83 (dd, 2H), 4.09 (q, 2H), 4.21 (dd, 1H), 8.50 (t, 1H, J=5.94 Hz), 11.66 (s, 1H).

EXAMPLE 14

Production of 5-[N-(4-carboxyphenyl)carbamoylmethyl]-2-isopropylidenehydrazonothiazolidin-4-one:

2.73 Grams of 5-[N-(4-ethoxycarbonylphenyl)carbamoylmethyl]-2-isopropylidenehydrazonothiazolidin-4-one produced in the above Example 9 was dissolved in 30 ml of dioxane. After adding 6.46 ml of 2N sodium hydroxide, the mixture was heated to 50° C. After 1 hour, the solvent was distilled off. The residue was dissolved in 100 ml of water and adjusted to pH 2 with 2N hydrochloric acid. The crystals thus formed were recovered by filtration and thus 2.02 g of the above-mentioned target compound was obtained.

NMR (DMSO-$d_6$): 1.94 (s, 3H), 1.95 (s, 3H), 2.92 (dd, 1H, J=9.23, 16.82 Hz), 3.19 (dd, 1H, J=3.96, 16.83 Hz), 4.34 (dd, 1H, J=4.04. 9.23 Hz), 7.67 (d, 2H, J=8.90 Hz), 7.89 (d, 2H, J=8.58 Hz), 10.43 (s, 1H).

EXAMPLE 15

Production of 5-carboxymethyl-3-ethoxycarbonylmethyl-2-isopropylidenehydrazonothiazolidin-4-one:

1.15 Gram of 5-carboxymethyl-2-isopropylidenehydrazono-thiazolidin-4-one was dissolved in 30 ml of dimethylformamide and 0.24 g of 60% sodium hydride was added thereto in portions under ice-cooling. After 30 minutes, 0.74 g of ethyl chloroacetate was added and the mixture was stirred at room temperature for 15 hours. The reaction mixture was poured into 200 ml of ice water and extracted with 200 ml of ethyl acetate. The organic layer was dried over anhydrous sodium sulfate and then the solvent was distilled off. The residue was purified by silica gel column chromatography (eluent:hexane:ethyl acetate=1:1). Thus 0.36 g of the above-mentioned target compound was obtained.

NMR (CDCl$_3$) δ ppm: 1.29 (t, 3H, J=6.92 Hz), 2.02 (s, 3H), 2.04 (s, 3H), 2.97 (dd, 1H, J=9.9, 17.48 Hz), 3.35 (dd, 1H, J=3.63, 17.82 Hz), 4.23 (q, 2H, J=7.26 Hz), 4.31 (dd, 1H, J=3.63, 9.9 Hz), 4.66 (s, 2H).

EXAMPLE 16

Production of 2-isopropylidenehydrazono-3-phenylthiazolidin-4-one:

0.19 Gram of acetone 4-phenyl-3-thiosemicarbazone was dissolved in 7 ml of ethanol and 0.13 g of ethyl chloroacetate and 0.09 g of sodium acetate were successively added thereto. After refluxing under heating for 15 hours, the mixture was allowed to cool and the crystals thus precipitated were recovered by filtration. Thus 0.13 g of the above-mentioned target compound was obtained as a white product.

NMR (DMSO-d$_6$) δ ppm: 1.74 (s, 3H), 1.93 (s, 3H), 4.03 (s, 2H), 7.32–7.53 (m, 5H).

EXAMPLE 17

Production of 2-isopropylidenehydrazino-4-methylthiazole:

0.79 Gram of acetone thiosemicarbazone was dissolved in 20 ml of ethanol and 0.69 g of chloroacetone and 0.59 g of sodium acetate were successively added thereto. After refluxing under heating for 3 hours, the mixture was allowed to cool. Then the insoluble matters were filtered off and the filtrate was concentrated under reduced pressure. The residue was purified by silica gel column chromatography (eluent:methylene chloride:methanol=10:1). Thus 0.18 g of the above-mentioned target compound was obtained.

NMR (CDCl$_3$) δ ppm: 1.91 (s, 3H), 2.04 (s, 3H), 2.23 (s, 3H), 6.13 (s, 1H).

EXAMPLE 18

Production of 2-isopropylidenehydrazino-4-phenylthiazole:

By following the similar procedure to the above Example 17 but substituting the chloroacetone with 2-bromoacetophenone, the above-mentioned target compound was obtained.

NMR (DMSO-d$_6$) δ ppm: 1.94 (s, 3H), 1.96 (s, 3H), 7.21 (s, 1H), 7.25–7.42 (m, 3H), 7.84–7.87 (m, 2H), 10.95 (brs, 1H).

EXAMPLE 19

Production of 4-(4-chlorophenyl)-2-isopropylidenehydrazinothiazole:

By following the similar procedure to the above Example 17 but substituting the chloroacetone with 2-bromo-4'-chloroacetophenone, the above-mentioned target compound was obtained.

NMR (CDCl$_3$) δ ppm: 1.76 (s, 3H), 2.01 (s, 3H), 6.81 (s, 1H), 7.30–7.36 (m, 2H), 7.66–7.73 (m, 2H), 8.99 (brs, 1H).

EXAMPLE 20

Production of 2-isopropylidenehydrazino-4-(4-phenylthiophenyl)thiazole:

By following the similar procedure to the above Example 17 but substituting the chloroacetone with 2-bromo-4'-phenylthioacetophenone, the above-mentioned target compound was obtained.

NMR (CDCl$_3$) δ ppm: 1.83 (s, 3H), 2.03 (s, 3H), 6.83 (s, 1H), 7.22–7.36 (m, 7H), 7.68–7.72 (m, 2H), 8.67 (brs, 1H).

EXAMPLE 21

Production of 4-(3,4-dihydroxyphenyl)-2-isopropylidenehydrazinothiazole:

By following the similar procedure to the above Example 17 but substituting the chloroacetone with 2-chloro-3',4'-dihydroxyacetophenone, the above-mentioned target compound was obtained.

NMR (DMSO-d$_6$) δ ppm: 1.92 (s, 3H), 1.94 (s, 3H), 6.73 (d, 1H, J=8.25 Hz), 6.85 (s, 1H), 7.12 (d, 1H, J=7.82 Hz), 7.23 (s, 1H), 10.52 (brs, 1H).

EXAMPLE 22

Production of 4-[4-(4-chlorobenzyloxy)phenyl]-2-isopropylidenehydrazinothiazole:

By following the similar procedure to the above Example 17 but substituting the chloroacetone with 4-(4-chlorobenzyloxy)phenacyl bromide, the above-mentioned target compound was obtained.

NMR (DMSO-d$_6$) δ ppm: 1.89 (s, 3H), 1.93 (s, 3H), 5.12 (s, 2H), 6.99–7.05 (m, 3H), 7.43–7.58 (m, 4H), 7.75–7.89 (m, 2H), 10.58 (s, 1H).

EXAMPLE 23

Production of 2-isopropylidenehydrazino-4,5,6,7-tetrahydrobenzothiazole:

By following the similar procedure to the above Example 17 but substituting the chloroacetone with 2-chlorocyclohexanone, the above-mentioned target compound was obtained.

NMR (CDCl$_3$) δ ppm: 1.73–1.84 (m, 4H), 1.87 (s, 3H), 2.02 (s, 3H), 2.53–2.61 (m, 4H).

EXAMPLE 24

Production of 3-benzyl-5-(4-hydroxybenzyl)-2-isopropylidenehydrazonoimidazolidin-4-one:

0.26 Gram of 5-(4-hydroxybenzyl)-2-isopropylidenehydrazonoimidazolidin-4-one produced in the above Example 4 was dissolved in 5 ml of N,N-dimethylformamide. Then 0.18 g of benzyl bromide and 0.07 g of potassium carbonate were added thereto and the mixture was heated in an oil bath at 80° C. for 8 hours. The reaction mixture was poured into 50 ml of ice water and extracted with 100 ml of ethyl acetate. The organic layer was dried over anhydrous sodium sulfate and the solvent was distilled off under reduced pressure. The residue was purified by silica gel column chromatography (eluent:chloroform:methanol=10:1). Thus 0.11 g of the above-mentioned target compound was obtained.

NMR(CDCl$_3$) δ ppm: 1.95 (s, 3H), 1.96 (s, 3H), 2.77 (dd, 1H, J=7.92 Hz, 13.86 Hz), 3.12 (dd, 1H, J=3.96 Hz, 14.18

Hz), 4.23 (dd, 1H, J=3.63 Hz, 7.92 Hz), 4.70 (d, 2H, J=2.64 Hz), 6.61–6.64 (m, 2H), 6.96–6.99 (m, 2H), 7.22–7.28 (m, 5H).

EXAMPLE 25

Production of 5-(4-hydroxybenzyl)-2-isopropylidenehydrazo-3-(4-methoxybenzyl)imidazolidin-4-one:

By following the similar procedure to the above Example 24 but substituting the benzyl bromide with p-methoxybenzyl chloride, the above-mentioned target compound was obtained.

NMR (CDCl$_3$) δ ppm: 1.96 (s, 3H), 1.99 (s, 3H), 2.75 (dd, 1H, J=7.92 Hz, 13.86 Hz), 3.09 (dd, 1H, J=3.95 Hz, 14.18 Hz), 4.21 (dd, 1H, J=3.63 Hz, 7.92 Hz), 4.61 (d, 2H, J=2.97 Hz), 6.59 (dr 2H, J=8.58 Hz), 6.79 (d, 2H, J=8.57 Hz), 6.95 (d, 2H, J=8.25 Hz), 7.23 (d, 2H, J=8.57 Hz).

EXAMPLE 26

Production of 5-(4-benzyloxybenzyl)-2-isopropylidenehydrazonothiazolidin-4-one:

1.28 Gram of ethyl 3-(4-benzyloxyphenyl)-2-chloropropionate was dissolved in 20 ml of ethanol. After adding 0.63 g of acetone thiosemicarbazone and 0.40 g of sodium acetate, the mixture was refluxed under heating for 20 hours. Then the reaction mixture was concentrated under reduced pressure. After adding 50 ml of water, the mixture was extracted with 100 ml of ethyl acetate. The extract was dried over anhydrous sodium sulfate and the solvent was distilled off under reduced pressure. Then the residue was purified by silica gel column chromatography (eluent:hexane:ethyl acetate=1:1). Thus 0.4 g of the above-mentioned target compound was obtained.

NMR (CDCl$_3$) δ ppm: 1.99 (s, 3H), 2.02 (s, 3H), 2.94 (dd, 1H, J=10.23, 14.19 Hz), 3.48 (dd, 1H, J=3.63, 14.19 Hz), 4.21 (dd, 1H, J=3.63, 10.23 Hz), 5.04 (s, 2H), 6.90–7.41 (m, 9H).

EXAMPLE 27

Production of 2-isopropylidenehydrazono-5-(4-methylthiobenzyl)thiazolidin-4-one:

By following the similar procedure to the above Example 26 but substituting the ethyl 3-(4-benzyloxyphenyl)-2-chloropropionate with ethyl 2-chloro-3-(4-methylthiophenyl)propionate, the above-mentioned target compound was obtained.

NMR (CDCl$_3$) δ ppm: 1.99 (s, 3H), 2.02 (s, 3H), 2.47 (s, 3H), 2.95 (dd, 1H, J=10.23, 14.19 Hz), 3.49 (dd, 1H, J=3.96, 14.19 Hz), 4.22 (dd, 1H, J=3.63, 10.23 Hz), 10.04 (brs, 1H), 7.15–7.21 (m, 4H).

EXAMPLE 28

Production of 9-benzyloxymethyl-1,4,5,7-tetraazabicyclo[4,3,0]nonan-5-en-3,8-dione:

0.21 Gram of 1,4,5,7-tetraazabicyclo[4.3.0]nonan-5-en-3, 8-dione, which was a material obtained in the same manner as the one described in Referential Example 3, was suspended in a mixture of 4 ml of tetrahydrofuran with 1 ml of hexamethylphosphorictriamide. Then 2.86 ml of a 1.6M solution of butyl lithium in hexane was added dropwise thereto under cooling in a dry ice/acetone bath and the mixture was stirred at the same temperature for 2 hours. To this reaction mixture was dropped a solution of 0.28 ml of benzylchloromethyl ether in 1 ml of hexamethylphosphorictriamide. Then the reaction mixture was stirred under cooling at −30° to −40° C. for one hour and further under ice-cooling for 90 minutes. After adding 20 ml of 1N hydrochloric acid, the reaction mixture was extracted with 80 ml of ethyl acetate. The extract was dried over anhydrous sodium sulfate and concentrated under reduced pressure. The residue was purified by preparative silica gel thin-layer chromatography (developer:chloroform:methanol=10:1). Thus 0.05 g of the above-mentioned target compound was obtained.

NMR (DMSO-d$_6$) δ ppm: 3.65–3.80 (m, 4H), 4.07–4.08 (m, 1H), 4.52 (s, 2H), 7.23–7.39 (m, 5H), 10.15 (d, 1H), 11.13 (brs., 1H).

EXAMPLE 29

Production of 2-isopropylidenehydrazono-5-(4-nitrobenzyl) imidazolidin-4-one:

By following the similar procedure to the above Example 1 but substituting the O-benzyl-L-tyrosine methyl ester hydrochloride with 4-nitrophenylalanine ethyl ester hydrochloride, the above-mentioned target compound was obtained.

NMR (DMSO-d$_6$) δ ppm: 1.82, 1.92 (s, s, 6H), 3.06 (dd, 1H, Jgem=13.70, J=4.83 Hz), 3.154 (dd, 1H), 4.32 (t, 1H), 7.48 (d, 2H), 8.14 (d, 2H), 7.63 (brs, 1H), 10.62 (brs, 1H).

EXAMPLE 30

Production of 5-[4-(cyclohexylmethyloxy)benzyl]-2-isopropylidenehydrazonoimidazolin-4-one:

By following the similar procedure to the above Example 1 but substituting the O-benzyl-L-tyrosine methyl ester hydrochloride with O-cyclohexylmethyl-L-tyrosine ethyl ester hydrochloride, the above-mentioned target compound was obtained.

NMR (DMSO-d$_6$) δ ppm: 2.83 (dd, 1H, Jgem=14.02 Hz, J=4.78 Hz), 2.93 (dd, 1H), 3.71 (d, 2H, J=5.94 Hz), 4.18 (t, 1H), 6.78 (d, 2H), 7.08 (d, 2H), 7.39 (brs, 1H), 10.50 (brs, 1H).

EXAMPLE 31

Production of 5-4-(benzylbenzyl)-2-isopropylidenehydrazonoimidazolin-4-one:

By following the similar procedure to the above Example 1 but substituting the O-benzyl-L-tyrosine methyl ester hydrochloride with 4-benzylphenylalanine ethyl ester hydrochloride, the above-mentioned target compound was obtained.

NMR (DMSO-d$_6$) δ ppm: 1.99, 2.13 (2s, 6H), 3.03 (m, 2H), 3.83 (dd, 2H), 4.65 (t, 1H), 6.99–7.30 (m, 10H), 12.15 (brs, 1H).

EXAMPLE 32

Production of 5-[4-(4-chlorobenzoylamino)benzyl]-2-isopropylidenehydrazonoimidazolidin-4-one:

In 40 ml of ethanol and in the presence of 20 mg of 10% palladium carbon, 200 mg of 2-isopropylidenehydrazono-5-(4-nitrobenzyl)imidazolidin-4-one produced in the above Example 29 was catalytically reduced by using Pearl's device at room temperature under pressure of 3 kg/cm$^2$. After 3 hours, the catalyst was filtered off and the solvent was distilled off under reduced pressure. Then the residue was dissolved in 10 ml of chloroform and 0.1 ml of triethylamine was added thereto. To the resulting mixture was dropped 0.1 ml of 4-chlorobenzoyl chloride under ice-cooling. After stirring at room temperature for 2 hours, the mixture was successively washed with 1% hydrochloric acid and a saturated aqueous solution of sodium chloride and dried over anhydrous magnesium sulfate. After distilling off the solvent under reduced pressure, the residue was purified by preparative thin-layer chromatography (developer:chloroform:methanol=8:2). Thus 50 mg of the above-mentioned target compound was obtained.

NMR (DMSO-$d_6$) δ ppm: 1.82, 1.92 (s, s, 6H), 2.93, 2.98 (dd, dd, 2H), 4.23 (m, 1H), 7.15–7.98 (m, 4H), 7.53–7.64 (m, 4H), 10.24 (brs, 1H).

EXAMPLE 33

Production of 2-isopropylidenehydrazono-5-(N-phenylcarbamoylmethyl)thiazolidin-4-one:

By following the similar procedure to the above Example 9 but substituting the ethyl 4-aminobenzoate with aniline, the above-mentioned target compound was obtained.

NMR (DMSO-$d_6$) δ ppm: 1.93, 1.95 (2s, 6H), 2.87 (dd, 1H, Jgem=16.5 Hz, J=9.57 Hz), 3.16 (dd, 1H, J=3.95 Hz), 4.33 (dd, 1H), 7.0–7.6 (m, 5H), 10.11 (brs, 1H), 11.70 (brs, 1H).

EXAMPLE 34

Production of 5-(N-isopropylcarbamoylmethyl)-2-isopropylidenehydrazonothiazolidin-4-one:

By following the similar procedure to the above Example 9 but substituting the ethyl 4-aminobenzoate with isopropylamine, the above-mentioned target compound was obtained.

NMR (DMSO-$d_6$) δ ppm: 1.03, 1.05 (2s, 6H), 1.94 (s, 6H), 2.86 (dd, 1H, Jgem=16.2 Hz, J=3.63 Hz), 3.15 (dd, 1H), 3.81 (m, 1H), 4.20 (dd, 1H, J=9.9 Hz), 7.90 (d, 1H), 11.64 (s, 1H).

EXAMPLE 35

Production of 5-(N-benzylcarbamoylmethyl)-2-isopropylidenehydrazonothiazolidin-4-one:

By following the similar procedure to the above Example 9 but substituting the ethyl 4-aminobenzoate with benzylamine, the above-mentioned target compound was obtained.

NMR (DMSO-$d_6$) δ ppm: 1.94 1.95 (2s, 6H), 2.67 (dd, 1H, Jgem=16.2 Hz, J=9.6 Hz), 2.97 (dd, 1H, J=4.0 Hz), 4.25 (m, 3H), 7.27 (m, 5H), 8.54 (t, 1H, J=5.9 Hz), 11.65 (brs, 1H).

EXAMPLE 36

Production of 5-[4-(4-chlorophenylthio)benzyl]-2-isopropylidenehydrazonothiazolidin-4-one:

A mixture comprising 0.68 g of methyl 2-chloro-3-[4-(4-chlorophenylthio)phenyl]propionate, 0.32 g of acetone thiosemicarbazone, 0.20 g of sodium acetate and 20 ml of ethanol was refluxed under heating for 24 hours. After allowing to cool, the insoluble matters were filtered off and the solvent was distilled off under reduced pressure. The residue was purified by silica gel column chromatography (eluent:hexane:ethyl acetate=2:1). Thus 0.25 g of the above-mentioned target compound was obtained.

NMR(CDCl$_3$) δ ppm: 1.99 (s, 3H), 2.07 (s, 3H), 3.00 (dd, 1H, J=10.23, 14.19 Hz), 3.52 (dd, 1H, J=3.63, 14.19 Hz), 4.22 (dd, 1H, J=3.63, 10.23 Hz), 7.18–7.35 (m, 4H).

EXAMPLE 37

Production of 2-isopropylidenehydrazono-5-[N-(2-methoxycarbonyl-4-methylphenyl)carbamoylmethyl]thiazolidin-4-one:

By following the similar procedure to the above Example 9 but substituting the ethyl 4-aminobenzoate with methyl 2-amino-5-methylbenzoate, the above-mentioned target compound was obtained.

NMR (DMSO-$d_6$) δ ppm: 1.93, 1.94 (2s, 6H), 2.31 (s, 3H), 2.96 (dd, 1H, Jgem=16.49 Hz, J=9.24 Hz), 3.18 (dd, 1H, J=3.63 Hz), 3.83 (s, 3H), 4.31 (dd, 1H), 7.39–7.96 (m, 3H, phenyl), 10.44 (brs, 1H), 11.70 (brs, 1H).

EXAMPLE 38

Production of 5-[N-(2-carboxy-4-methylphenyl)carbamoylmethyl]-2-isopropylidenehydrazonothiazolidin-4-one:

By following the similar procedure to the above Example 14 but using 2-isopropylidenehydrazono-5-[N-(2-methoxycarbonyl-4-methylphenyl)carbamoylmethyl]thiazolidin-4-one as a starting material, the above-mentioned target compound was obtained.

NMR (DMSO-$d_6$) δ ppm: 1.93, 1.95 (2s, 6H), 2.30 (s, 3H), 3.00 (dd, 1H, Jgem=16.49 Hz, J=8.91 Hz), 3.19 (dd, 1H, J=3.96 Hz), 4.32 (dd, 1H), 7.38 (d, 1H), 7.78 (d, 1H), 8.25 (s, 1H), 11.07 (brs, 1H).

EXAMPLE 39

Production of 5-(N-carboxymethylcarbamoylmethyl)-2-isopropylidenehydrazonothiazolidin-4-one:

By following the similar procedure to the above Example 14 but using 5-(N-ethoxycarbonylmethylcarbamoylmethyl)-2-isopropylidenehydrazonothiazolidin-4-one obtained in Example 13 as a starting material, the above-mentioned target compound was obtained.

NMR (DMSO-$d_6$) δ ppm: 1.94 (s, 6H), 2.61 (dd, 2H, Jgem=9.90 Hz, J=3.30 Hz), 4.07 (dd, 1H), 4.20, 4.25 (2dd, 2H), 8.24 (t, 1H).

EXAMPLE 40

Production of 2-isopropylidenehydrazono-5-[N-(4-methylphenyl)carbamoylmethyl]thiazolidin-4-one:

By following the similar procedure to the above Example 9 but substituting the ethyl 4-aminobenzoate with p-toluidine, the above-mentioned target compound was obtained.

NMR (DMSO-$d_6$) δ ppm: 1.93, 1.94 (28, 6H), 2.24 (s, 3H), 2.83 (dd, 1H, Jgem=16.49 Hz, J=9.57 Hz), 3.13 (dd, 1H, J=3.63 Hz), 4.32 (dd, 1H), 7.09, 7.44 (2d, 4H), 10.00 (brs, 1H), 11.67 (brs, 1H).

EXAMPLE 41

Production of 2-isopropylidenehydrazono-5-[4-(3-pyridylmethoxy)benzyl]thiazolidin-4-one:

By following the similar procedure to the above Example 26 but substituting the ethyl 3-(4-benzyloxyphenyl)-2-chloropropionate with methyl 2-chloro-3-[4-(3-pyridylmethyloxy)phenyl]propionate, the above-mentioned target compound was obtained.

NMR (DMSO-de) δ ppm: 1.91 (s, 6H), 2.91 (dd, 1H, J=14.19 Hz, J=9.57 Hz), 4.46 (dd, 1H, J=4.29 Hz, J=9.24 Hz), 5.12 (s, 2H), 6.97 (d, 2H, J=8.58 Hz), 7.18 (d, 2H, J=8.58 Hz), 7.40–7.45 (m, 1H), 7.84–7.89 (m, 1H), 8.53–8.56 (m, 1H), 8.66 (d, 1H, J=1.65 Hz) 11.68 (s, 1H).

EXAMPLE 42

Production of 2-isopropylidenehydrazono-5-[4-(2-phenylethoxy)benzyl]imidazolidin-4-one:

By following the similar procedure to the above Example 1 but substituting the O-benzyl-L-tyrosine methyl ester hydrochloride with O-2-phenethyltyrosine methyl ester, the above-mentioned target compound was obtained.

NMR (CDCl$_3$) δ ppm: 1.93 (s, 3H), 2.01 (s, 3H), 2.72 (dd, 1H, J=8.91 Hz, J=14.19 Hz), 3.05 (t, 2H, J=6.93 Hz), 3.16 (dd, 1H, J=3.63 Hz, J=14.19 Hz), 4.10 (dd, 1H, J=7.26 Hz, J=11.22 Hz), 4.11 (t, 2H, J=6.93 Hz), 6.81 (d, 2H, J=8.58 Hz), 7.10 (d, 2H, J=8.58 Hz), 7.18–7.32 (m, 5H).

EXAMPLE 43

Production of 5-(3-indolylmethyl)-2-isopropylidenehydrazonoimidazolidin-4-one:

By following the similar procedure to the above Example 1 but substituting the O-benzyl-L-tyrosine methyl ester hydrochloride with L-tryptophane methyl ester hydrochloride, the above-mentioned target compound was obtained.

NMR (DMSO-d$_6$) δ ppm: 1.80 (s, 3H), 1.90 (s, 3H), 3.00–3.16 (m, 2H), 4.23 (t, 1H, J=4.29 Hz), 6.91–7.06 (m, 2H), 7.11 (s, 1H), 7.31 (s, 1H), 7.29 (d, 1H, J=8.01 Hz), 7.56 (d, 1H, J=7.92 Hz), 10.48 (brs, 1H), 10.82 (brs, 1H).

EXAMPLE 44

Production of 2-isopropylidenehydrazono-5-[4-(2-thienylmethoxy)benzyl]imidazolidin-4-one:

By following the similar procedure to the above Example 1 but substituting the O-benzyl-L-tyrosine methyl ester hydrochloride with O-2-thienylmethyl-L-tyrosine ethyl ester, the above-mentioned target compound was obtained.

NMR (DMSO-d$_6$) δ ppm: 1.82, 1.92 (2s, 6H), 2.85 (dd, 1H, Jgem=13.86 Hz, J=4.62 Hz), 2.95 (dd, 1H, J=4.95 Hz), 4.19 (t, 1H), 5.22 (s, 2H), 6.87–7.55 (m, 7H), 7.54 (d, 1H), 10.52 (brs, 1H).

EXAMPLE 45

Production of 5-(5-hydroxy-3-indolylmethyl)-2-isopropylidenehydrazonoimidazolidin-4-one:

By following the similar procedure to the above Example 1 but substituting the O-benzyl-L-tyrosine methyl ester hydrochloride with DL-5-hydroxytryptophane methyl ester hydrochloride, the above-mentioned target compound was obtained.

NMR (DMSO-d$_6$) δ ppm: 1.82 (s, 3H), 1.91 (s, 3H), 2.93 (dd, 1H, J=5.27 Hz, 14.84 Hz), 3.04 (dd, 1H, J=4.62 Hz, 14.85 Hz), 4.19 (t, 1H, J=4.95 Hz), 6.57 (dd, 1H, J=2.31 Hz, 8.58 Hz), 6.86 (d, 1H, J=1.98 Hz), 7.02 (d, 1H, J=2.31 Hz ), 7.27 (s, 1H), 8.58 (brs, 1H), 10.51 (brs, 1H).

EXAMPLE 46

Production of 5-(3,4-dihydroxybenzyl)-2-isopropylidenehydrazonoimidazolidin-4-one:

By following the similar procedure to the above Example 1 but substituting the O-benzyl-L-tyrosine methyl ester hydrochloride with DL-3-(3,4-dihydroxyphenyl)alanine ethyl ester hydrochloride, the above-mentioned target compound was obtained.

NMR (DMSO-d$_6$) δ ppm: 1.83 (s, 3H), 1.91 (s, 3H), 2.71 (dd, 1H, J=4.95 Hz, 13.86 Hz), 2.83 (dd, 1H, J=4.95 Hz, 13.85 Hz), 4.12 (t, 1H, J=4.29 Hz), 6.44 (dd, 1H, J=1.98 Hz, 7.92 Hz), 6.57–6.59 (m, 2H), 7.24 (brs, 1H), 7.47 (brs, 1H).

EXAMPLE 47

Production of 5-[N-(3,4-difluorophenyl)carbamoylmethyl]-2-isopropylidenehydrazonothiazolidin-4-one:

By following the similar procedure to the above Example 9 but substituting the ethyl 4-aminobenzoate with 3,4-difluoroaniline, the above-mentioned target compound was obtained.

NMR (DMSO-d$_6$) δ ppm: 1.94, 1.95 (2s, 6H), 2.89 (dd, 1H, Jgem=16.50 Hz, J=9.24 Hz), 3.15 (dd, 1H, J=3.96 Hz), 4.33 (dd, 1H), 7.23–7.79 (m, 3H), 10.37 (brs, 1H), 11.72 (brs, 1H).

EXAMPLE 48

Production of 5-[N-(4-benzyloxyphenyl)carbamoylmethyl]-2-isopropylidenehydrazonothiazolidin-4-one:

By following the similar procedure to the above Example 9 but substituting the ethyl 4-aminobenzoate with 4-benzyloxyaniline, the above-mentioned target compound was obtained.

NMR (DMSO-d$_6$) δ ppm: 2.08, 2.09 (2s, 6H), 2.97 (dd, 1H, Jgem=16.50 Hz, J=9.57 Hz), 3.27 (dd, 1H, J=3.96 Hz), 4.46 (dd, 1H), 5.21 (s, 2H), 7.09–7.63 (mr 9H), 10.12 (brs, 1H), 11.82 (brs, 1H).

EXAMPLE 49

Production of 5-[N-(4-chlorophenyl)carbamoylmethyl]-2-isopropylidenehydrazonothiazolidin-4-one:

By following the similar procedure to the above Example 9 but substituting the ethyl 4-aminobenzoate with 4-chloroaniline, the above-mentioned target compound was obtained.

NMR (DMSO-d$_6$) δ ppm: 1.93, 1.94 (2s, 6H), 2.87 (dd, 1H, Jgem=16.50 Hz, J=9.57 Hz), 3.15 (dd, 1H, J=3.95 Hz), 4.32 (dd, 1H), 7.36, 7.58 (2d, 4H), 10.25 (brs, 1H), 11.69 (brs, 1H).

EXAMPLE 50

Production of 2-isopropylidenehydrazono-5-[N-(4-methoxyphenyl)carbamoylmethyl]thiazolidin-4-one:

By following the similar procedure to the above Example 9 but substituting the ethyl 4-aminobenzoate with p-anisidine, the above-mentioned target compound was obtained.

NMR (DMSO-d$_6$) δ ppm: 1.93 1.94 (2s, 6H), 2.82 (dd, 1H, Jgem=16.16 Hz, J=9.57 Hz), 3.11 (dd, 1H, J=3.96 Hz), 3.72 (s, 3H), 4.31 (dd, 1H), 6.87, 7.86 (2d, 4H), 9.97 (brs, 1H), 11.69 (brs, 1H).

EXAMPLE 51

Production of 2-isopropylidenehydrazono-5-[N-(4-methylthiophenyl)carbamoylmethyl]thiazolidin-4-one:

By following the similar procedure to the above Example 9 but substituting the ethyl 4-aminobenzoate with 4-methylthioaniline, the above-mentioned target compound was obtained.

NMR (DMSO-d$_6$) δ ppm: 1.93, 1.95 (2s, 6H), 2.44 (s, 3H), 2.85 (dd, 1H, Jgem=16.49 Hz, J=9.24 Hz), 3.14 (dd, 1H, J=3.95 Hz), 4.31 (dd, 1H), 7.22 (d, 2H), 7.52 (d, 2H), 10.11 (brs, 1H), 11.68 (brs, 1H).

EXAMPLE 52

Production of 5-[N-(4-bromophenyl)carbamoylmethyl]-2-isopropylidenehydrazonothiazolidin-4-one:

By following the similar procedure to the above Example 9 but substituting the ethyl 4-aminobenzoate with 4-bromoaniline, the above-mentioned target compound was obtained.

NMR (DMSO-d$_6$) δ ppm: 1.93, 1.94 (2s, 6H), 2.87 (dd, 1H, Jgem=16.50 Hz, J=9.24 Hz), 3.15 (dd, 1H, J=3.95 Hz), 4.33 (m, 1H), 7.46–7.56 (m, 4H), 10.25 (brs, 1H), 11.69 (brs, 1H).

EXAMPLE 53

Production of 2-isopropylidenehydrazono-5-[N-(3,4,5-trichloro-phenyl)carbamoylmethyl]thiazolidin-4-one By following the similar procedure to the above Example 9 but substituting the ethyl 4-aminobenzoate with 3,4,5-trichloroaniline, the above-mentioned target compound was obtained.

NMR (DMSO-d$_6$) δ ppm: 1.94, 1.95 (2s, 6H), 2.94 (dd, 1H, Jgem=16.83 Hz, J=8.90 Hz), 3.16 (dd, 1H, J=3.96 Hz), 4.33 (dd, 1H), 7.82 (s, 2H), 10.54 (brs, 1H), 11.71 (brs, 1H).

EXAMPLE 54

Production of 2-isopropylidenehydrazono-5-[N-(3,4-methylenedioxyphenyl)carbamoylmethyl]thiazolidin-4-one By following the similar procedure to the above Example 9 but substituting the ethyl 4-aminobenzoate with 3,4-methylenedioxyaniline, the above-mentioned target compound was obtained.

NMR (DMSO-d$_6$) δ ppm: 1.94, 1.95 (2s, 6H), 2.83 (dd, 1H, Jgem=16.33 Hz, J=9.40 Hz), 3.12 (dd, 1H, J=3.80 Hz), 4.31 (dd, 1H), 5.97 (s, 2H), 6.82–6.97 (m, 3H), 7.28 (s, 1H), 10.17 (s, 1H).

EXAMPLE 55

Production of 2-isopropylidenehydrazono-5-[N-(1-naphthyl)carbamoylmethyl]thiazolidin-4-one By following the similar procedure to the above Example 9 but substituting the ethyl 4-aminobenzoate with 1-naphthylamine, the above-mentioned target compound was obtained.

NMR (DMSO-d$_6$) δ ppm: 1.95 (s, 6H), 3.03 (dd, 1H, Jgem=16.17 Hz, J=9.57 Hz), 4.39 (dd, 1H, J=3.63 Hz), 7.46–8.12 (m, 7H), 10.10 (brs, 1H), 11.71 (brs, 1H).

EXAMPLE 56

Production of 5-[N-(3,5-dichlorophenyl)carbamoylmethyl]-2-isopropylidenehydrazonothiazolidin-4-one By following the similar procedure to the above Example 9 but substituting the ethyl 4-aminobenzoate with 3,5-dichloroaniline, the above-mentioned target compound was obtained.

NMR (DMSO-d$_6$) δ ppm: 1.94, 1.95 (2s, 6H), 2.92 (dd, 1H, Jgem=16.82 Hz, J=8.91 Hz), 3.16 (dd, 1H, J=3.96 Hz), 4.33 (dd, 1H), 7.28 (t, 1H), 7.61 (s, 1H), 7.62 (s, 1H), 10.47 (s, 1H), 11.72 (brs, 1H).

EXAMPLE 57

Production of 2-isopropylidenehydrazono-5-(N-methyl-N-phenyl-carbamoylmethyl)thiazolidin-4-one By following the similar procedure to the above Example 9 but substituting the ethyl 4-aminobenzoate with N-methylaniline, the above-mentioned target compound was obtained.

NMR (CDCl$_3$) δ ppm: 1.98, 2.02 (2s, 6H), 2.55 (dd, 1H, Jgem=17.16 Hz, J=10.56 Hz), 2.99 (dd, 1H, J=3.30 Hz), 3.29 (s, 3H), 4.29 (dd, 1H), 7.16–7.45 (m, 5H).

EXAMPLE 58

Production of 2-isopropylidenehydrazono-5-[N-(3-pyridylmethyl)carbamoylmethyl]thiazolidin-4-one By following the similar procedure to the above Example 9 but substituting the ethyl 4-aminobenzoate with 3-aminomethylpyridine, the above-mentioned target compound was obtained.

NMR (DMSO-d$_6$) δ ppm: 1.94 (2s, 6H), 2.68 (dd, 1H, Jgem=16.17 Hz, J=9.57 Hz), 2.98 (dd, 1H, J=3.96 Hz), 4.26 (dd, 1H), 4.31 (d, 2H, J=5.94 Hz), 7.32–8.48 (m, 4H), 8.61 (t, 1H), 11.66 (brs, 1H).

EXAMPLE 59

Production of 2-isopropylidenehydrazono-5-[N-(3-imidazol-1-yl)propylcarbamoylmethyl]thiazolidin-4-one By following the similar procedure to the above Example 9 but substituting the ethyl 4-aminobenzoate with 1-(3-aminopropyl)imidazole, the above-mentioned target compound was obtained.

NMR (DMSO-d$_6$) δ ppm: 1.76–1.99 (m, 8H), 2.60 (dd, 1H, J=9.57 Hz, J=14.84 Hz), 2.90 (dd, 1H, J=3.96 Hz, J=15.84 Hz), 3.00–3.48 (m, 2H), 3.96 (t, 2H, J=6.93 Hz), 4.24 (dd, 1H, J=3.96 Hz, J=9.24 Hz), 6.88 (s, 1H), 7.16 (S, 1H), 7.61 (s, 1H), 8.10 (t, 1H, J=5.28 Hz), 11.65 (brs, 1H).

EXAMPLE 60

Production of 2-isopropylidenehydrazono-5-(N-morpholinocarbamoylmethyl)thiazolidin-4-one By following the similar procedure to the above Example 9 but substituting the ethyl 4-aminobenzoate with N-aminomorpholine, the above-mentioned target compound was obtained.

NMR (DMSO-d$_6$) δ ppm: 1.93, 1.94 (2s, 6H), 2.72 (m, 4H), 2.82 (m, 1H), 2.85 (m, 1H), 3.60 (m, 4H), 4.19 (m, 1H), 8.77, 9.10 (2s, 1H), 11.64 (brs, 1H).

EXAMPLE 61

Production of 2-isopropylidenehydrazono-5-[N-(2-thienylmethyl)carbamoylmethyl]thiazolidin-4-one By following the similar procedure to the above Example 9 but substituting the ethyl 4-aminobenzoate with 2-thienylmethylamine, the above-mentioned target compound was obtained.

NMR (DMSO-d$_6$) δ ppm: 1.94 (2s, 6H), 2.62 (dd, 1H, Jgem=16.16 Hz, J=9.90 Hz), 2.94 (dd, 1H, J=3.63 Hz), 4.24 (dd, 1H), 4.43 (m, 2H), 6.93–7.40 (m, 3H), 8.64 (t, 1H), 11.64 (brs, 1H).

EXAMPLE 62

Production of 2-isopropylidenehydrazono-5-[N-(4-morpholinophenyl)carbamoylmethyl]thiazolidin-4-one By following the similar procedure to the above Example 9 but substituting the ethyl 4-aminobenzoate with 4-morpholinoaniline, the above-mentioned target compound was obtained.

NMR (DMSO-d₆) δ ppm: 1.93, 1.94 (2s, 6H), 2.81 (dd, 1H, Jgem=16.16 Hz, J=9.57 Hz), 3.03 (m, 4H), 3.11 (dd, 1H, J=3.63 Hz), 3.72 (m, 4H), 4.30 (dd, 1H), 6.88, 7.42 (2d, 4H, phenyl), 9.90 (s, 1H), 11.67 (brs, 1H).

EXAMPLE 63

Production of 2-isopropylidenehydrazino-4-(3-pyridyl)thiazole

By following the similar procedure to the above Example 17 but substituting the chloroacetone with 3-bromoacetylpyridine, the above-mentioned target compound was obtained.

NMR (DMSO-d₆) δ ppm: 1.94, 1.96 (2s, 6H), 7.40–9.03 (m, 4H, pyridyl), 10.74 (brs, 1H).

EXAMPLE 64

Production of 4-(4-carboxyphenyl)-2-isopropylidenehydrazinothiazole

By following the similar procedure to the above Example 17 but substituting the chloroacetone with 4-bromoacetylbenzoic acid, the above-mentioned target compound was obtained.

NMR (DMSO-d₆) δ ppm: 1.94, 1.96 (2s, 6H), 7.43 (s, 1H), 7.96 (d, 4H, phenyl).

EXAMPLE 65

Production of 2-isopropylidenehydrazono-5-[N-(1-phenylethyl)carbamoylmethyl]thiazolidin-4-one By following the similar procedure to the above Example 9 but substituting the ethyl 4-aminobenzoate with α-methylbenzylamine, the above-mentioned target compound was obtained.

NMR (DMSO-d₆) δ ppm: 1.32, 1.35 (2s, 3H), 1.93, 1.94 (2s, 6H), 2.56–2.68 (m, 1H), 2.92–3.00 (m, 1H), 4.18–4.22 (m, 1H), 4.88–4.93 (m, 1H), 7.20–7.31 (m, 5H, phenyl), 8.46–8.49 (m, 1H), 11.62 (brs, 1H).

EXAMPLE 66

Production of 5-(4-benzyloxybenzyl)-2-hydrazonoimidazolidin-4-one

To 5.3 g of 5-(4-benzyloxybenzyl)-2-isopropylidenehydrazonoimidazolidin-4-one produced in the above Example 1 was added 54 ml of 0.5N hydrochloric acid and the obtained mixture was steam-distilled for 15 minutes. Then the reaction mixture was cooled and the white crystals thus precipitated were recovered by filtration. Thus 4.6 g of the above-mentioned target compound was obtained.

NMR (DMSO-d₆) δ ppm: 2.92–3.07 (m, 2H), 4.51–4.60 (brt, 1H), 5.05 (s, 2H), 6.92 (d, 2H, J=8.57 Hz), 7.10–7.17 (m, 2H), 7.29–7.47 (m, 5H), 9.66 (brs, 1H).

EXAMPLE 67

Production of 2-hydrazono-5-(N-phenylcarbamoylmethyl)thiazolidin-4-one

By following the similar procedure to the above Example 66 but using 2-isopropylidenehydrazono-5-(N-phenylcarbamoyl)thiazolidin-4-one produced in the above Example 33 as a starting material, the above-mentioned target compound was obtained.

NMR (DMSO-d₆) δ ppm: 2.84–2.94 (m, 1H), 3.14–3.30 (m, 1H), 4.36–4.42 (m, 1H), 7.05 (t, 1H, J=7.25 Hz), 7.30 (t, 2H, J=7.92 Hz), 7.55 (d, 2H, J=8.25 Hz), 10.13 (s, 1H), 11.77 (d, 1H, J=13.85 Hz).

EXAMPLE 68

Production of 2-isopropylidenehydrazono-5-[N-(2-methyl-5-methoxycarbonylphenyl)carbamoylmethyl]thiazolidin-4-one By following the similar procedure to the above Example 9 but substituting the ethyl 4-aminobenzoate with methyl 3-amino-4-methylbenzoate, the above-mentioned target compound was obtained.

NMR (DMSO-d₆) δ ppm: 1.95 (s, 6H), 2.28 (s, 3H), 2.92 (dd, 1H, Jgem=16.49 Hz, J=9.24 hz), 3.25 (dd, 1H, J=3.96 Hz), 3.84 (s, 3H), 4.34 (dd, 1H), 7.35–8.09 (m, 3H, phenyl), 9.60 (brs, 1H), 11.70 (brs, 1H).

EXAMPLE 69

Production of 2-isopropylidenehydrazino-4-trifluoromethylthiazole

By following the similar procedure to the above Example 17 but substituting the chloroacetone with 1-bromo-3,3,3-trifluoroacetone, the above-mentioned target compound was obtained.

NMR (CDCl₃) δ ppm: 1.87 (s, 3H), 2.05 (s, 3H), 7.07 (t, 1H), 8.54 (brs, 1H).

EXAMPLE 70

Production of 4-ethoxycarbonylmethyl-2-isopropylidenehydrazinothiazole

By following the similar procedure to the above Example 17 but substituting the chloroacetone with ethyl 4-chloroacetoacetate, the above-mentioned target compound was obtained.

NMR (CDCl₃) δ ppm: 1.26 (t, 3H), 1.86 (s, 3H), 2.04 (s, 3H), 3.59 (2s, 2H), 4.18 (q, 2H) 6.45 (s, 1H).

EXAMPLE 71

Production of 4-carboxymethyl-2-isopropylidenehydrazinothiazole

By following the similar procedure to the above Example 14 but using 4-ethoxycarbonylmethyl-2-isopropylidenehydrazinothiazole produced in the above Example 70 as a starting material, the above-mentioned target compound was obtained.

NMR (DMSO-d₆) δ ppm: 1.88 (s, 3H), 1.92 (s, 3H), 3,46 (s, 2H), 6.49 (s, 1H), 11.34 (brs, 1H).

EXAMPLE 72

Production of 2-cyclopentylidenehydrazono-5-(4-benzyloxybenzyl)imidazolidin-4-one 100 Milligrams of 5-(4-benzyloxybenzyl)-2-hydrazonoimidazolidin-4-one hydrochloride produced in the above Example 66 was dissolved in 10 ml of methanol and 82 mg of cyclopentanone was added thereto. After stirring at room temperature for 1 hour, the reaction mixture was concentrated under reduced pressure and the residue was purified by silica gel column chromatography (eluent: chloroform:methanol=60:1). Thus 87 mg of the above-mentioned target compound was obtained as white crystals.

NMR (DMSO-d₆) δ ppm: 1.65–1.68 (m, 4H), 2.26–2.32 (m, 4H), 2.85 (dd, 1H, J=4.29 Hz, J=13.86 Hz), 2.94 (dd, 1H, J=4.94 Hz, J=14.18 Hz), 4.17 (brt, 1H), 5.03 (s, 2H), 6.88 (d, 2H, J=8.25 Hz), 7.10 (d, 2H, J=8.58 Hz), 7.29–7.45 (m, 5H), 7.60 (brs, 1H), 10.55 (brs, 1H).

EXAMPLE 73

Production of 2-dicylopropylmethylenehydrazono-5-(N-phenylcarbamoylmethyl)thiazolidin-4-one By following the similar procedure to the above Example 72 but using 2-hydrazono-5-(N-phenylcarbamoylmethyl) thiazolidin-4-one hydrochloride produced in the above Example 67 as a starting material, the above-mentioned target compound was obtained.

NMR (DMSO-d₆) δ ppm: 0.61–1.09 (m, 10H), 2.86 (dd, 1H, J=9.90 Hz, J=16.83 Hz), 3.17 (dd, 1H, J=3.63 Hz, J=16.50 Hz), 4.29 (dd, 1H, J=3.63 Hz, J=9.57 Hz), 7.05 (t, 1H, J=7.26 Hz), 7.30 (t, 2H, J=7.59 Hz), 7.56 (d, 2H, J=7.59 Hz), 10.10 (s, 1H), 11.67 (brs, 1H).

EXAMPLE 74

Production of 2-cyclohexylmethylenehydrazono-5-(N-phenylcarbamoylmethyl)thiazolidin-4-one By following the similar procedure to the above Example 72 but using 2-hydrazono-5-(N-phenylcarbamoylmethyl) thiazolidin-4-one hydrochloride produced in the above Example 67 and cyclohexane carboxaldehyde as starting materials, the above-mentioned target compound was obtained.

NMR (DMSO-d₆) δ ppm: 1.07–1.76 (m, 10H), 2.18–2.26 (m, 1H), 2.85 (dd, 1H, J=9.90, 16.83 Hz), 3.17 (dd, 1H, J=3.30 Hz, J=16.17 Hz), 4.34 (dd, 1H, J=3.30 Hz, J=9.23 Hz), 7.00–7.61 (m, 6H), 10.11 (s, 1H), 11.78 (brs, 1H).

EXAMPLE 75

Production of 5-(4-benzyloxycarbonylaminobutyl)-2-isopropylidenehydrazonoimidazolidin-4-one (compound A) and 2-isopropylidenehydrazono-5-(4-methoxycarbonylaminobutyl)imidazolidin-4-one (compound B)

By following the similar procedure to the above Example 1 but substituting the O-benzyl-L-tyrosine methyl ester hydrochloride with $N^\varepsilon$-benzyloxycarbonyl-L-lysine methyl ester hydrochloride, the above-mentioned target compounds were obtained.

Compound A:

Rf value: 0.54 (dichloromethane:methanol=9:1).

NMR (DMSO-d₆) δ ppm: 1.25–1.71 (m, 6H), 1.88 (s, 3H), 1.93 (s, 3H), 2.94–2.99 (m, 2H), 3.89 (t, 1H, J=4.95 Hz), 5.00 (s, 2H), 7.22 (m, 6H), 7.47 (s, 1H), 10.67 (brs, 1H).

Compound B:

Rf values: 0.48 (dichloromethane:methanol=9:1).

NMR (DMSO-d₆) δ ppm: 1.25–1.70 (m, 6H), 1.87 (s, 3H), 1.93 (s, 3H), 2.91–2.95 (m, 2H), 3.50 (s, 1H), 3.89 (t, 1H, J=4.95 Hz), 7.08 (brs, 1H), 7.45 (brs, 1H), 10.67 (brs, 1H).

EXAMPLE 76

Production of 2-isopropylidenehydrazono-5-(2-methylpropyl)imidazolidin-4-one

By following the similar procedure to the above Example 1 but substituting the O-benzyl-L-tyrosine methyl ester hydrochloride with L-leucine methyl ester hydrochloride, the above-mentioned target compound was obtained.

NMR (DMSO-d₆) δ ppm: 0.87 (s, 3H), 0.89 (s, 3H), 1.86–1.94 (m, 1H), 1.88 (s, 3H), 1.93 (s, 3H), 3.88 (t, 1H, J=4.61 Hz), 7.52 (s, 1H), 10.63 (brs, 1H).

EXAMPLE 77

Production of 5-isopropyl-2-isopropylidenehydrazonoimidazolidin-4-one

By following the similar procedure to the above Example 1 but substituting the O-benzyl-L-tyrosine methyl ester hydrochloride with L-valine methyl ester hydrochloride, the above-mentioned target compound was obtained.

NMR (DMSO-d₆) δ ppm: 0.83 (d, 3H, J=6.59 Hz), 0.93 (d, 3H, J=6.93 Hz), 1.89–2.06 (m, 1H), 1.88 (s, 3H), 1.94 (s, 3H), 3.81 (d, 1H, J=2.97 Hz), 7.41 (brs, 1H), 10.80 (brs, 1H).

EXAMPLE 78

Production of 2-isopropylidenehydrazono-5-[2-(N-phenylcarbamoyl)ethyl]imidazolidin-4-one (Step I)

10 Grams of α-methyl $N^\alpha$-tert-butyloxycarbonyl-L-glutamate [Muraki and Mizoguchi, Chem. Pharm. Bull., 19, 1708 (1971)], 4.28 g of aniline and 6.21 g of N-hydroxybenztriazole were dissolved in 50 ml of dimethylformamide. Under ice-cooling, water-soluble carbodiimide was added thereto and the obtained mixture was stirred at room temperature for 18 hours. The reaction mixture was poured into a mixture of ethyl acetate with water (each 250 ml portion) and distribute between aqueous and organic layers. The organic layer was successively washed with 1% hydrochloric acid, a saturated aqueous solution of sodium hydrogencarbonate and a saturated aqueous solution of sodium chloride and dried over anhydrous sodium sulfate. After distilling off the solvent under reduced pressure, the residual solid was recrystallized from a mixture of ethyl acetate with n-hexane. Thus 1.48 g of $N^\alpha$-tert-butyloxycarbonyl-L-(γ-phenyl)glutamine methyl ester was obtained.

NMR (CDCl₃) δ ppm: 1.46 (s, 9H), 1.94 (m, 1H), 2.32 (m, 1H), 2.46 (m, 2H), 3.74 (s, 3H), 4.38 (m, 1H), 5.36 (brs, 1H), 7.07–7.60 (m, 5H), 8.52 (brs, 1H).

(Step II)

11.42 Grams of the compound produced in the above Step I was added to 35 ml of a 4.5N solution of hydrogen chloride in ethyl acetate and stirred at room temperature for 20 minutes. The reaction mixture was concentrated under reduced pressure and thus 8.9 g of L-(γ-phenyl)glutamine methyl ester hydrochloride was obtained.

NMR (DMSO-d₆) δ ppm: 2.13 (m, 2H), 2.59 (m, 2H), 3.74 (s, 3H), 4.06 (m, 1H), 7.00–7.62 (m, 5H), 8.63 (brs, 3H).

(Step III)

By following the similar procedure to the above Example 1 but using the L-(γ-phenyl)glutamine methyl ester hydrochloride obtained in the above Step II as a starting material, the above-mentioned target compound was obtained.

NMR (DMSO-d₆) δ ppm: 1.88 (s, 3H), 1.93 (s, 3H), 1.87–2.06 (m, 2H), 2.26–2.48 (m, 2H), 4.09 (dd, 1H, J=5.28 Hz, J=10.56 Hz), 7.01 (t, 1H, J=7.26 Hz), 7.27 (t, 2H, J=7.59 Hz), 7.59 (d, 2H, J=7.59 Hz), 9.92 (s, 1H), 10.77 (brs, 1H).

EXAMPLE 79

Production of 5-benzyloxycarbonylmethyl-2-isopropylidenehydrazonoimidazolidin-4-one (compound C) and 2-isopropylidenehydrazono-5-methoxycarbonylmethylimidazolidin-4-one (compound D)

By following the similar procedure to the above Example 1 but substituting the O-benzyl-L-tyrosine methyl ester hydrochloride with α-methyl L-aspartate hydrochloride and β-benzyl L-aspartate hydrochloride, the above-mentioned target compounds were obtained.

Compound C:

Rf value: 0.60 (dichloromethane:methanol=9:1).

NMR (DMSO-$d_6$) δ ppm: 1.88 (s, 3H), 1.93 (s, 3H), 2.76 (d, 2H, J=5.61 Hz), 4.19 (t, 1H, J=5.28 Hz), 5.09 (s, 2H), 7.31–7.41 (m, 6H), 10.65 (brs, 1H).

Compound D:

Rf value: 0.51 (dichloromethane:methanol=9:1).

NMR (CDCl$_3$) δ ppm: 2.02 (s, 3H), 2.12 (s, 3H), 2.54 (dd, 2H, J=10.56 Hz, J=17.49 Hz), 3.03 (dd, 1H, J=2.97 Hz, J=17.49 Hz), 3.74 (s, 3H), 4.28 (dd, 1H, J=2.64 Hz, J=10.56 Hz).

EXAMPLE 80

Production of 5-carboxymethyl-2-isopropylidenehydrazonoimidazolidin-4-one

By following the similar procedure to the above Example 14 but using 2-isopropylidenehydrazono-5-methoxycarbonylmethylimidazolidin-4-one produced in the above Example 79 as a starting material, the above-mentioned target compound was obtained.

NMR (DMSO-$d_6$) δ ppm: 1.88 (s, 3H), 1.92 (s, 3H), 2.61 (dd, 2H, J=0.99 Hz, J=4.95 Hz), 4.13 (t, 1H, J=5.28 Hz), 7.29 (brs, 1H), 11.55 (brs, 1H).

EXAMPLE 81

Production of 2-isopropylidenehydrazono-5-(N-phenylcarbamoylmethyl)imidazolidin-4-one By following the similar procedure to the above Example 9 but using 5-carboxymethyl-2-isopropylidenehydrazonoimidazolidin-4-one produced in the above Example 80 and aniline as starting materials, the above-mentioned target compound was obtained.

NMR (DMSO-$d_6$) δ ppm: 1.88 (s, 3H), 1.91 (s, 3H), 2.63 (dd, 2H, J=6.92, 15.50 Hz), 2.81 (dd, 1H, J=4.95, 15.83 Hz), 4.24 (t, 1H, J=5.28 Hz), 7.03 (t, 2H, J=7.26 Hz), 7.29 (t, 2H, J=7.59 Hz), 7.58 (d, 2H, J=7.59 Hz), 10.01 (s, 1H), 10.74 (brs, 1H).

EXAMPLE 82

Production of 5-(N-cyclopropylcarbamoylmethyl)-2-isopropylidenehydrazonoimidazolidin-4-one By following the similar procedure to the above Example 9 but using 5-carboxymethyl-2-isopropylidenehydrazonoimidazolidin-4-one produced in the above Example 80 and cyclopropylamine as starting materials, the above-mentioned target compound was obtained.

NMR (DMSO-$d_6$) δ ppm: 0.50–0.82 (m, 4H), 2.01 (s, 3H), 2.07 (s, 3H), 2.37 (dd, 1H, J=10.23 Hz, J=15.51 Hz), 2.59–2.73 (m, 1H), 2.91 (dd, 1H, J=2.97 Hz, J=15.84 Hz), 4.29 (dd, 1H, J=2.97 Hz, J=9.90 Hz).

EXAMPLE 83

Production of 5-(4-benzyloxybenzyl)-2-(4-bromobenzenesulfonohydrazonoimidazolidin-4-one 173 Milligrams of 5-(4-benzyloxybenzyl)-2-hydrazonoimidazolidin-4-one hydrochloride produced in the above Example 66 was dissolved in a solvent mixture comprising 10 ml of tetrahydrofuran with 5 ml of water. Under ice-cooling, 42 mg of sodium hydrogencarbonate and 180 mg of 4-bromobenzenesulfonyl chloride were successively added thereto and the obtained mixture was stirred at the same temperature for 30 minutes and then at room temperature for 1 hour. The reaction mixture was concentrated under reduced pressure and the residue was distributed between aqueous and organic layers by adding water and dichloromethane thereto. The organic layer was dried over anhydrous magnesium sulfate and concentrated again under reduced pressure. The residue was charged on silica gel column chromatography and eluted with a solvent mixture of chloroform and methanol (50:1 (v/v)). Thus 82 mg of the above-mentioned target compound was obtained.

NMR (DMSO-$d_6$) δ ppm: 2.87 (dd, 1H, J=4.61 Hz, J=14.18 Hz), 2.93 (dd, 1H, J=4.95 Hz, J=14.19 Hz), 4.06 (brt, 1H), 5.05 (s, 2H), 5.91 (s, 1H), 6.80 (d, 2H, J=8.58 Hz), 6.99 (d, 2H, J=8.25 Hz), 7.33–7.49 (m, 5H), 7.74–7.85 (m, 4H), 8.93 (s, 1H).

EXAMPLE 84

Production of 2-(4-acetoamidobenzenesulfonohydrazono)-5-(4-benzyloxybenzyl)imidazolidin-4-one By following the similar procedure to the above Example 83 but substituting the 4-bromobenzenesulfonyl chloride with 4-acetoamidobenzenesulfonyl chloride, the above-mentioned target compound was obtained.

NMR (DMSO-$d_6$) δ ppm: 2.05 (s, 3H), 2.78 (dd, 1H, J=4.94 Hz, J=14.18 Hz), 2.93 (dd, 1H, J=4.94 Hz, J=14.18 Hz), 4.05 (t, 1H, J=4.95 Hz), 5.02 (s, 2H), 5.76 (s, 1H), 6.81 (d, 2H, J=8.58 Hz), 7.02 (d, 2H, J=8.58 Hz), 7.31–7.45 (m, 5H), 7.73 (d, 2H, J=9.24 Hz), 7.86 (d, 2H, J=8.91 Hz), 8.78 (s, 1H), 10.39 (s, 1H).

EXAMPLE 85

Production of 2-isopropylidenehydrazono-5-[N-(1-phenylethyl)carbamoylmethyl]imidazolidin-4-one By following the similar procedure to the above Example 9 but using 5-carboxymethyl-2-isopropylidenehydrazonoimidazolidin-4-one produced in the above Example 80 and α-methylbenzylamine as starting materials, the above-mentioned target compound was obtained.

NMR (DMSO-$d_6$) δ ppm: 1.34 (d, 3H, J=6.93 Hz), 1.88 (s, 3H), 1.91 (s, 3H), 2.36–2.49 (m, 1H), 2.51–2.68 (m, 1H), 4.15 (brt, 1H), 4.88–4.91 (m, 1H), 7.08 (d, 1H, J=27.71 Hz), 7.18–7.31 (m, 5H), 8.38 (d, 1H, J=7.59 Hz), 10.73 (brs, 1H).

EXAMPLE 86

Production of 5-(4-imidazolylmethyl)-2-isopropylidenehydrazonoimidazolidin-4-one By following the similar procedure to the above Example 1 but substituting the O-benzyl-L-tyrosine methyl ester hydrochloride with L-histidine methyl ester dihydrochloride, the above-mentioned target compound was obtained.

NMR (DMSO-$d_6$) δ ppm: 1.87 (s, 3H), 1.92 (s, 3H), 2.75 (dd, 1H, J=6.93 Hz, J=14.85 Hz), 2.97 (dd, 1H, J=4.29 Hz, J=14.84 Hz), 4.14 (dd, 1H, J=4.62 Hz, J=6.93 Hz), 6.80 (s, 1H), 7.26 (s, 1H), 7.54 (s, 1H), 10.70 (brs, 1H).

EXAMPLE 87

Production of 2-isopropylidenehydrazono-5-[N-(2-methoxycarbonylphenyl)carbamoylmethyl]thiazolidin-4-one By following the similar procedure to the above Example 9 but substituting the ethyl 4-aminobenzoate with methyl 2-aminobenzoate, the above-mentioned target compound was obtained.

NMR (DMSO-$d_6$) δ ppm: 1.93 (s, 3H), 1.94 (s, 3H), 2.99 (dd, 1H, Jgem=16.49 Hz, J=9.24 Hz), 3.17 (dd, 1H, J=3.62 Hz), 3.84 (s, 3H), 4.32 (dd, 1H), 7.19–8.09 (m, 4H, phenyl), 10.56 (brs, 1H), 11.71 (brs, 1H).

EXAMPLE 88

Production of 5-[N-(2-carboxyphenyl)carbamoylmethyl]-2-isopropylidenehydrazonothiazolidin-4-one By following the similar procedure to the above Example 14 but using 2-isopropylidenehydrazono-5-[N-(2-methoxycarbonylphenyl)carbamoylmethyl]thiazolidin-4-one produced in the above Example 87 as a starting material, the above-mentioned target compound was obtained.

NMR (DMSO-$d_6$) δ ppm: 1.94 (s, 3H), 1.95 (s, 3H), 3.04 (dd, 1H, Jgem=16.67 Hz, J=8.91 Hz), 3.22 (dd, 1H, J=3.96 Hz), 4.34 (dd, 1H), 7.14–8.39 (m, 4H, phenyl), 11.14 (brs, 1H), 11.90 (brs, 1H).

EXAMPLE 89

Production of 5-[N-(5-carboxy-2-methylphenyl)carbamoylmethyl]-2-isopropylidenehydrazonothiazolidin-4-one By following the similar procedure to the above Example 14 but using 2-isopropylidenehydrazono-5-[N-(5-methoxycarbonyl-2-methylphenyl)carbamoylmethyl]thiazolidin-4-one produced in the above Example 68 as a starting material, the above-mentioned target compound was obtained.

NMR (DMSO-$d_6$) δ ppm: 1.95 (s, 6H), 2.27 (s, 3H), 2.91 (dd, 1H, Jgem=16.50 Hz, J=9.57 Hz), 3.24 (dd, 1H, J=3.63 Hz), 4.34 (dd, 1H), 7.32–8.09 (m, 3H), 9.59 (brs, 1H), 12.00 (brs, 1H).

EXAMPLE 90

Production of 5-[N-(3,4-dimethoxyphenyl)carbamoylmethyl]-2-isopropylidenehydrazonothiazolidin-4-one By following the similar procedure to the above Example 9 but substituting the ethyl 4-aminobenzoate with 3,4-dimethoxyaniline, the above-mentioned target compound was obtained.

NMR (DMSO-$d_6$) δ ppm: 1.94 (s, 3H), 1.95 (s, 3H), 2.83 (dd, 1H, Jgem=16.49 Hz, J=9.57 Hz), 3.12 (dd, 1H, J=3.96 Hz), 3.71 (s, 3H), 3.72 (s, 3H), 4.31 (dd, 1H), 6.86–7.29 (m, 3H), 9.98 (brs, 1H), 11.69 (brs, 1H).

EXAMPLE 91

Production of 3-ethoxycarbonylmethyl-5-(N-phenylcarbamoylmethyl)-2-isopropylidenehydrazonothiazolidin-4-one By following the similar procedure to the above Example 9 but using the compound obtained in the above Example 15 and aniline, the above-mentioned target compound was obtained.

NMR (DMSO-$d_6$) δ ppm: 1.20 (t, 3H), 1.92 (s, 3H), 1.95 (s, 3H), 2.87 (dd, 1H, J=9.90 Hz), 4.15 (q, 2H), 4.46 (d, 2H, J=2.97 Hz), 4.54 (dd, 1H, J=3.63 Hz), 7.03–7.57 (m, 5H, phenyl), 10.16 (brs, 1H).

EXAMPLE 92

Production of 2-isopropylidenehydrazino-4-(3-thienyl)thiazole

By following the similar procedure to the above Example 17 but substituting the chloroacetone with 3-bromoacetylthiophene, the above-mentioned target compound was obtained.

NMR (CDCl$_3$) δ ppm: 1.85 (s, 3H), 2.04 (s, 3H), 6.72 (s, 1H), 7.00–7.33 (m, 3H, thienyl), 8.66 (brs, 1H).

EXAMPLE 93

Production of 4-[N-(3,4-dimethoxyphenyl)carbamoylmethyl]-2-isopropylidenehydrazinothiazole By following the similar procedure to the above Example 9 but using 4-carboxymethyl-2-isopropylidenehydrazinothiazole produced in the above Example 71 and 3,4-dimethoxyaniline as starting materials, the above-mentioned target compound was obtained.

NMR (DMSO-$d_6$) δ ppm: 1.88 (s, 3H), 1.92 (s, 3H), 3.52 (brs, 2H), 3.71 (s, 6H), 6.51 (brs, 1H), 6.86–7.33 (m, 3H), 9.92 (brs, 1H), 10.46 (brs, 1H).

EXAMPLE 94

Production of 2-isopropylidenehydrazino-4-(2-thiazolyl)thiazole

By following the similar procedure to the above Example 17 but substituting the chloroacetone with 3-bromoacetylthiazole, the above-mentioned target compound was obtained.

NMR (DMSO-$d_6$) δ ppm: 1.94 (s, 3H), 1.96 (s, 3H), 7.39 (s, 1H), 7.69 (d, 1H, J=3.13 Hz), 7.85 (d, 1H), 10.88 (brs, 1H).

EXAMPLE 95

Production of 2-isopropylidenehydrazono-5-[N-(2-methoxycarbonyl-4-methylphenyl)carbamoylmethyl]imidazolidin-4-one By following the similar procedure to the above Example 9 but using 5-carboxymethyl-2-isopropylidenehydrazinoimidazolidin-4-one produced in the above Example 80 and methyl 2-amino-5-methylbenzoate as starting materials, the above-mentioned target compound was obtained.

NMR (CDCl$_3$) δ ppm: 2.02 (s, 3H), 2.08 (s, 3H), 2.34 (s, 3H), 2.66 (dd, 1H, J=10.89 Hz, J=16.49 Hz), 3.21 (dd, 1H, J=2.31 Hz, J=16.50 Hz), 3.92 (s, 3H), 4.44 (dd, 1H, J=2.31 Hz, J=10.89 Hz), 6.87 (s, 1H), 7.26 (s, 1H), 7.37 (dd, 1H, J=1.97 Hz, J=8.57 Hz), 7.84 (brs, 1H), 8.51 (d, 1H, J=8.58 Hz), 11.07 (brs, 1H).

EXAMPLE 96

Production of 5-[N-(1-ethoxycarbonyl-3-methylbutyl)carbamoylmethyl]-2-isopropylidenehydrazonothiazolidin-4-one By following the similar procedure to the above Example 9 but substituting the ethyl 4-aminobenzoate with L-leucine ethyl ester, the above-mentioned target compound was obtained.

NMR (DMSO-d$_6$) δ ppm: 0.82–0.91 (m, 6H), 1.15–1.22 (m, 3H), 1.44–1.91 (m, 3H), 1.94 (brs, 6H), 2.63 (ddd, 1H, J=2.31 Hz, J=10.22 Hz, J=16.16 Hz), 2.95 (dd, 1H, J=3.30 Hz, J=16.16 Hz), 4.03–4.12 (m, 2H), 4.13–4.24 (m, 2H), 8.43 (dd, 1H, J=5.27 Hz, J=7.58 Hz), 11.65 (brs, 1H).

EXAMPLE 97

Production of 5-[N-(3-ethoxycarbonylphenyl) carbamoylmethyl]-2-isopropylidenehydrazonothiazolidin-4-one By following the similar procedure to the above Example 9 but substituting the ethyl 4-aminobenzoate with ethyl 3-aminobenzoate, the above-mentioned target compound was obtained.

NMR (DMSO-d$_6$) δ ppm: 1.32 (t, 3H), 1.94 (s, 3H), 1.95 (s, 3H), 2.90 (dd, 1H, Jgem=1.65 Hz, J=9.24 Hz), 3.17 (dd, 1H, J=3.96 Hz), 4.25–4.37 (m, 3H), 7.15–8.25 (m, 4H, phenyl), 10.36 (brs, 1H), 11.70 (brs, 1H).

EXAMPLE 98

Production of 5-{N-[1-ethoxycarbonyl-2-(4-benzyloxyphenyl)ethyl]carbamoylmethyl}-2-isopropylidenehydrazonothiazolidin-4-one By following the similar procedure to the above Example 9 but substituting the ethyl 4-aminobenzoate with O-benzyl-L-tyrosine ethyl ester, the above-mentioned target compound was obtained.

NMR (DMSO-d$_6$) δ ppm: 1.11 (t, 3H, J=6.93 Hz), 1.93 (brs, 6H), 2.51–2.62 (m, 1H), 2.65–2.98 (m, 3H), 4.03 (q, 2H, J=7.26 Hz), 4.14 (dd, 0.5H, J=3.63 Hz, J=9.89 Hz), 4.18 (dd, 0.5H, J=3.63 hz, J=9.89 Hz), 4.31–4.40 (m, 1H), 5.06 (s, 2H), 6.92 (d, 2H, J=8.57 Hz), 7.13 (d, 2H, J=7.26 Hz), 7.14–7.44 (m, 5H), 8.52 (d, 1H, J=7.92 Hz), 11.65 (brs, 1H).

EXAMPLE 99

Production of 5-{N-[1-carboxy-2-(4-benzyloxyphenyl)ethyl]-carbamoylmethyl}-2-isopropylidenehydrazonothiazolidin-4-one By following the similar procedure to the above Example 14 but using 5-{N-[1-ethoxycarbonyl-2-(4-benzyloxyphenyl)ethyl]carbamoylmethyl}-2-isopropylidenehydrazonothiazolidin-4-one as a starting material, the above-mentioned target compound was obtained.

NMR (DMSO-d$_6$) δ ppm: 1.93 (brs, 6H), 2.53–2.65 (m, 1H), 2.75–3.01 (m, 3H), 4.15 (ddd, 1H, J=2.96 Hz, J=10.22 Hz, J=22.43 Hz), 4.30–4.34 (m, 1H), 5.05 (s, 2H), 6.90 (d, 2H, J=8.58 Hz), 7.12 (d, 2H, J=8.58 Hz), 7.29–7.44 (m, 5H), 8.27 (d, 1H, J=7.92 Hz).

EXAMPLE 100

Production of 2-isopropylidenehydrazono-5-{N-[1-methoxycarbonyl-2-(3-indolyl)ethyl]carbamoylmethyl}thiazolidin-4-one By following the similar procedure to the above Example 9 but substituting the ethyl 4-aminobenzoate with L-tryptophan methyl ester, the above-mentioned target compound was obtained.

NMR (CDCl$_3$) δ ppm: 1.93 (s, 1H), 1.98 (d, 3H, J=3.63 Hz), 2.51–2.60 (m, 1H), 2.89–2.97 (m, 1H), 3.21–3.24 (m, 2H), 4.13–4.17 (m, 1H), 4.84–4.90 (m, 1H), 6.79–7.10 (m, 2H), 7.23–7.35 (m, 2H), 7.67–7.73 (m, 1H), 8.89 (d, 1H, J=12.20 Hz).

EXAMPLE 101

Production of 5-[N-(1-carboxy-3-methylbutyl) carbamoylmethyl]-2-isopropylidenehydrazonothiazolidin-4-one By following the similar procedure to the above Example 14 but using 5-[N-(1-ethoxycarbonyl-3-methylbutyl) carbamoylmethyl]-2-isopropylidenehydrazonothiazolidin-4-one produced in the above Example 96 as a starting material, the above-mentioned target compound was obtained.

NMR (DMSO-d$_6$) δ ppm: 0.81–0.89 (m, 6H), 1.46–1.51 (m, 2H), 1.57–1.68 (m, 1H), 1.94 (brs, 6H), 2.49–2.66 (m, 1H), 2.95 (dd, 1H, J=3.30 Hz, J=16.49 Hz), 4.17–4.23 (m, 2H), 8.27 (dd, 1H, J=5.28 Hz, J=7.91 Hz).

EXAMPLE 102

Production of 5-{N-[1-carboxy-2-(3-indolyl)ethyl] carbamoylmethyl}-2-isopropylidenehydrazonothiazolidin-4-one By following the similar procedure to the above Example 14 but using 2-isopropylidenehydrazono-5-{N-[1-methoxycarbonyl-2-(3-indolyl)ethyl]carbamoylmethyl}-thiazolidin-4-one produced in the above Example 100 as a starting material, the above-mentioned target compound was obtained.

NMR (DMSO-d$_6$) δ ppm: 1.94 (brs, 6H), 2.53–2.67 (m, 1H), 2.89–3.24 (m, 3H), 4.18 (ddd, 1H, J=3.30 Hz, J=10.22 Hz, J=22.43 Hz), 4.44–4.51 (m, 1H), 6.95–7.15 (m, 3H), 7.33 (d, 1H, J=7.92 Hz), 7.53 (d, 1H, J=7.58 Hz), 8.38 (d, 1H, J=7.59 Hz), 10.85 (s, 1H), 11.76 (brs, 1H).

EXAMPLE 103

Production of 5-[N-(3-carboxyphenyl) carbamoylmethyl]-2-isopropylidenehydrazonothiazolidin-4-one By following the similar procedure to the above Example 14 but using 5-[N-(3-ethoxycarbonylphenyl) carbamoylmethyl]-2-isopropylidenehydrazonothiazolidin-4-one obtained the above Example 97 as a starting material, the above-mentioned target compound was obtained.

NMR (DMSO-d$_6$) δ ppm: 1.94 (s, 3H), 1.95 (s, 3H), 2.90 (dd, 1H, Jgem=16.50 Hz, J=9.24 Hz), 3.17 (dd, 1H, J=3.96 Hz), 4.34 (dd, 1H), 7.40–8.22 (m, 4H, phenyl), 10.32 (brs, 1H).

EXAMPLE 104

Production of 2-isopropylidenehydrazono-5-[N-(2-methoxycarbonylmethylphenyl)carbamoylmethyl] thiazolidin-4-one By following the similar procedure to the above Example 9 but substituting the ethyl 4-aminobenzoate with methyl 2-aminophenylacetate, the above-mentioned target compound was obtained.

NMR (DMSO-d$_6$) δ ppm: 1.94 (2s, 6H), 2.81 (dd, 1H, Jgem=16.17 Hz, J=9.90 Hz), 3.16 (dd, 1H, J=3.63 Hz), 3.60 (s, 3H), 3.68 (s, 2H), 4.29 (dd, 1H), 7.16–7.37 (m, 4H, phenyl), 9.60 (brs, 1H), 11.69 (brs, 1H).

EXAMPLE 105

Production of 5-[N-(2-carboxymethylphenyl) carbamoylmethyl]-2-isopropylidenehydrazonothiazolidin-4-one By following the similar procedure to the above Example 14 but using 2-isopropylidenehydrazino-5-[N-(2- methoxycarbonylmethylphenyl)carbamoylmethyl]thiazolidin-4-one obtained the above Example 104 as a starting material, the above-mentioned target compound was obtained.

NMR (DMSO-d$_6$) δ ppm: 1.94 (s, 6H), 2.83 (dd, 1H, Jgem=16.50 Hz, J=9.89 Hz), 3.17 (dd, 1H, J=3.63 Hz), 3.54 (s, 2H), 4.31 (dd, 1H), 7.07–8.20 (m, 6H), 10.33 (brs, 1H).

EXAMPLE 106

Production of 2-isopropylidenehydrazono-5(R)-(N-phenylcarbamoylmethyl)thiazolidin-4-one (Step 1)

1 Gram of methyl 2(S)-hydroxysuccinamate produced in accordance with a method described in Journal of the Organic Chemistry, 47, 4928 (1982) and 0.69 g of aniline were dissolved in a mixture of tetrahydrofuran with water (each 10 ml portion) and 2.59 g of water soluble carbodiimide hydrochloride was added thereto. Then the pH value of the mixture was maintained at 4 to 5 by adding 10% hydrochloric acid and the mixture was allowed to react at room temperature for 10 minutes. Next, the reaction mixture was extracted with 30 ml of ethyl acetate and the organic layer was washed with a saturated aqueous solution of sodium hydrogencarbonate and dried over anhydrous sodium sulfate. After distilling off the solvent under reduced pressure, 1.5 g of methyl 2(S)-hydroxy-N-phenylsuccinamate was obtained as an oily substance.

NMR (CDCl$_3$) δ ppm: 2.8–2.9 (m, 2H), 3.83 (s, 3H), 4.58 (dd, 1H, J=6.93 Hz, J=3.96 Hz), 7.08–7.51 (m, 5H, phenyl), 7.87 (brs, 1H).

(Step 2)

The compound produced in the above Step 1 was dissolved in 30 ml of methylene chloride. Under ice-cooling, 1.41 ml of triethylamine and 0.78 ml of methanesulfonyl chloride were added thereto and the obtained mixture was stirred under ice-cooling for 10 minutes. Then the reaction mixture was successively washed with 0.1N hydrochloric acid and a saturated aqueous solution of sodium chloride and dried over anhydrous sodium sulfate. After distilling off the solvent under reduced pressure, 1.82 g of methyl 2(S)-methanesulfonyloxy-N-phenylsuccinamate was obtained as an oily substance.

NMR (CDCL$_3$) δ ppm: 3.03–3.06 (m, 2H), 3.17 (s, 3H), 3.85 (s, 3H), 5.46–5.51 (m, 1H), 7.13–7.52 (m, 5H, phenyl), 7.58 (brs, 1H).

(Step 3)

The compound produced in the above Step 2 was dissolved in 20 ml of ethanol and 1.06 g of acetone thiosemicarbazone and 0.66 g of anhydrous sodium acetate were added thereto. The mixture thus obtained was refluxed under heating for 3 hours. Then the reaction mixture was allowed to cool and the solid thus formed was recovered by filtration, washed with water and recrystallized from methanol. Thus 0.56 g of the above-mentioned target compound was obtained as white crystals.

[α]$_D^{25}$=+2.61° (C=1.53, tetrahydrofuran)

The data of NMR (DMSO-d$_6$) were identical with those of the compound produced in the above Example 33.

EXAMPLE 107

Production of 2-isopropylidenehydrazono-5(S)-(N-phenylcarbamoylmethyl)thiazolidin-4-one By following the similar procedure to the above Example 106 but substituting the methyl 2(S)-hydroxysuccinamate with methyl 2(R)-hydroxysuccinamate, the above-mentioned target compound was obtained.

[α]$_D^{25}$=−2.58° (C=1.50 tetrahydrofuran)

The data of NMR (DMSO-d$_6$) were identical with those of the compound produced in the above Example 33.

EXAMPLE 108

Production of 5-[N-(4-chloro-2-methoxycarbonylphenyl)carbamoylmethyl]-2-isopropylidenehydrazonothiazolidin-4-one By following the similar procedure to Example 9 but substituting the ethyl 4-aminobenzoate with methyl 2-amino-5-chlorobenzoate, the above target compound was obtained.

NMR (DMSO-d$_6$) δ ppm: 1.93 (s, 3H), 1.94 (s, 3H), 2.98 (dd, 1H, Jgem=16.50 Hz, J=8.90 Hz), 3.20 (dd, 1H, J=3.96 Hz), 3.84 (s, 3H), 4.31 (dd, 1H), 7.65–8.06 (m, 3H, phenyl), 10.50 (brs, 1H), 11.71 (brs, 1H).

EXAMPLE 109

Production of 5-[N-(2-carboxy-4-chlorophenyl)carbamoylmethyl]-2-isopropylidenehydrazonothiazolidin-4-one By following the similar procedure to Example 14 but using 5-[N-(4-chloro-2-methoxycarbonylphenyl)carbamoylmethyl]-2-isopropylidenehydrazonothiazolidin-4-one produced in Example 108 as the starting compound, the above target compound was obtained.

NMR (DMSO-d$_6$) δ ppm: 1.93 (s, 3H), 1.95 (s, 3H), 2.98 (dd, 1H, Jgem=16.50 Hz, J=9.08 Hz), 3.17 (dd, 1H, J=3.96 Hz), 4.32 (dd, 1H), 7.49–8.40 (m, 3H, phenyl), 12.49 (brs, 1H).

EXAMPLE 110

Production of 2-isopropylidenehydrazono-5-[N-(2,3-dimethylphenyl)carbamoyl-methyl]thiazolidin-4-one By following the similar procedure to Example 9 but substituting the ethyl 4-aminobenzoate with 2,3-dimethylaniline, the above target compound was obtained.

NMR (DMSO-d$_6$) δ ppm: 1.94 (s, 6H), 2.06 (s, 3H), 2.24 (s, 3H), 2.85 (dd, 1H, J=9.90 Hz, J=16.17 Hz), 3.18 (dd, 1H, J=3.63 Hz, J=16.17 Hz), 4.32 (dd, 1H, J=3.95 Hz, J=9.56 Hz), 6.99–7.14 (m, 3H), 9.53 (s, 1H), 11.67 (s, 1H).

EXAMPLE 111

Production of 5-[N-(2-furanylmethyl)carbamoylmethyl]-2-isopropylidenehydrazonothiazolidin-4-one By following the similar procedure to Example 9 but substituting the ethyl 4-aminobenzoate with 2-furanylmethylamine, the above target compound was obtained.

NMR (DMSO-d$_6$) δ ppm: 1.94 (2s, 6H), 2.62 (dd, 1H, Jgem=16.17 Hz, J=9.57 Hz), 2.94 (dd, 1H, J=3.96 Hz), 4.21–4.34 (m, 3H), 6.25–7.58 (m, 3H), 8.50 (t, 1H, J=5.28 Hz), 11.71 (brs, 1H).

EXAMPLE 112

Production of 5-[N-(2,6-dimethylphenyl)carbamoylmethyl]-2-isopropylidenehydrazonothiazolidin-4-one By following the similar procedure to Example 9 but substituting the ethyl 4-aminobenzoate with 2,6-dimethylaniline, the above target compound was obtained.

NMR (DMSO-d$_6$) δ ppm: 1.95 (s, 6H), 2.13 (s, 6H), 2.85 (dd, 1H, J=9.57 Hz, J=16.17 Hz), 3.18 (dd, 1H, J=3.96 Hz, J=16.17 Hz), 4.33 (dd, 1H, J=3.63 Hz, J=9.56 Hz), 7.06 (s, 3H), 9.44 (s, 1H), 11.68 (brs, 1H).

EXAMPLE 113

Production of 2-isopropylidenehydrazono-5-[N-(2-methoxy-5-methoxycarbonylphenyl) carbamoylmethyl]thiazolidin-4-one By following the similar procedure to Example 9 but substituting the ethyl 4-aminobenzoate with methyl 3-amino-4-methoxybenzoate, the above target compound was obtained.

NMR (DMSO-d$_6$) δ ppm: 1.94 (s, 3H), 1.95 (s, 3H), 2.96 (dd, 1H, Jgem=16.82 Hz, J=8.91 Hz), 3.82 (s, 3H), 3.92 (s, 3H), 4.32 (dd, 1H, J=3.95 Hz), 7.15–8.62 (m, 3H, phenyl), 9.53 (brs, 1H), 11.69 (brs, 1H).

EXAMPLE 114

Production of 5-[N-(5-carboxy-2-methoxyphenyl) carbamoylmethyl]-2-isopropylidenehydrazonothiazolidin-4-one By following the similar procedure to Example 14 but using 2-isopropylidenehydrazono-5-[N-(2-methoxy-5-methoxycarbonylphenyl)carbamoylmethyl]thiazolidin-4-one produced in Example 113 as the starting compound, the above target compound was obtained.

NMR (DMSO-d$_6$) δ ppm: 1.94 (s, 3H), 1.95 (s, 3H), 2.95 (dd, 1H, Jgem=16.82 Hz, J=9.24 Hz), 3.28 (dd, 1H, J=3.63 Hz), 4.31 (dd, 1H), 7.11–8.57 (m, 3H, phenyl), 9.50 (brs, 1H).

EXAMPLE 115

Production of 5-[N-(4,5-dimethoxy-2-ethoxycarbonylphenyl)carbamoylmethyl]-2-isopropylidenehydrazonothiazolidin-4-one By following the similar procedure to Example 9 but substituting the ethyl 4-aminobenzoate with ethyl 2-amino-4,5-dimethoxybenzoate, the above target compound was obtained.

NMR (DMSO-d$_6$) δ ppm: 1.33 (t, 3H, J=6.93 Hz), 1.93 (s, 3H), 1.95 (s, 3H), 3.01 (dd, 1H, J=9.24 Hz, J=16.83 Hz), 3.20 (dd, 1H, J=3.96 Hz, J=16.83 Hz), 3.77 (s, 3H), 3.81 (s, 3H), 4.27–4.35 (m, 3H), 7.39 (s, 1H), 7.98 (s, 1H), 10.73 (s, 1H), 11.71 (brs, 1H).

EXAMPLE 116

Production of 5-[N-(2-carboxy-4,5-dimethoxyphenyl)carbamoylmethyl]-2-isopropylidenehydrazonothiazolidin-4-one By following the similar procedure to Example 14 but using 5-[N-(4,5-dimethoxy-2-ethoxycarbonylphenyl) carbamoylmethyl]-2-isopropylidenehydrazonothiazolidin-4-one produced in Example 115 as the starting compound, the above target compound was obtained.

NMR (DMSO-d$_6$) δ ppm: 1.94 (s, 3H), 1.95 (s, 3H), 3.02 (dd, 1H, J=8.91, 16.50 Hz), 3.19 (dd, 1H, J=3.96, 16.83 Hz), 3.76 (s, 3H), 3.81 (s, 3H), 4.33 (dd, 1H, J=3.63, 8.90 Hz), 7.44 (s, 1H), 8.18 (s, 1H), 11.54 (brs, 1H).

EXAMPLE 117

Production of 5-[N-(2-benzyloxycarbonyl-1(S)-methoxycarbonylethyl)-carbamoylmethyl]-2-isopropylidenehydrazonothiazolidin-4-one By following the similar procedure to Example 9 but substituting the ethyl 4-aminobenzoate with α-methyl, β-benzyl L-aspartate, the above target compound was obtained.

NMR (DMSO-d$_6$) δ ppm: 1.92 (s, 3H), 1.93 (s, 3H), 2.57–2.99 (m, 2H), 3.61 (s, 3H), 4.18–4.35 (m, 1H), 4.69 (dd, 1H, J=6.93 Hz, J=13.53 Hz), 5.11 (s, 2H), 7.36 (brs, 5H), 8.65 (dd, 1H, J=3.30 Hz, J=7.59 Hz), 11.67 (brs, 1H).

EXAMPLE 118

Production of 5-[N-(α-ethoxycarbonylbenzyl) carbamoylmethyl]-2-isopropylidenehydrazonothiazolidin-4-one By following the similar procedure to Example 9 but substituting the ethyl 4-aminobenzoate with DL-phenylglycine ethyl ester, the above target compound was obtained.

NMR (DMSO-d$_6$) δ ppm: 1.10–1.14 (m, 3H), 1.93 (s, 3H), 1.94 (s, 3H), 2.66–2.76 (m, 1H), 2.99–3.09 (m, 1H), 4.04–4.13 (m, 2H), 4.15–4.25 (m, 1H), 5.38 (t, 1H, J=5.27 Hz), 7.38 (s, 5H), 8.91 (t, 1H, J=6.27 Hz), 11.65 (brs, 1H).

EXAMPLE 119

Production of 5-[N-(α-carboxybenzyl) carbamoylmethyl]-2-isopropylidene-hydrazonothiazolidin-4-one By following the similar procedure to Example 14 but using 5-[N-(α-ethoxycarbonylbenzyl)carbamoylmethyl]-2-isopropylidenehydrazonothiazolidin-4-one produced in Example 118 as the starting compound, the above target compound was obtained.

NMR (DMSO-d$_6$) δ ppm: 1.93 (s, 3H), 1.94 (s, 3H), 2.69 (dd, 1H, J=10.23 Hz, J=16.50 Hz), 3.07 (dd, 1H, J=3.63 Hz, J=16.83 Hz), 4.22 (dd, 1H, J=3.63 Hz, J=10.22 Hz), 5.34 (d, 1H, J=7.59 Hz), 7.32–7.39 (m, 5H), 8.84 (d, 1H, J=7.26 Hz).

EXAMPLE 120

Production of 5-[N-(2-hydroxy-5-methoxycarbonylphenyl)carbamoylmethyl]-2-isopropylidenehydrazonothiazolidin-4-one By following the similar procedure to Example 9 but substituting the ethyl 4-aminobenzoate with methyl 3-amino-4-hydroxybenzoate, the above target compound was obtained.

NMR (DMSO-d$_6$) δ ppm: 1.94 (s, 3H), 1.95 (s, 3H), 2.97 (dd, 1H, Jgem=16.82 Hz, J=9.24 Hz), 3.28 (dd, 1H, J=3.96 Hz), 3.80 (s, 3H), 4.32 (dd, 1H), 6.94–8.54 (m, 3H, phenyl), 9.47 (brs, 1H), 10.83 (brs, 1H), 11.69 (brs, 1H).

EXAMPLE 121

Production of 5-[N-(5-carboxy-2-hydroxyphenyl) carbamoylmethyl]-2-isopropylidenehydrazonothiazolidin-4-one By following the similar procedure to Example 14 but using 5-[N-(2-hydroxy-5-methoxycarbonylphenyl) carbamoylmethyl]-2-isopropylidenehydrazonothiazolidin-4-one produced in Example 120 as the starting compound, the above target compound was obtained.

NMR (DMSO-d$_6$) δ ppm: 1.94 (s, 3H), 1.95 (s, 3H), 2.98 (dd, 1H, J=16.49 Hz, J=8.91 Hz), 3.27 (dd, 1H, J=16.49 Hz, J=3.96 Hz), 4.32 (dd, 1H, J=8.91 Hz, J=3.96 Hz), 6.99–8.74 (m, 3H), 9.48 (brs, 1H), 10.86 (brs, 1H), 11.52 (brs, 1H).

EXAMPLE 122

Production of 5-[N-(4-fluorophenyl) carbamoylmethyl]-2-isopropylidene-hydrazonothiazolidin-4-one By following the similar procedure to Example 9 but substituting the ethyl 4-aminobenzoate with 4-fluoroaniline, the above target compound was obtained.

NMR (DMSO-d$_6$) δ ppm: 1.94 (s, 3H), 1.95 (s, 3H), 2.85 (dd, 1H, Jgem=16.49 Hz, J=9.24 Hz), 3.14 (dd, J=3.96 Hz), 4.32 (dd, 1H), 7.11–7.60 (m, 4H, phenyl), 10.17 (brs, 1H), 11.69 (brs, 1H).

EXAMPLE 123

Production of 5-[N-(2-carboxy-4-methylphenyl)carbamoylmethyl]-2-isopropylidenehydrazonoimidazolidin-4-one By following the similar procedure to Example 9 but using 5-carboxymethyl-2-isopropylidenehydrazonoimidazolidin-4-one produced in Example 80 and methyl 2-amino-5-methylbenzoate as the starting compounds, 2-isopropylidenehydrazono-5-[N-(2-methoxycarbonyl-4-methylphenyl)carbamoylmethylimidazolidin-4-one was produced. This product was treated in the same manner as in Example 14 to give thereby the above target compound.

NMR (DMSO-d$_6$) δ ppm: 1.89 (s, 3H), 1.91 (s, 3H), 2.29 (s, 3H), 2.77–2.81 (m, 2H), 4.25 (t, 1H, J=5.61 Hz), 7.38 (dd, 1H, J=1.98 Hz, J=8.57 Hz), 7.78 (d, 1H, J=1.98 Hz), 8.31 (d, 1H, J=8.25 Hz), 11.13 (s, 1H).

EXAMPLE 124

Production of 5-[N-(4-hydroxy-2-methoxycarbonylphenyl)carbamoylmethyl]-2-isopropylidenehydrazonothiazolidin-4-one By following the similar procedure to Example 9 but substituting the ethyl 4-aminobenzoate with methyl 2-amino-5-hydroxybenzoate, the above target compound was obtained.

NMR (DMSO-d$_6$) δ ppm: 1.93 (s, 3H), 1.94 (s, 3H), 2.88 (dd, 1H, Jgem=16.50 Hz, J=9.24 Hz), 3.13 (dd, 1H, J=3.96 Hz), 3.81 (s, 3H), 4.28 (dd, 1H), 6.96–7.74 (m, 3H, phenyl), 9.69 (brs, 1H), 10.15 (brs, 1H), 11.68 (brs, 1H).

EXAMPLE 125

Production of 5-[N-(2-carboxy-4-hydroxyphenyl)carbamoylmethyl]-2-isopropylidenehydrazonothiazolidin-4-one By following the similar procedure to Example 14 but using 5-[N-(4-hydroxy-2-methoxycarbonylphenyl)carbamoylmethyl]-2-isopropylidenehydrazonothiazolidin-4-one produced in Example 124 as the starting compound, the above target compound was obtained.

NMR (DMSO-d$_6$) δ ppm: 1.94 (s, 6H), 2.93 (dd, 1H, Jgem=16.50 Hz, J=9.23 Hz), 3.14 (m, 1H), 4.29–4.31 (m, 1H), 6.97–8.09 (m, 3H, phenyl), 9.60 (brs, 1H), 10.67 (brs, 1H), 11.68 (brs, 1H).

EXAMPLE 126

Production of 5-[N-[4-[(6-acetoxy-2,5,7,8-tetramethylchroman-2-yl)methoxy]phenyl]carbamoylmethyl]-2-isopropylidenehydrazonothiazolidin-4-one By following the similar procedure to Example 9 but substituting the ethyl 4-aminobenzoate with 6-acetoxy-2-[(4-aminophenoxy)methyl]-2,5,7,8-tetramethylchromane produced in accordance with the procedure as disclosed in T. Yoshioka, T. Fujita, T. Kanai, Y. Aizawa, T. Kurumada, K. Hasegawa, H. Horikoshi, J. Med. Chem., 32, 421 (1989), the above target compound was obtained.

NMR (DMSO-d$_6$) δ ppm: 1.33 (s, 3H), 1.8–2.1 (m, 17H), 2.30 (s, 3H), 2.62 (t, 2H, J=6.60 Hz), 2.82 (dd, 1H, J=9.57 Hz, J=16.49 Hz), 3.12 (dd, 1H, J=3.96 Hz, J=16.49 Hz), 3.97 (q, 2H), 4.31 (dd, 1H, J=3.96 Hz, J=9.57 Hz), 6.92 (d, 2H, J=8.90 Hz), 7.45 (d, 2H, J=9.24 Hz), 9.97 (s, 1H), 11.69 (brs, 1H).

EXAMPLE 127

Production of 5-[N-[4-[(6-hydroxy-2,5,7,8-tetramethylchroman-2-yl)methoxy]phenyl]carbamoylmethyl]-2-isopropylidenehydrazonothiazolidin-4-one 0.6 g of 5-[N-[4-[(6-acetoxy-2,5,7,8-tetramethylchroman-2-yl)methoxy]phenyl]carbamoylmethyl]-2-isopropylidenehydrazonothiazolidin-4-one produced in Example 126 was dissolved in 10 ml of methanol. After adding a 1N aqueous solution of sodium hydroxide, the mixture was stirred at room temperature for 2 hours. Then the reaction mixture was extracted with a mixture of ethyl acetate with 0.1N hydrochloric acid. The organic layer was collected, washed with a saturated aqueous solution of sodium chloride and dried over anhydrous sodium sulfate. After distilling off the solvent under reduced pressure, 0.49 g of the above target compound was obtained as a pale yellow amorphous powder.

NMR (DMSO-d$_6$) δ ppm: 1.29 (s, 3H), 1.8–2.1 (m, 17H), 2.56 (t, 2H), 2.82 (dd, 1H, J=9.57 Hz, J=16.49 Hz), 3.12 (dd, 1H, J=3.63 Hz, J=16.49 Hz), 3.92 (q, 2H), 4.31 (dd, 1H, J=3.63 Hz, J=9.57 Hz), 6.91 (d, 2H, J=9.24 Hz), 7.45 (d, 2H, J=8.91 Hz), 9.96 (s, 1H), 11.70 (brs, 1H).

EXAMPLE 128

Production of 2-isopropylidenehydrazono-5-[N-[3-(trifluoromethyl)phenyl]carbamoylmethyl]thiazolidin-4-one By following the similar procedure to Example 9 but substituting the ethyl 4-aminobenzoate with 3-(trifluoromethyl)aniline, the above target compound was obtained.

NMR (DMSO-d$_6$) δ ppm: 1.94, 1.95 (s, s, 6H), 2.92 (dd, 1H, J=9.23, 16.83 Hz), 3.18 (dd, 1H, J=3.96, 16.83 Hz), 4.34 (dd, 1H, J=3.96, 9.23 Hz), 7.41 (d, 1H, J=7.59 Hz), 7.56 (t, 1H, J=7.92 Hz), 7.72 (d, 1H, J=8.25 Hz), 8.07 (s, 1H), 10.47 (s, 1H), 11.72 (brs, 1H).

EXAMPLE 129

Production of 2-isopropylidenehydrazono-5-[N-(4-methoxy-2-methylphenyl)carbamoylmethyl]thiazolidin-4-one By following the similar procedure to Example 9 but substituting the ethyl 4-aminobenzoate with 4-methoxy-2-methylaniline, the above target compound was obtained.

NMR (DMSO-d$_6$) δ ppm: 1.94 (s, 6H), 2.15 (s, 3H), 2.81 (dd, 1H, Jgem=16.16 Hz, J=9.57 Hz), 3.15 (dd, 1H, J=3.96 Hz), 3.72 (s, 3H), 4.30 (dd, 1H), 6.70–7.20 (m, 3H, phenyl), 9.38 (brs, 1H), 11.68 (brs, 1H).

EXAMPLE 130

Production of 5-[N-(4-fluoro-2-methoxycarbonylphenyl)carbamoylmethyl]-2-isopropylidenehydrazonothiazolidin-4-one By following the similar procedure to Example 9 but substituting the ethyl 4-aminobenzoate with methyl 2-amino-5-fluorobenzoate, the above target compound was obtained.

NMR (DMSO-$d_6$) δ ppm: 1.93 (s, 3H), 1.94 (s, 3H), 2.95 (dd, 1H, Jgem=16.50 Hz, J=9.24 Hz), 3.18 (dd, 1H, J=3.96 Hz), 3.84 (s, 3H), 4.31 (dd, 1H), 7.45–7.98 (m, 3H, phenyl), 10.39 (brs, 1H), 11.70 (brs, 1H).

EXAMPLE 131

Production of 5-[N-(2-carboxy-4-fluorophenyl) carbamoylmethyl]-2-isopropylidenehydrazonothiazolidin-4-one By following the similar procedure to Example 14 but using 5-[N-(4-fluoro-2-methoxycarbonylphenyl)-carbamoyl-methyl]-2-isopropylidenehydrazonothiazolidin-4-one produced in Example 130 as the starting compound, the above target compound was obtained.

NMR (DMSO-$d_6$) δ ppm: 1.94 (s, 3H), 1.95 (s, 3H), 3.01 (dd, 1H, Jgem=16.83 Hz, J=8.90 Hz), 3.20 (dd, 1H, J=3.96 Hz), 4.32 (dd, 1H), 7.44–8.34 (m, 3H, phenyl), 10.91 (brs, 1H), 11.60 (brs, 1H).

EXAMPLE 132

Production of 5-[N-(3-fluoro-2-methoxycarbonylphenyl)carbamoylmethyl]-2-isopropylidenehydrazonothiazolidin-4-one By following the similar procedure to Example 9 but substituting the ethyl 4-aminobenzoate with methyl 2-amino-6-fluorobenzoate, the above target compound was obtained.

NMR (DMSO-$d_6$) δ ppm: 1.94 (s, 3H), 1.95 (s, 3H), 2.86 (dd, 1H, Jgem=16.82 Hz, J=9.24 Hz), 3.14 (dd, 1H, J=3.63 Hz), 3.79 (s, 3H), 4.28 (dd, 1H), 7.08–7.57 (m, 3H, phenyl), 10.21 (brs, 1H), 11.68 (brs, 1H).

EXAMPLE 133

Production of 5-[N-(2-carboxy-3-fluorophenyl) carbamoylmethyl]-2-isopropylidenehydrazonothiazolidin-4-one By following the similar procedure to Example 14 but using 5-[N-(3-fluoro-2-methoxycarbonylphenyl) carbamoylmethyl]-2-isopropylidenehydrazonothiazolidin-4-one produced in Example 132 as the starting compound, the above target compound was obtained.

NMR (DMSO-$d_6$) δ ppm: 1.94 (2s, 6H), 2.88 (dd, 1H, Jgem=16.50 Hz, J=9.57 Hz), 3.17 (dd, 1H, J=3.63 Hz), 4.29 (dd, 1H), 7.04–7.59 (m, 3H, phenyl), 10.26 (brs, 1H), 11.75 (brs, 1H).

EXAMPLE 134

Production of 2-isopropylidenehydrazono-5-[N-(2-methoxycarbonyl-5-methyl-phenyl) carbamoylmethyl]thiazolidin-4-one By following the similar procedure to Example 9 but substituting the ethyl 4-aminobenzoate with methyl 2-amino-4-methylbenzoate, the above target compound was obtained.

NMR (DMSO-$d_6$) δ ppm: 1.93 (s, 3H), 1.95 (s, 3H), 2.35 (s, 3H), 3.01 (dd, 1H, Jgem=16.50 Hz, J=8.91 Hz), 3.20 (dd, 1H, J=3.96 Hz), 3.84 (s, 3H), 4.31 (dd, 1H), 7.02–8.04 (m, 3H, phenyl).

EXAMPLE 135

Production of 5-[N-(2-carboxy-5-methylphenyl) carbamoylmethyl]-2-isopropylidenehydrazonothiazolidin-4-one By following the similar procedure to Example 14 but using 5-[N-(2-methoxycarbonyl-5-methylphenyl) carbamoylmethyl]thiazolidin-4-one produced in Example 134 as the starting compound, the above target compound was obtained.

NMR (DMSO-$d_6$) δ ppm: 1.94 (s, 3H), 1.95 (s, 3H), 2.35 (s, 3H), 3.05 (dd, Jgem=16.50 Hz, J=8.58 Hz), 3.20 (m, 1H), 4.32 (dd, 1H, J=3.96 Hz), 6.97–8.28 (m, 3H, phenyl), 11.18 (brs, 1H), 11.73 (brs, 1H), 13.42 (brs, 1H).

EXAMPLE 136

Production of 2-isopropylidenehydrazono-5-[N-(3-methoxycarbonyl-5-(trifluoromethyl)phenyl] carbamoylmethyl]thiazolidin-4-one By following the similar procedure to Example 9 but substituting the ethyl 4-aminobenzoate with methyl 3-amino-5-(trifluoromethyl)benzoate, the above target compound was obtained.

NMR (DMSO-$d_6$) δ ppm: 1.94 (s, 3H), 1.95 (s, 3H), 2.96 (dd, 1H, Jgem=16.82 Hz, J=8.91 Hz), 3.19 (dd, 1H, J=3.96 Hz), 3.91 (s, 3H), 4.35 (dd, 1H), 7.87 (brs, 1H), 8.26 (brs, 1H), 8.42 (brs, 1H), 10.71 (brs, 1H), 11.72 (brs, 1H).

EXAMPLE 137

Production of 5-[N-[3-carboxy-5-(trifluoromethyl) phenyl]carbamoylmethyl]-2-isopropylidenehydrazonothiazolidin-4-one By following the similar procedure to Example 14 but using 2-isopropylidenehydrazono-5-[N-[3-methoxy-carbonyl-5-(trifluoromethyl)phenyl]carbamoylmethyl] thiazolidin-4-one produced in Example 136 as the starting compound, the above target compound was obtained.

NMR (DMSO-$d_6$) δ ppm: 1.94 (s, 3H), 1.95 (s, 3H), 2.96 (dd, 1H, Jgem=16.49 Hz, J=8.91 Hz), 3.20 (dd, 1H, J=3.96 Hz), 4.35 (dd, 1H), 7.85 (brs, 1H), 8.26 (brs, 1H), 8.37 (brs, 1H), 10.68 (brs, 1H), 11.76 (brs, 1H).

EXAMPLE 138

Production of 2-isopropylidenehydrazono-5-[N-[4-(trifluoromethyl)phenyl]carbamoylmethyl] thiazolidin-4-one By following the similar procedure to Example 9 but substituting the ethyl 4-aminobenzoate with 4-(trifluoromethyl)aniline, the above target compound was obtained.

NMR (DMSO-$d_6$) δ ppm: 1.93 (s, 3H), 1.95 (s, 3H), 2.93 (dd, 1H, Jgem=16.50 Hz, J=9.24 Hz), 3.20 (dd, 1H, J=3.96 Hz), 4.35 (dd, 1H), 7.66–7.79 (m, 4H, phenyl), 10.49 (brs, 1H), 11.71 (brs, 1H).

EXAMPLE 139

Production of 2-isopropylidenehydrazono-5-[N-(4-methoxy-2-methoxycarbonyl-phenyl) carbamoylmethyl]thiazolidin-4-one By following the similar procedure to Example 9 but substituting the ethyl 4-aminobenzoate with methyl 2-amino-5-methoxybenzoate, the above target compound was obtained.

NMR (DMSO-$d_6$) δ ppm: 1.93 (s, 3H), 1.94 (s, 3H), 2.91 (dd, 1H, Jgem=16.50 Hz, J=9.24 Hz), 3.16 (dd, 1H, J=16.50 Hz, J=3.63 Hz), 3.78 (s, 3H), 3.83 (s, 3H), 4.30 (dd, 1H, J=9.24 Hz, J=3.63 Hz), 7.17–7.84 (m, 3H, phenyl), 10.24 (brs, 1H), 11.70 (brs, 1H).

EXAMPLE 140

Production of 5-[N-(2-carboxy-4-methoxyphenyl)carbamoylmethyl]-2-isopropylidenehydrazonothiazolidin-4-one By following the similar procedure to Example 14 but using 2-isopropylidenehydrazono-5-[N-(4-methoxy-2-carbonylphenyl)carbamoylmethyl]thiazolidin-4-one produced in Example 139 as the starting compound, the above target compound was obtained.

NMR (DMSO-$d_6$) δ ppm: 1.93 (s, 3H), 1.94 (s, 3H), 2.96 (dd, 1H, J=16.50 Hz, J=9.24 Hz), 3.17 (dd, 1H, J=16.50 Hz, J=3.63 Hz), 3.77 (s, 3H), 4.31 (dd, 1H, J=9.24 Hz, J=3.63 Hz), 7.17–8.21 (m, 3H, phenyl), 10.76 (brs, 1H), 11.72 (brs, 1H), 13.60 (brs, 1H).

PHARMACOLOGICAL TEST

The effects of the compounds of the present invention represented by the general formula (1) for inhibiting Maillard reaction were proved by the following screening system.

Lysozyme and fructose were dissolved in a buffer solution of 0.2M sodium phosphate (pH 7.4) to respectively give concentrations of 10 mg/ml and 100 mM. After incubating at 37° C. for 3 days, a definite amount of the mixture was taken out and electrophoresed with the use of SDS-PAGE. After the completion of the electrophoresis, the gel was stained with 0.2% Coomassie Brilliant Blue R-250 and the amount of the dimer thus formed was determined.

Each of the test compounds was added before the initiation of the incubation and the effect of suppressing the formation of the dimer was examined at various concentrations, whereby the $IC_{50}$ value was obtained. As a positive control, aminoguanidine, which is a known glycation inhibitor, was employed and the inhibition ratio of the test compound to aminoguanidine ($IC_{50}$ of aminoguanidine/ $IC_{50}$ of test compound) was calculated.

The test compounds are as follows.

1. 5-(4-Benzyloxybenzyl)-2-isopropylidenehydrazonoimidazolidin-4-one
2. 2-Isopropylidenehydrazono-5-methylimidazolidin-4-one
3. 5-Benzyl-2-isopropylidenehydrazonoimidazolidin-4-one
4. 5-(4-Hydroxybenzyl)-2-isopropylidenehydrazonoimidazolidin-4-one
5. 5-[4-(2,6-Dichlorobenzyloxy)benzyl]-2-isopropylidenehydrazonoimidazolidin-4-one
6. 5-[4-(4-Chlorobenzyloxy)benzyl]-2-isopropylidenehydrazonoimidazolidin-4-one
7. 5-(4-Hydroxyphenyl)-2-isopropylidenehydrazonoimidazolidin-4-one
8. 5-(4-Hydroxybenzyl)-2-isopropylidenehydrazono-3-(4-methoxybenzyl)imidazolidin-4-one
9. 3-Benzyl-5-(4-hydroxybenzyl)-2-isopropylidenehydrazonoimidazolidin-4-one
10. 2-Isopropylidenehydrazono-5-(4-phenylthiobenzyl)imidazolidin-4-one
11. 2-Isopropylidenehydrazono-5-(4-methylthiobenzyl)thiazolidin-4-one
12. 5-(4-Benzyloxybenzyl)-2-isopropylidenehydrazonothiazolidin-4-one
13. 5-Carboxymethyl-2-isopropylidenehydrazonothiazolidin-4-one
14. 2-Isopropylidenehydrazono-5-(N-propylcarbamoylmethyl)thiazolidin-4-one
15. 5-[N-(4-ethoxycarbonylphenyl)carbamoylmethyl]-2-isopropylidenehydrazonothiazolidin-4-one
16. 5-[N-(4-carboxyphenyl)carbamoylmethyl]-2-isopropylidenehydrazonothiazolidin-4-one
17. 2-Isopropylidenehydrazono-5-[N-(2-oxo-1,2,3,4-tetrahydro-quinolin-3-yl)carbamoylmethyl]thiazolidin-4-one
18. 5-(N-cyclohexylcarbamoylmethyl)-2-isopropylidenehydrazonothiazolidin-4-one
19. 5-(N-ethoxycarbonylmethylcarbamoylmethyl)-2-isopropylidenehydrazonothiazolidin-4-one
20. 5-Carboxymethyl-3-ethoxycarbonylmethyl-2-isopropylidenehydrazonothiazolidin-4-one
21. 2-Isopropylidenehydrazono-3-phenylthiazolidin-4-one
22. 2-Isopropylidenehydrazino-4-phenylthiazole
23. 2-Isopropylidenehydrazino-4-methylthiazole
24. 4-(4-Chlorophenyl)-2-isopropylidenehydrazinothiazole
25. 2-isopropylidenehydrazino-4-(4-phenylthiophenyl)thiazole
26. 4-(3,4-Dihydroxyphenyl)-2-isopropylidenehydrazinothiazole
27. 4-[4-(4-Chlorobenzyloxy)phenyl]-2-isopropylidenehydrazinothiazole
28. 2-isopropylidenehydrazino-4,5,6,7-tetrahydrobenzothiazole
29. 9-Benzyloxymethyl-1,4,5,7-tetraazabicyclo[4.3.0]nonan-5-ene-3,8-dione
30. 5-(N-Benzylcarbamoylmethyl)-2-isopropylidenehydrazonothiazolidin-4-one
31. 5-(N-isopropylcarbamoylmethyl)-2-isopropylidenehydrazonothiazolidin-4-one
32. 2-isopropylidenehydrazono-5-(N-phenylcarbamoylmethyl)thiazolidin-4-one
33. 2-Isopropylidenehydrazono-5-(4-nitrobenzyl)imidazolidin-4-one
34. 5-[4-(4-Chlorophenylthio)benzyl]-2-isopropylidenehydrazonothiazolidine-4-one
35. 5-[4-(Cyclohexylmethyloxy)benzyl]-2-isopropylidenehydrazonoimidazolidin-4-one
36. 2-Isopropylidenehydrazono-5-[4-(2-thienylmethoxy)benzyl]imidazolidin-4-one
37. 5-(4-Benzylbenzyl)-2-isopropylidenehydrazonoimidazolidin-4-one
38. 2-Isopropylidenehydrazono-5-[4-(2-phenylethoxy)benzyl]imidazolidin-4-one
39. 5-[4-(4-Chlorobenzoylamino)benzyl]-2-isopropylidenehydrazonoimidazolidin-4-one
40. 5-(3-Indolylmethyl)-2-isopropylidenehydrazonoimidazolidin-4-one
41. 5-(5-Hydroxy-3-indolylmethyl)-2-isopropylidenehydrazonoimidazolidin-4-one
42. 5-(3,4-Dihydroxybenzyl)-2-isopropylidenehydrazonoimidazolidin-4-one
43. 2-Isopropylidenehydrazono-5-methoxycarbonylmethylimidazolidin-4-one
44. 5-Benzyloxycarbonylmethyl-2-isopropylidenehydrazonoimidazolidin-4-one
45. 5-Carboxymethyl-2-isopropylidenehydrazonoimidazolidin-4-one
46. 2-Isopropylidenehydrazono-5-(N-phenylcarbamoylmethyl)imidazolidin-4-one
47. 5-(N-carboxymethylcarbamoylmethyl)-2-isopropylidenehydrazonothiazolidin-4-one
48. 2-Isopropylidenehydrazono-5-[4-(3-pyridylmethoxy)benzyl]thiazolidin-4-one
49. 5-[N-(3,4-difluorophenyl)carbamoylmethyl]-2-isopropylidenehydrazonothiazolidin-4-one
50. 5-[N-(4-benzyloxyphenyl)carbamoylmethyl]-2-isopropylidenehydrazonothiazolidin-4-one 51. 5-[N-(4-chlorophenyl)carbamoylmethyl]-2-isopropylidenehydrazonothiazolidin-4-one
52. 2-Isopropylidenehydrazono-5-[N-(4-methoxyphenyl)carbamoylmethyl]thiazolidin-4-one
53. 2-Isopropylidenehydrazono-5-[N-(4-methylphenyl)carbamoylmethyl]thiazolidin-4-one
54. 5-[N-(2-carboxy-4-methylphenyl)carbamoylmethyl]-2-isopropylidenehydrazonothiazolidin-4-one
55. 2-Isopropylidenehydrazono-5-[N-(4-methylthiophenyl)carbamoylmethyl]thiazolidin-4-one
56. 5-[N-(4-bromophenyl)carbamoylmethyl]-2-isopropylidenehydrazonothiazolidin-4-one
57. 2-Isopropylidenehydrazono-5-[N-(3,4,5-trichlorophenyl)carbamoylmethyl]thiazolidin-4-one
58. 2-Isopropylidenehydrazono-5-[N-(3,4-methylenedioxyphenyl)carbamoylmethyl]thiazolidin-4-one
59. 2-Isopropylidenehydrazono-5-[N-(1-naphthyl)carbamoylmethyl]thiazolidin-4-one
60. 5-[N-(3,5-dichlorophenyl)carbamoylmethyl]-2-isopropylidenehydrazonothiazolidin-4-one
61. 3-Ethoxycarbonylmethyl-5-(N-phenylcarbamoylmethyl)-2-isopropylidenehydrazonothiazolin-4-one
62. 5-(4-Benzyloxycarbonylaminobutyl)-2-isopropylidenehydrazonoimidazolidin-4-one
63. 2-Isopropylidenehydrazono-5-(4-methoxycarbonylaminobutyl)imidazolidin-4-one
64. 5-(N-cyclopropylcarbamoylmethyl)-2-isopropylidenehydrazonoimidazolidin-4-one
65. 2-Isopropylidenehydrazono-5-(N-methyl-N-phenylcarbamoylmethyl)thiazolidin-4-one
66. 2-Isopropylidenehydrazono-5-[N-(3-pyridylmethyl)carbamoylmethyl]thiazolidin-4-one
67. 2-Isopropylidenehydrazono-5-(2-methylpropyl)imidazolidin-4-one
68. 2-Isopropylidenehydrazono-5-[N-(3-imidazol-1-yl)propylcarbamoylmethyl]thiazolidin-4-one
69. 2-Isopropylidenehydrazono-5-(N-morpholinocarbamoylmethyl)thiazolidin-4-one
70. 2-isopropylidenehydrazono-5-[N-(2-thienylmethyl)carbamoylmethyl]thiazolidin-4-one
71. 2-Isopropylidenehydrazono-5-[N-(4-morpholinophenyl)carbamoylmethyl]thiazolidin-4-one
72. 2-Isopropylidenehydrazono-5-[N-(1-phenylethyl)carbamoylmethyl]thiazolidin-4-one
73. 2-Isopropylidenehydrazono-5-[N-(1-phenylethyl)carbamoylmethyl]imidazolidin-4-one
74. 5-(4-Benzyloxybenzyl)-2-hydrazonoimidazolidin-4-one hydrochloride
75. 5-(4-Benzyloxybenzyl)-2-(4-bromobenzenesulfonohydrazono)imidazolidin-4-one
76. 2-(4-Acetoamidobenzenesulfonohydrazono)-5-(4-benzyloxybenzyl)imidazolidin-4-one
77. 2-Cyclopentylidenehydrazono-5-(4-benzyloxybenzyl)imidazolidin-4-one
78. 5-(4-Imidazolylmethyl)-2-isopropylidenehydrazonoimidazolidin-4-one
79. 5-isopropyl-2-isopropylidenehydrazonoimidazolidin-4-one
80. 2-Isopropylidenehydrazono-5-[2-(N-phenylcarbamoyl)ethyl]imidazolidin-4-one
81. 2-Hydrazono-5-(N-phenylcarbamoylmethyl)thiazolidin-4-one
82. 2-Dicyclopropylmethylenehydrazono-5-(N-phenylcarbamoylmethyl)thiazolidin-4-one
83. 2-Cyclohexylmethylenehydrazono-5-(N-phenylcarbamoylmethyl)thiazolidin-4-one
84. 2-Isopropylidenehydrazono-5-[N-(2-methyl-5-methoxycarbonylphenyl)carbamoylmethyl]thiazolidin-4-one
85. 2-Isopropylidenehydrazono-5-[N-(2-methoxycarbonyl-4-methylphenyl)carbamoylmethyl]thiazolidin-4-one
86. 2-isopropylidenehydrazino-4-trifluoromethylthiazole
87. 4-Ethoxycarbonylmethyl-2-isopropylidenehydrazinothiazole
88. 4-Carboxymethyl-2-isopropylidenehydrazinothiazole
89. 2-Isopropylidenehydrazino-4-(3-pyridyl)thiazole
90. 5-[N-(3,4-dimethoxyphenyl)carbamoylmethyl]-2-isopropylidenehydrazonothiazolidin-4-one
91. 5-[N-(5-carboxy-2-methylphenyl)carbamoylmethyl]-2-isopropylidenehydrazonothiazolidin-4-one
92. 5-[N-(2-carboxyphenyl)carbamoylmethyl]-2-isopropylidenehydrazonothiazolidin-4-one
93. 2-Isopropylidenehydrazono-5-[N-(2-methoxycarbonylphenyl)carbamoylmethyl]thiazolidin-4-one
94. 4-[N-(3,4-dimethoxyphenyl)carbamoylmethyl]-2-isopropylidenehydrazinothiazole
95. 2-Isopropylidenehydrazino-4-(2-thiazolyl)thiazole
96. 2-Isopropylidenehydrazono-5-[N-(2-methoxycarbonyl-4-methylphenyl)carbamoylmethyl]imidazolidin-4-one
97. 5-[N-(1-ethoxycarbonyl-3-methylbutyl)carbamoylmethyl]-2-isopropylidenehydrazonothiazolidin-4-one
98. 4-(4-Carboxyphenyl)-2-isopropylidenehydrazinothiazole
99. 2-Isopropylidenehydrazino-4-(3-thienyl)thiazole
100. 5-{N-[1-ethoxycarbonyl-2-(4-benzyloxyphenyl)ethyl]-carbamoylmethyl}-2-isopropylidenehydrazonothiazolidin-4-one
101. 5-{N-[1-carboxy-2-(4-benzyloxyphenyl)ethyl]carbamoylmethyl}-2-isopropylidenehydrazonothiazolidin-4-one
102. 2-Isopropylidenehydrazono-5-{N-[1-methoxycarbonyl-2-(3-indolyl)ethyl]carbamoylmethyl}thiazolidin-4-one
103. 5-[N-(1-carboxy-3-methylbutyl)carbamoylmethyl]-2-isopropylidenehydrazonothiazolidin-4-one
104. 5-{N-[1-carboxy-2-(3-indolyl)ethyl]carbamoylmethyl}-2-isopropylidenehydrazonothiazolidin-4-one
105. 5-[N-(3-ethoxycarbonylphenyl)carbamoylmethyl]-2-isopropylidenehydrazonothiazolidin-4-one
106. 5-[N-(3-carboxyphenyl)carbamoylmethyl]-2-isopropylidenehydrazonothiazolidin-4-one
107. 2-Isopropylidenehydrazono-5-[N-(2-methoxycarbonylmethylphenyl)carbamoylmethyl]thiazolidin-4-one
108. 5-[N-(2-carboxymethylphenyl)carbamoylmethyl]-2-isopropylidenehydrazonothiazolidin-4-one
109. 2-Isopropylidenehydrazono-5(R)-(N-phenylcarbamoylmethyl)thiazolidin-4-one
110. 2-Isopropylidenehydrazono-5(S)-(N-phenylcarbamoylmethyl)thiazolidin-4-one
111. 5-[N-(2-carboxy-4-chlorophenyl)carbamoylmethyl]-2-isopropylidenehydrazonothiazolidin-4-one
112. 5-[N-(2,6-dimethylphenyl)carbamoylmethyl]-2-isopropylidenehydrazonothiazolidin-4-one
113. 5-[N-(5-carboxy-2-methoxyphenyl)carbamoylmethyl]-2-isopropylidenehydrazonothiazolidin-4-one
114. 5-[N-(2-carboxy-4,5-dimethoxyphenyl)carbamoylmethyl]-2-isopropylidenehydrazonothiazolidin-4-one
115. 2-Isopropylidenehydrazono-5-[N-[3-(trifluoromethyl)phenyl]carbamoylmethyl]thiazolidin-4-one 116. 2-Isopropylidenehydrazono-5-[N-(4-methoxy-2-methylphenyl)carbamoylmethyl]thiazolidin-4-one
117. 5-[N-(2-carboxy-4-fluorophenyl)carbamoylmethyl]-2-isopropylidenehydrazonothiazolidin-4-one
118. 5-[N-(3-fluoro-2-methoxycarbonylphenyl)carbamoylmethyl]-2-isopropylidenehydrazonothiazolidin-4-one
119. 5-[N-(2-carboxy-3-fluorophenyl)carbamoylmethyl]-2-isopropylidenehydrazonothiazolidin-4-one
120. 5-[N-(2-carboxy-5-methylphenyl)carbamoylmethyl]-2-isopropylidenehydrazonothiazolidin-4-one The results are given in Table 1 below.

TABLE 1

| Test compound | $IC_{50}$ of aminoguanidine/$IC_{50}$ of test compound |
| --- | --- |
| 1 | 3.6 |
| 2 | 2.8 |
| 3 | 1.6 |
| 4 | 4.8 |
| 5 | 8.0 |
| 6 | 8.3 |
| 7 | 1.1 |
| 8 | 1.8 |
| 9 | 1.3 |
| 10 | 5.4 |
| 11 | 1.2 |
| 12 | 1.1 |
| 13 | 2.5 |
| 14 | 3.1 |
| 15 | 1.2 |
| 16 | 1.9 |
| 17 | 3.5 |
| 18 | 1.5 |
| 19 | 4.8 |
| 20 | 3.0 |
| 21 | 0.8 |
| 22 | 3.1 |
| 23 | 3.0 |
| 24 | 2.8 |
| 25 | 11.4 |
| 26 | 4.4 |
| 27 | 1.8 |
| 28 | 4.4 |
| 29 | 0.6 |
| 30 | 3.5 |
| 31 | 25 |
| 32 | 55 |
| 33 | 2.4 |
| 34 | 0.6 |
| 35 | 0.8 |
| 36 | 3.5 |
| 37 | 1.7 |
| 38 | 4.2 |
| 39 | 1.7 |
| 40 | 2.6 |
| 41 | 4.5 |
| 42 | 78.9 |
| 43 | 5.4 |
| 44 | 5.2 |
| 45 | 4.8 |
| 46 | 5.7 |
| 47 | 0.3 |
| 48 | 11.0 |
| 49 | 7.4 |
| 50 | 0.3 |
| 51 | 5.3 |
| 52 | 10.2 |
| 53 | 0.8 |
| 54 | 9.2 |
| 55 | 0.8 |
| 56 | 1.2 |
| 57 | 1.3 |
| 58 | 1.8 |
| 5 | 0.6 |
| 60 | 1.1 |
| 61 | 0.91 |
| 62 | 57 |
| 63 | 53 |
| 64 | 4.5 |
| 65 | 6.8 |
| 66 | 4.6 |
| 67 | 2.6 |
| 68 | 3.5 |
| 69 | 50 |
| 70 | 36 |
| 71 | 5.8 |
| 72 | 7.0 |
| 73 | 1.3 |
| 74 | 0.6 |
| 75 | 1.5 |
| 76 | 1.4 |
| 77 | 2.2 |
| 78 | 4.0 |
| 79 | 1.5 |
| 80 | 3.1 |
| 81 | 0.8 |
| 82 | 2.3 |
| 83 | 1.8 |
| 84 | 7.9 |
| 85 | 0.25 |
| 86 | 3.4 |
| 87 | 3.3 |
| 88 | 0.94 |
| 89 | 1.6 |
| 90 | 42 |
| 91 | 37 |
| 92 | 20 |
| 93 | 26 |
| 93 | 33.7 |
| 95 | 3.9 |
| 96 | 2.3 |
| 97 | 4.2 |
| 98 | 1.1 |
| 99 | 1.5 |
| 100 | 4.3 |
| 101 | 1.7 |
| 102 | 1.7 |
| 103 | 1.0 |
| 104 | 0.7 |
| 105 | 3.2 |
| 106 | 2.8 |
| 107 | 3.1 |
| 108 | 4.5 |
| 109 | 5.8 |
| 110 | 5.6 |
| 111 | 8.8 |
| 112 | 6.4 |
| 113 | 8.5 |
| 114 | 5.4 |
| 115 | 12.0 |
| 116 | 7.3 |
| 117 | 7.0 |
| 118 | 6.1 |
| 119 | 10.5 |
| 120 | 5.3 |

PREPARATION EXAMPLE 1

The following ingredients were mixed and tabletted in a conventional manner to thereby give 100 tablets each containing 50 mg of the active ingredient:

| | |
| --- | --- |
| 5-(4-benxyloxybenxyl)-2-isopropylidene-hydrazonoimidazolidin-4-one | 5 g |
| Sodium lauryl sulfate | 0.2 g |
| Magnesium stearate | 0.2 g |
| Crystalline cellulose | 4.6 g. |

PREPARATION EXAMPLE 2

| | |
|---|---|
| 5-[4-(4-Chlorobenzyloxy)benzyl]-2-isopropylidenehydrazonoimidazolidin-4-one | 5 g |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride were dissolved in about a half amount of the distilled water at 80° C. under stirring. The solution thus obtained was cooled to 40° C. Then the active compound of the present invention, polyethylene glycol and polyoxyethylene sorbitan monooleate were successively added to the solution and dissolved therein. Next, the distilled water for injection was added to the obtained solution so as to adjust to the final volume. After sterilizing by filtering through a suitable filter paper, an injection was obtained.

We claim:

1. A compound represented by the general formula:

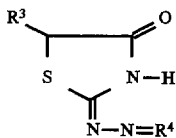

wherein $R^4$ is a lower alkylidene group, a lower alkylidene group having 1 or 2 lower cycloalkyl groups, a lower cycloalkylidene group, a diphenyl-lower alkylidene group or a phenyl-lower alkylidene group; and $R^3$ is —Z—CO—$R^a$, wherein Z is a lower alkylene group and $R^a$ is —Tyr($OR^{a1}$)—$OR^{b1}$, —Leu—$OR^{b2}$, —Trp—$OR^{b3}$, —Asp($OR^{a2}$)—$OR^{b4}$, —Ph—Gly—$OR^{b5}$ or —N($R^6$)—$R^7$, wherein $R^{a1}$ and $R^{a2}$ each is a hydrogen atom or a benzyl group;

$R^{b1}$, $R^{b2}$, $R^{b3}$, $R^{b4}$ and $R^{b5}$ each is a hydrogen atom or a lower alkyl group;

$R^6$ is a lower alkyl group, a carboxy-lower alkyl group, a lower alkoxycarbonyl-lower alkyl group, a phenyl-lower alkyl group, a lower cycloalkyl group, a phenyl group which may have 1 to 3 substituents, a naphthyl group, a 3,4-dihydroxycarbostyryl group, a morpholino group or a 5-membered or 6-membered unsaturated heterocyclic-lower alkyl group having 1 or 2 hetero atoms;

wherein said substituent of said phenyl group is a halogen atom, a hydroxyl group, a nitro group, a lower alkyl group, a lower alkoxy group, a lower alkylthio group, a carboxyl group, a lower alkoxycarbonyl group, a phenyl-lower alkoxy group, a lower alkylendioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group or a 6-lower alkanoyloxy-2,5,7,8-tetramethyl-2-chromanylmethyloxy group; and said hetero atom is a nitrogen atom, an oxygen atom or a sulfur atom; and $R^7$ is a hydrogen atom or a lower alkyl group;

or a pharmaceutically acceptable salt thereof.

2. The compound or the pharmaceutically acceptable salt thereof of claim 1, wherein $R^a$ is —Tyr($OR^{a1}$)—$OR^{b1}$, —Leu—$OR^{b2}$, —Trp—$OR^{b3}$, —Asp($OR^{a2}$)—$OR^{b4}$ or —Ph—Gly—$OR^{b5}$, wherein $R^{a1}$ and $R^{a2}$ each is a hydrogen atom or a benzyl group, and $R^{b1}$, $R^{b2}$, $R^{b3}$, $R^{b4}$ and $R^{b5}$ each is a hydrogen atom or a lower alkyl group; and $R^4$ is a lower alkylidene group.

3. The compound or the pharmaceutically acceptable salt thereof of claim 1, wherein $R^a$ is —N($R^6$)—$R^7$, wherein $R^6$ is a lower alkyl group, a carboxy-lower alkyl group, a lower alkoxycarbonyl-lower alkyl group, a phenyl-lower alkyl group, a lower cycloalkyl group, a phenyl group which may have 1 to 3 substituents, a naphthyl group, a 3,4-dihydroxycarbostyryl group, a morpholino group or a 5-membered or 6-membered unsaturated heterocyclic-lower alkyl group having 1 or 2 hetero atoms;

wherein said substituent of a phenyl group is a halogen atom, a hydroxyl group, a nitro group, a lower alkyl group, a lower alkoxy group, a lower alkylthio group, a carboxyl group, a lower alkoxycarbonyl group, a phenyl-lower alkoxy group, a lower alkylenedioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group or a 6-lower alkanoyloxy-2,5,7,8-tetramethyl-2-chromanylmethyloxy group; and said hetero atom is a nitrogen atom, an oxygen atom or a sulfur atom, and $R^7$ is a hydrogen atom or a lower alkyl group; and $R^4$ is a lower alkylidene group.

4. The compound or the pharmaceutically acceptable salt thereof as claimed in claim 1, wherein $R^4$ is a lower alkylidene group.

5. The compound or the pharmaceutically acceptable salt thereof of claim 3, wherein $R^6$ is a phenyl group which may have 1 to 3 substituents, said substituent is a halogen atom, a hydroxyl group, a nitro group, a lower alkyl group, a lower alkoxy group, a lower alkylthio group, a carboxyl group, a lower alkoxycarbonyl group, a phenyl-lower alkoxy group, a lower alkylenedioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group or a 6-lower alkanoyloxy-2,5,7,8-tetramethyl-2-chromanylmethyloxy group; and $R^7$ is a hydrogen atom.

6. The compound or the pharmaceutically acceptable salt thereof of claim 3, wherein $R^6$ is a lower alkyl group, a carboxy-lower alkyl group, a lower alkoxycarbonyl lower alkyl group, a phenyl-lower alkyl group, a lower cycloalkyl group, a naphthyl group, a 3,4-dihydroxycarbostyryl group, a morpholino group or a 5-membered or 6-membered unsaturated heterocyclic-lower alkyl group having 1 or 2 hetero atoms, said hetero atom is a nitrogen atom, an oxygen atom or a sulfur atom.

7. The compound or the pharmaceutically acceptable salt thereof of claim 5,
wherein $R^6$ is a phenyl group which may have 1 to 3 substituents, said substituent is a halogen atom, a lower alkyl group or a carboxyl group.

8. A compound selected from the group consisting of:
2-isopropylidenehydrazono-5-(N-phenylcarbamoylmethyl)thiazolidin-4-one,
5-[N-(2-carboxy-4-methylphenyl)carbamoylmethyl]-2-isopropylidenehydrazonothiazolidin-4-one,
5-[N-(3,4-difluorophenyl)carbamoylmethyl]-2-isopropylidenehydrazonothiazolidin-4-one,
5-[N-(2-carboxy-4-chlorophenyl)carbamoylmethyl]-2-isopropylidenehydrazonothiazolidin-4-one,
5-[N-(2,6-dimethylphenyl)carbamoylmethyl]-2-isopropylidenehydrazonothiazolidin-4-one,
5-[N-(4-fluorophenyl)carbamoylmethyl]-2-isopropylidenehydrazonothiazolidin-4-one,
and pharmaceutically acceptable salts thereof.

9. A compound selected from the group consisting of:
2-isopropylidenehydrazono-5-(N-phenylcarbamoylmethyl)thiazolidin-4-one,
5-[N-(2-carboxy-4-methylphenyl)carbamoylmethyl]-2-isopropylidenehydrazonothiazolidin-4-one,
and pharmaceutically acceptable salts thereof.

10. A compound selected from the group consisting of:
2-isopropylidenehydrazono-5-(N-phenylcarbamoylmethyl)thiazolidin-4-one,
5-[N-(2-carboxy-4-methylphenyl)carbamoylmethyl]-2-isopropylidenehydrazonothiazolidin-4-one,
2-isopropylidenehydrazono-5-[4-(3-pyridylmethoxy)benzyl]thiazolidin-4-one,
5-[N-(3,4-difluorophenyl)carbamoylmethyl]-2-isopropylidenehydrazonothiazolidin-4-one,
5-[N-(4-chlorophenyl)carbamoylmethyl]-2-isopropylidenehydrazonothiazolidin-4-one,
2-isopropylidenehydrazono-5-[N-(4-methoxyphenyl)carbamoylmethyl]thiazolidin-4-one,
2-isopropylidenehydrazono-5-(N-methyl-N-phenylcarbamoylmethyl)thiazolidin-4-one,
2-isopropylidenehydrazono-5-[N-(4-morpholinophenyl)carbamoylmethyl]thiazolidin-4-one,
2-isopropylidenehydrazono-5-[N-(1-phenylethyl)carbamoylmethyl]thiazolidin-4-one,
2-isopropylidenehydrazono-5-[N-(2-methyl-5-methoxycarbonylphenyl)carbamoylmethyl]thiazolidin-4-one,
and pharmaceutically acceptable salts thereof.

11. A compound selected from the group consisting of:
5-[4-(2,6-dichlorobenzyloxy)benzyl]-2-isopropylidenehydrazonoimidazolidin-4-one,
5-[4-(4-chlorobenzyloxy)benzyl]-2-isopropylidenehydrazonoimidazolidin-4-one,
2-isopropylidenehydrazono-5-(4-phenylthio-benzyl)imidazolidin-4-one,
5-(3,4-dihydroxybenzyl)-2-isopropylidenehydrazonoimidazolidin-4-one,
5-(4-benzyloxycarbonylaminobutyl)-2-isopropylidenehydrazonoimidazolidin-4-one,
2-isopropylidenehydrazono-5-(4-methoxycarbonylaminobutyl)imidazolidin-4-one,
5-benzyloxycarbonylmethyl-2-isopropylidenehydrazonoimidazolidin-4-one,
2-isopropylidenehydrazono-5-methoxycarbonylmethylimidazolidin-4-one,
2-isopropylidenehydrazono-5-(N-phenylcarbamoylmethyl)imidazolidin-4-one,
and pharmaceutically acceptable salts thereof.

12. A compound selected from the group consisting of:
5-[4-(2,6-dichlorobenzyloxy)benzyl]-2-isopropylidenehydrazonoimidazolidin-4-one,
5-[4-(4-chlorobenzyloxy)benzyl]-2-isopropylidenehydrazonoimidazolidin-4-one,
2-isopropylidenehydrazino-4-(4-phenyl-thiophenyl)thiazole,
5-[N-(2-carboxy-4-methylphenyl)carbamoylmethyl]-2-isopropylidenehydrazonothiazolidin-4-one,
2-isopropylidenehydrazono-5-[4-(3-pyridylmethoxy)benzyl]thiazolidin-4-one,
5-(3,4-dihydroxybenzyl)-2-isopropylidenehydrazonoimidazolidin-4-one,
5-[N-(3,4-difluorophenyl)carbamoylmethyl]-2-isopropylidenehydrazonothiazolidin-4-one,
2-isopropylidenehydrazono-5-[N-(4-methoxyphenyl)carbamoylmethyl]thiazolidin-4-one,
2-isopropylidenehydrazono-5-[N-(2-methyl-5-methoxycarbonylphenyl)carbamoylmethyl]thiazolidin-4-one,
4-[N-(3,4-dimethoxyphenyl)carbamoylmethyl]-2-isopropylidenehydrazinothiazole,
and pharmaceutically acceptable salts thereof.

13. A method for treating diseases caused by a Maillard reaction in living body which comprises administrating at least one compound selected from those represented by the general formula:

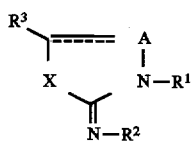

wherein:

$R^1$ represents a hydrogen atom, a lower alkoxycarbonyl-lower alkyl group, a phenyl-lower alkyl group which may have from 1 to 3 substituents selected from a halogen atom, a hydroxyl group, a nitro group, a lower alkyl group, a lower alkoxy group and a lower alkylthio group on the phenyl ring thereof, or a phenyl group which may have 1 to 3 substituents selected from a halogen atom, a hydroxyl group, a nitro group, a lower alkyl group, a lower alkoxy group and a lower alkylthio group;

$R^2$ represents an amino group, a phenylsulfonylamino group which may have a substituent selected from a halogen atom, a hydroxyl group, an amino group and a lower alkanoylamino group on the phenyl ring thereof, or —N=$R^4$ (wherein $R^4$ represents a lower alkylidene group, a lower alkylidene group having 1 or 2 lower cycloalkyl groups, a lower cycloalkylidene group, a diphenyl-lower alkylidene group or a phenyl-lower alkylidene group);

$R^3$ represents:
a hydrogen atom,
a lower alkyl group,
a lower alkenyl group,
a phenyl-lower alkoxy-lower alkyl group,
a phenyl group which may have a hydroxyl group,
a 5-membered or 6-membered unsaturated heterocyclic-lower alkyl group having 1 or 2 hetero atoms selected from a nitrogen atom and a sulfur atom (said heterocyclic ring may be condensed with a benzene ring and a hydroxyl group may be located as a substituent on either one or both of said heterocyclic ring and said benzene ring being condensed therewith), —W—(NH)$_b$—CO—OR$^5$ (wherein W represents a lower alkylene group, R$^5$ represents a hydrogen atom, a lower alkyl group, or a phenyl-lower alkyl group, and b is 0 or 1), —Z—CO—R$^a$ {wherein Z represents a lower alkylene group, R$^a$ represents —Tyr(OR$^{a1}$)—OR$^{b1}$, —Leu—OR$^{b2}$, —Trp—OR$^{b3}$, —Asp(OR$^{a2}$)—OR$^{b4}$, —Ph—Gly—OR$^{b5}$ (wherein R$^{a1}$ and R$^{a2}$ each represents a hydrogen atom or a benzyl group, and R$^{b1}$, R$^{b2}$, R$^{b3}$, R$^{b4}$ and R$^{b5}$ each represents a hydrogen atom or a lower alkyl group) or —N(R$^6$)—R$^7$ (wherein R$^6$ represents a lower alkyl group, a carboxy-lower alkyl group, a lower alkoxycarbonyl-lower alkyl group, a phenyl-lower alkyl group, a lower cycloalkyl group, a phenyl group which may have 1 to 3 substituents selected from a halogen atom, a hydroxyl group, a nitro group, a lower alkyl group, a lower alkoxy group, a lower alkylthio group, a carboxyl group, a lower alkoxycarbonyl group, a phenyl-lower alkoxy group, a lower alkylenedioxy group, a morpholino group, a halogenated lower alkyl group, a carboxy-lower alkyl group, a lower alkoxycarbonyl-lower alkyl group, a 6-hydroxy-2,5,7,8-tetramethyl-2-chromanylmethyloxy group and a 6-lower alkanoyloxy-2,5,7,8-tetramethyl-2-chromanylmethyloxy group, a naphthyl group, a 3,4-dihydroxycarbostyryl group, a morpholino group, or a 5-membered or 6-membered unsaturated heterocyclic-lower alkyl group having 1 or 2 hetero atoms selected from a nitrogen atom, an oxygen atom and a sulfur atom, and R$^7$ represents a hydrogen atom or a lower alkyl group)}, or a group:

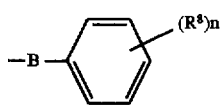

{wherein B represents a lower alkylene group, R$^8$ represents a hydroxyl group, a nitro group, an amino group, a halogen atom, a lower alkyl group, a lower alkoxy group, a phenoxy group, a phenyl-lower alkyl group, a lower alkylthio group, a phenylthio group which may have a halogen atom, a phenyl-lower alkylthio group, a benzoylamino group which may have 1 to 3 halogen atoms, or —O—D—R$^9$ (wherein D represents a lower alkylene group, R$^9$ represents a phenyl group which may have 1 to 3 substituents selected from a halogen atom, a hydroxyl group, a nitro group, a lower alkyl group, a lower alkoxy group and a lower alkylthio group on the phenyl ring thereof (said phenyl ring may be condensed with a benzene ring or a cyclohexane ring), a 5-membered or 6-membered, saturated or unsaturated heterocyclic group having a hetero atom selected from a nitrogen atom, a sulfur atom and an oxygen atom (said heterocyclic ring may be condensed with a benzene ring and 1 to 5, in total, substituents selected from a hydroxyl group and a lower alkyl group may be located on either one of both of said heterocyclic ring or the benzene ring being condensed with said heterocyclic ring), a lower cycloalkyl group or a naphthoquinone group), and n is 0 or an integer of from 1 to 3};

X represents —S— or —N(R$^{10}$)— (wherein R$^{10}$ represents a hydrogen atom or a lower alkoxycarbonyl-lower alkyl group);

═ represents a single bond or a double bond;

A, when ═ is a single bond, represents a carbonyl group, or A, when ═ is a double bond, represents ═C(R$^{11}$)— {wherein R$^{11}$ represents a lower alkyl group which may have 1 to 3 halogen atoms, a lower alkoxycarbonyl-lower alkyl group, a carboxy-lower alkyl group, a pyridyl group, a thienyl group, a thiazolyl group, a phenylcarbamoyl-lower alkyl group which may have 1 or 2 lower alkoxy groups on the phenyl ring thereof, or a group:

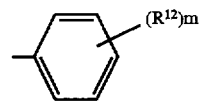

(wherein R$^{12}$ represents a halogen atom, a hydroxyl group, a nitro group, a lower alkyl group, a lower alkoxy group, a lower alkylthio group, a carboxyl group, a phenylthio group, or a phenyl-lower alkoxy group which may have 1 to 3 halogen atoms on the phenyl ring thereof, and m is an integer of from 1 to 3)}; and the above R$^4$ and R$^{10}$ may bind to each other to form a 6- to 8-membered ring (with the proviso that A represents a carbonyl group in this case), and R$^3$ and R$^{11}$ may bind to each other to form a 5- to 8-membered ring, with the proviso that, when R$^3$ represents a hydrogen atom and A represents a carbonyl group, R$^1$ does not represent a hydrogen atom or a lower alkoxycarbonyl-lower alkyl group;

or a pharmaceutically acceptable salt thereof.

14. The method as claimed in claim 13, wherein said disease caused by a Maillard reaction in living body is diabetic complications, atherosclerosis or senile cataract.

15. The method as claimed in claim 13, wherein ═ represents a single bond; A represents a carbonyl group; and R$^1$ represents a hydrogen atom, a lower alkoxycarbonyl-lower alkyl group or a phenyl group which may have 1 to 3 substituents selected from a halogen atom, a hydroxyl group, a nitro group, a lower alkyl group, a lower alkoxy group and a lower alkylthio group.

16. A method for treating diseases caused by a Maillard reaction in living body which comprises administrating a compound selected from those represented by the general formula:

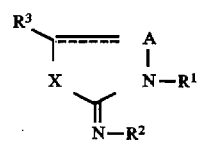

wherein:

R$^1$ represents a hydrogen atom, a lower alkoxycarbonyl-lower alkyl group, a phenyl-lower alkyl group which may have from 1 to 3 substituents selected from a halogen atom, a lower alkyl group and a lower alkoxy group on the phenyl ring thereof, or a phenyl group which may have 1 to 3 substituents selected from a halogen atom, a lower alkyl group and a lower alkoxy group;

R$^2$ represents —N═R$^4$ (wherein R$^4$ represents a lower alkylidene group, a diphenylmethylene group or a phenyl-lower alkylidene group);

R$^3$ represents a hydrogen atom, a lower alkyl group, —CH$_2$—CO—OR$^5$ (wherein R$^5$ represents a hydrogen atom or a lower alkyl group), a phenyl group which may have a hydroxyl group, a 5-membered or 6-membered unsaturated heterocyclic-lower alkyl group having a hetero atom selected from a nitrogen atom and a sulfur atom, —CH$_2$—CO—NHR$^6$ (wherein R$^6$ represents a lower alkyl group, a carboxy-lower alkyl group, a lower alkoxycarbonyl-lower alkyl group, a phenyl-lower alkyl group, a lower cycloalkyl group, a phenyl group which may have 1 or 2 substituents selected from a carboxyl group and a lower alkoxycarbonyl group, or a 3,4-dihydrocarbostyryl group), a phenyl-lower alkoxy-lower alkyl group or a group:

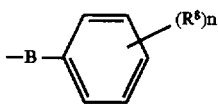

{wherein B represents a lower alkylene group, R$^8$ represents a hydroxyl group, a nitro group, an amino group, a halogen atom, a lower alkyl group, a lower alkoxy group, a phenoxy group, a phenyl-lower alkyl group, a lower alkylthio group, a phenylthio group, a phenyl-lower alkylthio group, a benzoylamino group which may have 1 to 3 halogen atoms, a phenyl-lower alkoxy group which may have 1 to 3 substituents selected from a halogen atom, a lower alkyl group and a lower alkoxy group on the phenyl ring thereof (the phenyl ring of said phenyl-lower alkoxy group may be condensed with a benzene ring or a cyclohexane ring), a 5-membered or 6-membered, saturated or unsaturated heterocyclic-lower alkoxy group having a hetero atom selected from a nitrogen atom, a sulfur atom and an oxygen atom (said heterocyclic ring may be condensed with a benzene ring and 1 to 5 substituents selected from a hydroxyl group and a lower alkyl group may be located on said heterocyclic ring and the benzene ring being condensed with the heterocyclic ring), or —O—D—R$^9$ (wherein D represents a lower alkylene group, R$^9$ represents a lower cycloalkyl group or a naphthoquinone group), and n is 0 or an integer of from 1 to 3};

X represents —S— or —N(R$^{10}$)— (wherein R$^{10}$ represents a hydrogen atom or a lower alkoxycarbonyl-lower alkyl group);

--- represents a single bond or a double bond;

A, when --- is a single bond, represents a carbonyl group, or A, when --- is a double bond, represents =C(R$^{11}$)— {wherein R$^{11}$ represents a lower alkyl group or a group:

(wherein R$^{12}$ represents a halogen atom, a lower alkyl group, a lower alkoxy group, a hydroxyl group, a phenylthio group or a phenyl-lower alkoxy group which may have 1 to 3 halogen atoms on the phenyl ring thereof, and m is 0 or an integer of from 1 to 3)}; and the above R$^4$ and R$^{10}$ may bind to each other to form a 6- to 8-membered ring (with the proviso that A represents a carbonyl group in this case), and R$^3$ and R$^{11}$ may bind to each other to form a 5- to 8-membered ring, with the proviso that, when R$^3$ represents a hydrogen atom and A represents a carbonyl group, R$^1$ does not represents a hydrogen atom or a lower alkoxycarbonyl-lower alkyl group; or a pharmaceutically acceptable salt thereof.

* * * * *